US010286000B2

(12) United States Patent
Leung et al.

(10) Patent No.: US 10,286,000 B2
(45) Date of Patent: May 14, 2019

(54) RETINOID X RECEPTOR-GAMMA AGONISTS AND RETINOID X RECEPTOR-ALPHA ANTAGONISTS FOR TREATMENT OF CANCER

(71) Applicant: St. Jude Children's Research Hospital, Inc., Memphis, TN (US)

(72) Inventors: Wai-Hang Leung, Memphis, TN (US); Wing Leung, Memphis, TN (US)

(73) Assignee: St. Jude Children's Research Hospital, Inc., Memphis, TN (US)

( * ) Notice: Subject to any disclaimer, the term of this patent is extended or adjusted under 35 U.S.C. 154(b) by 107 days.

(21) Appl. No.: 15/031,426

(22) PCT Filed: Oct. 24, 2014

(86) PCT No.: PCT/US2014/062179
§ 371 (c)(1),
(2) Date: Apr. 22, 2016

(87) PCT Pub. No.: WO2015/061686
PCT Pub. Date: Apr. 30, 2015

(65) Prior Publication Data
US 2016/0324874 A1    Nov. 10, 2016

Related U.S. Application Data

(60) Provisional application No. 61/895,767, filed on Oct. 25, 2013.

(51) Int. Cl.
*A61K 31/56* (2006.01)
*A61K 31/58* (2006.01)
*A61K 31/585* (2006.01)

(52) U.S. Cl.
CPC .......... *A61K 31/585* (2013.01); *A61K 31/56* (2013.01); *A61K 31/58* (2013.01)

(58) Field of Classification Search
CPC ....... A61K 31/585; A61K 31/56; A61K 31/58
See application file for complete search history.

(56) References Cited

U.S. PATENT DOCUMENTS

| | | |
|---|---|---|
| 2001/0046980 A1 | 11/2001 | Loria |
| 2009/0048156 A1* | 2/2009 | Brodie .................. A61K 31/10 514/1.1 |
| 2013/0150333 A1 | 6/2013 | Thacher et al. |
| 2013/0203719 A1 | 8/2013 | Kalergis et al. |

FOREIGN PATENT DOCUMENTS

WO      2012112623 A2      8/2012

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Albini et al., "Tumor Cell Invasion Inhibited by TIMP-2", Journal of the National Cancer Institute (1991), vol. 83:11, p. 775-779.
Armeanu et al., "Natural Killer Cell-Mediated Lysis of Hepatoma Cells via Specific Induction of NKG2D Ligands by the Histone Deacetylase Inhibitor Sodium Valproate", Cancer Research (2005), vol. 65:14, p. 6321-6329.
Boehm et al., "Synthesis and Structure-Activity Relationships of Novel Retinoid X Receptor-Selective Retinoids", Journal of Medicinal Chemistry (1994), vol. 37:18, p. 2930-2941.
Brew et al., "The tissue inhibitors of metalloproteinases (TIMPs): An ancient family with structural and functional diversity", Biochimica et Biophysica Acta 1803 (2010), p. 55-71.
Champsaur et al., "Effect of NKG2D ligand expression on host immune responses", Immunological Reviews (2010), vol. 235, p. 267-285.
Chan et al., "Antibody-Dependent Cell-Mediated Cytotoxicity Overcomes NK Cell Resistance in MLL-Rearranged Leukemia Expressing Inhibitory KIR Ligands but Not Activating Ligands", Clin. Cancer Res. (2012), vol. 18:22, p. 6296-6305.
Dawson et al., "The retinoid X receptors and their ligands", Biochimica et Biophysica Acta 1821 (2012), p. 21-56.
Diermayr et al., "NKG2D ligand expression in AML increases in response to HDAC inhibitor valproic acid and contributes to allorecognition by NK-cell lines with single KIR-HLA class I specificities", Blood (2008), vol. 111:03, p. 1428-1436.
Dunn et al., "Human Cytomegalovirus Glycoprotein UL16 Causes Intercellular Sequestration of NKG2D Ligands, Protecting Against Natural Killer Cell Cytotoxicity", J. Exp. Med. (2003), vol. 197:11, p. 1427-1439.
Fuertes et al., "Intracellular Retention of the NKG2D Ligand MHC Class I Chain-Related Gene A in Human Melanomas Confers Immune Privilege and Prevents NK Cell-Mediated Cytotoxicity", The Journal of Immunology (2008), vol. 180, p. 4606-4614.
Fujisaki et al., "Expansion of Highly Cytotoxic Human Natural Killer Cells for Cancer Cell Therapy", Cancer Research (2009), vol. 69:09, p. 4010-4017.
Gasser et al., "The DNA damage pathway regulates innate immune system ligands of the NKG2D receptor", Nature (2005), vol. 436, p. 1186-1190.
Gonzalez et al., "NKG2D ligands: key targets of the immune response", Trends in Immunology (2008), vol. 29:08, p. 397-403.
Groh et al., "Cell stress-regulated human major histocompatibility complex class I gene expressed in gastrointestinal epithelium", Proc. Natl. Acad. Sci. USA (1996), vol. 93, p. 12445-12450.
Huang et al., "Retinoid X receptor gamma signaling accelerates CNS remyelination", Nature Neuroscience (2011), vol. 14:01, p. 45-53.
Jinushi et al., "Expression and Role of Mica and Micb in Human hepatocellular Carcinomas and Their Regulation by Retinoic Acid", Int. J. Cancer (2003), vol. 104, p. 354-361.
Ljunggren et al., "Prospects for the use of NK cells in immunotherapy of human cancer", Nature Reviews Immunology (2007), vol. 07, p. 329-339.
Loging et al., "Inhibition of the putative tumor supressor gene TIMP-3 by tumor-derived p53 mutants and wild type p53", Oncogene (1999), vol. 18, p. 7608-7615.

(Continued)

*Primary Examiner* — Shawquia Jackson
(74) *Attorney, Agent, or Firm* — Troutman Sanders LLP

(57) ABSTRACT

The invention is directed to the use of Retinoid X Receptor-gamma (RXR-gamma) agonists and Retinoid X Receptor-alpha (RXR-alpha) antagonists in treatment of cancer.

3 Claims, 36 Drawing Sheets
Specification includes a Sequence Listing.

(56) References Cited

OTHER PUBLICATIONS

López-Soto et al., "HDAC3 represses the expression of NKG2D ligands ULBPs in epithelial tumour cells: potential implications for the immunosurveillance of cancer", Oncogene (2009), vol. 28, p. 2370-2382.

Malemud, Charles J., "Matrix metalloproteinases (MMPs) in health and disease: an overview", Frontiers in Bioscience 11 (2006) (A), p. 1696-1701.

Malemud, Charles J., "Matrix metalloproteinases: role in skeletal development and growth plate disorders", Frontiers in Bioscience 11 (2006) (B), p. 1702-1715.

McGilvray et al., "NKG2D Ligand Expression in Human Colorectal Cancer Reveals Associations with Prognosis and Evidence for Immunoediting", Clin. Cancer Res. (2009), vol. 15:22, p. 6993-7002.

Messerli, Franz H., "TIMPs, MMPs, and cardiovascular disease", European Heart Journal (2004), vol. 25, p. 1475-1476.

Murray et al., "Matrix metalloproteinase-1 is associated with poor prognosis in colorectal cancer", Nature Medicine (1996), vol. 02:04, p. 461-462.

Papi et al., "RXRγ and PPARγ ligands in combination to inhibit proliferation and invasiveness in colon cancer cells", Cancer Letters 297 (2010), p. 65-74.

PCT—International Search Report and Written Opinion for International Application No. PCT/US2014/062179, dated Jun. 5, 2015, p. 1-14.

Pulukuri et al., "Matrix metalloproteinase-1 promotes prostate tumor growth and metastasis", International Journal of Oncology 32 (2008), p. 757-765.

Ring et al., "Expression of tissue inhibitor of metalloproteinases TIMP-2 in human colorectal cancer—a predictor of tumour stage", British Journal of Cancer (1997), vol. 76:06, p. 805-811.

Rujkijyanont et al., "Ex Vivo Activation of CD56+ Immune Cells That Eradicate Neuroblastoma", Cancer Res. (2013), vol. 73:08, p. 2608-2618.

Salih et al., "Cutting Edge: Down-Regulation of MICA on Human Tumors by Proteolytic Shedding", The Journal of Immunology (2002), p. 4098-4102.

Song et al., "MicroRNA-21 regulates breast cancer invasion partly by targeting tissue inhibitor of metalloproteinase 3 expression", Journal of Experimental & Clinical Cancer Research (2010), vol. 29:29, p. 2-8, Http://www.jeccr.com/content/29/1/29.

Soriani et al., "ATM-ATR-dependent up-regulation of DNAM-1 and NKG2D ligands on multiple myeloma cells by therapeutic agents results in enhanced NK-cell susceptibility and associated with a senescent phenotype", Blood (2009), vol. 113:15, p. 3503-3511.

Stern-Ginossar et al., "Human microRNAs regulate stress-induced immune responses mediated by the receptor NKG2D", Nature Immunology (2008), vol. 09:09, p. 1065-1073.

Sunami et al., "MMP-1 is a Prognostic Marker for Hematogenous Metastasis of Colorectal Cancer", The Oncologist (2000), vol. 05, p. 108-114.

Vertuani et al., "Retinoic acid elicits cytostatic, cytotoxic and immunomodulatory effects on uveal melanoma cells", Cancer Immunol. Immunother. (2007), vol. 56, p. 193-204.

Visse et al., "Matrix Metalloproteinases and Tissue Inhibitors of Metalloproteinases: Structure, Function, and Biochemistry", Circulation Research 92 (2003), p. 827-839.

Vivat-Hannah et al., "Separation of Retinoid X Receptor Homo- and Heterodimerization Functions", Molecular and Cellular Biology (2003), vol. 23:21, p. 7678-7688.

Waldhauer et al., "Proteolytic Release of Soluble UL16-Binding Protein 2 from Tumor Cells", Cancer Res. (2006), vol. 66:05, p. 2520-2526.

Williams et al., "Protective Effect of Spironolactone on Endothelial Cell Apoptosis", Endocrinology (2006), vol. 147:05, p. 2496-2505.

Yamamoto et al., "Oxidative stress increases MICA and MICB gene expression in the human colon carcinoma cell line (CaCo-2)", Biochimica et Biophysica Acta 1526 (2001), p. 10-12.

Fernandez, L. et al., "Activated and Expanded Natural Killer Cells Target Osteosarcoma Tumor Initiating Cells in an NKG2D-NKG2DL Dependent Manner". Cancer Letters (2015) vol. 368, pp. 54-63.

* cited by examiner

Figure 1.
B
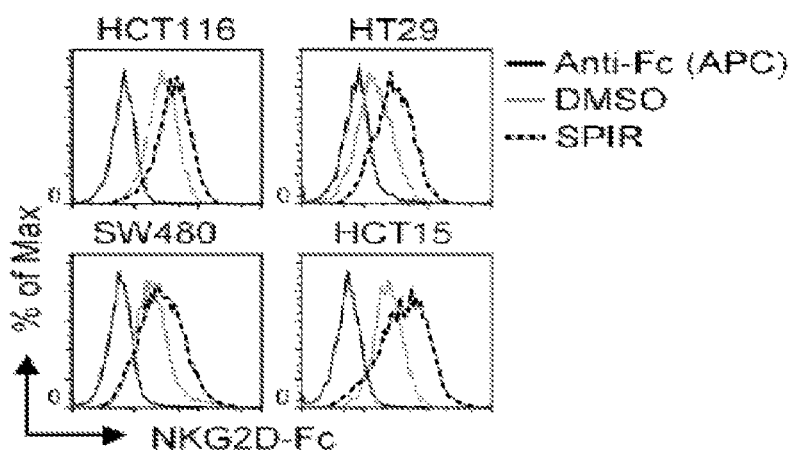
C
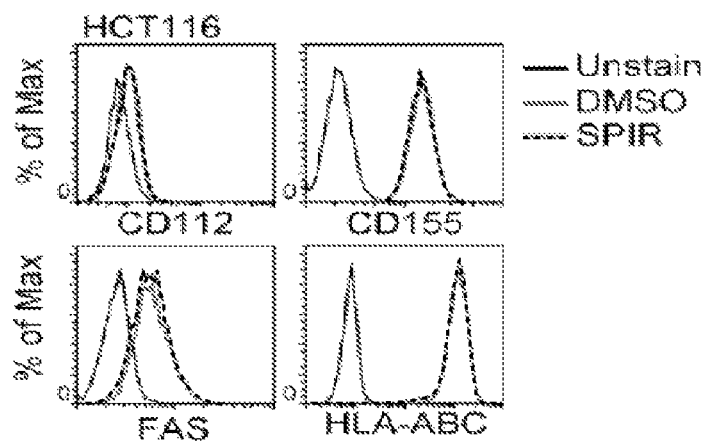
D
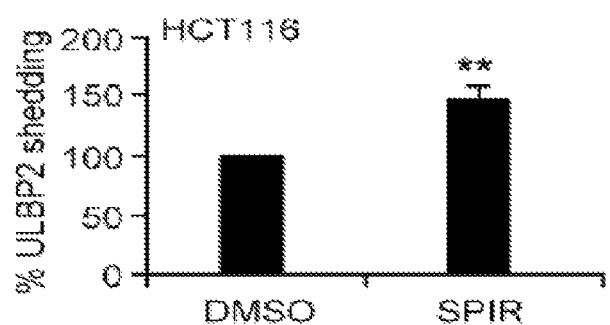

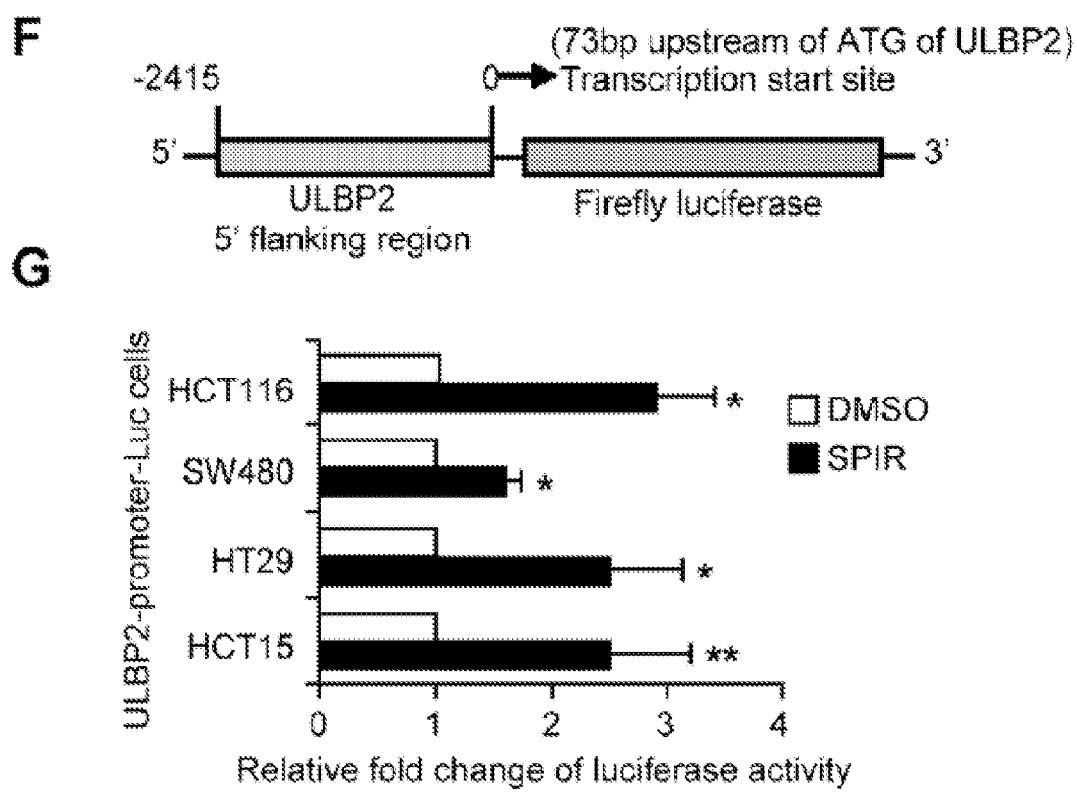

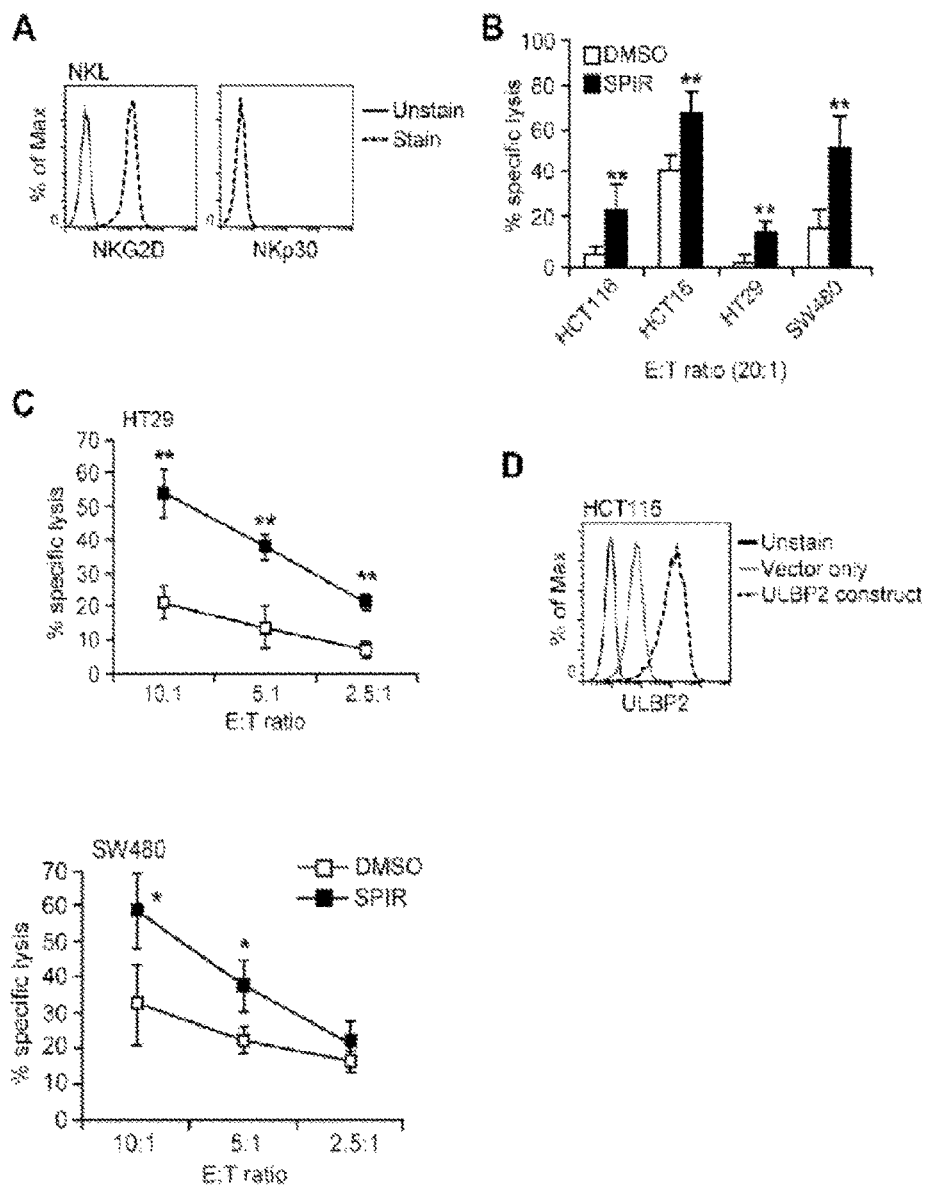

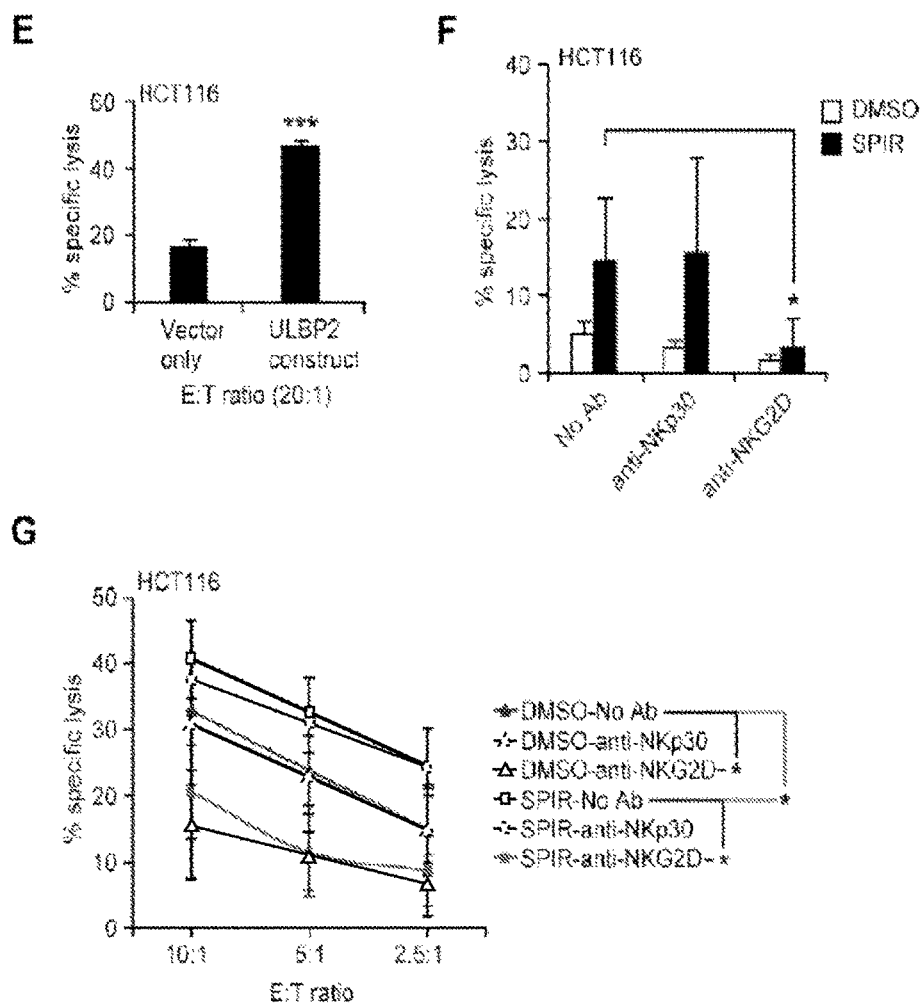

Figure 3.
B
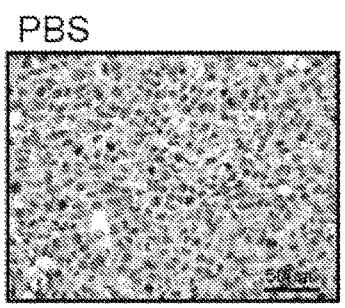
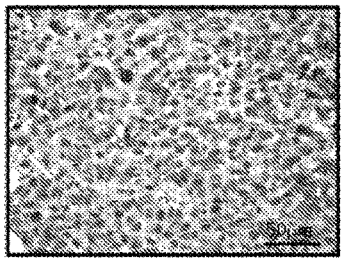
ULBP2 staining
C
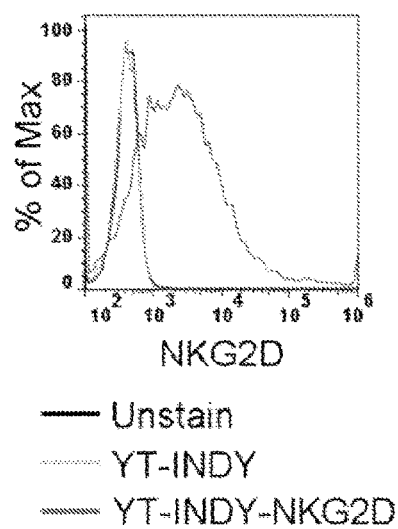

Figure 3.
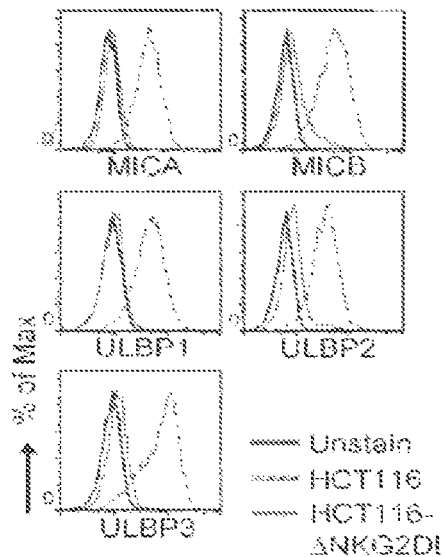
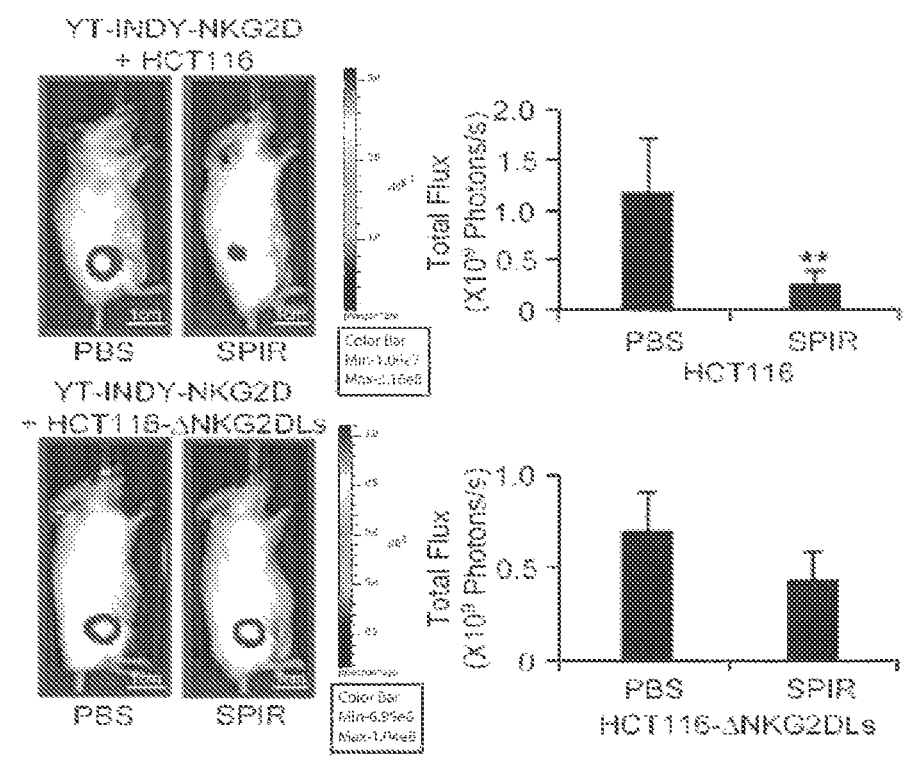

Figure 5.
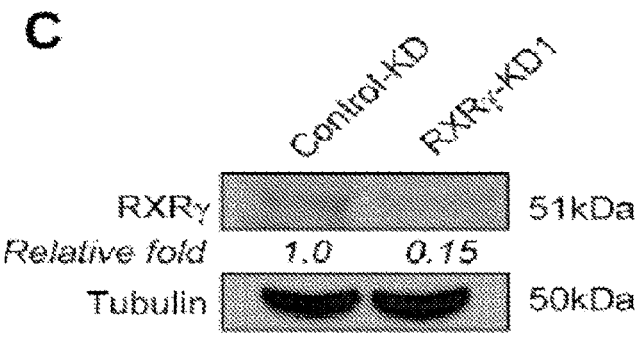
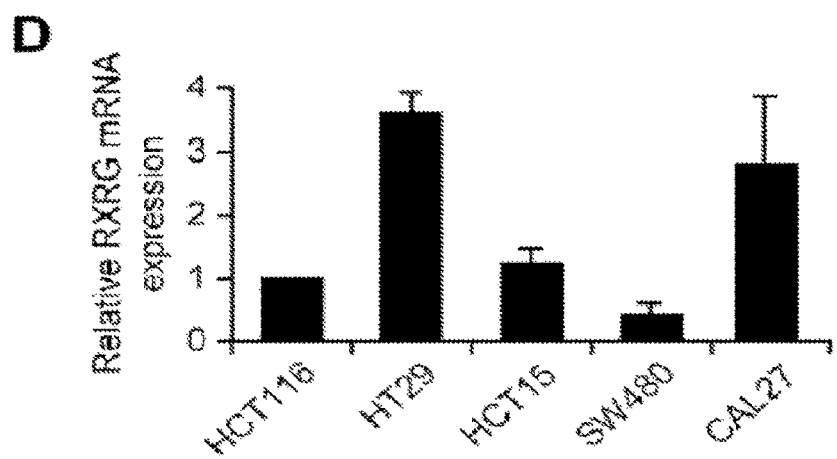
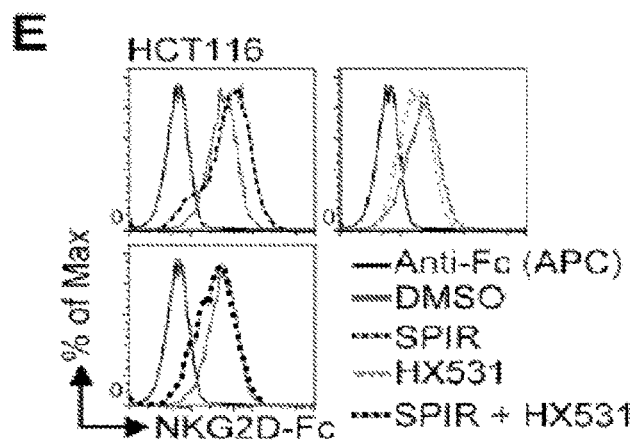

Figure 5.
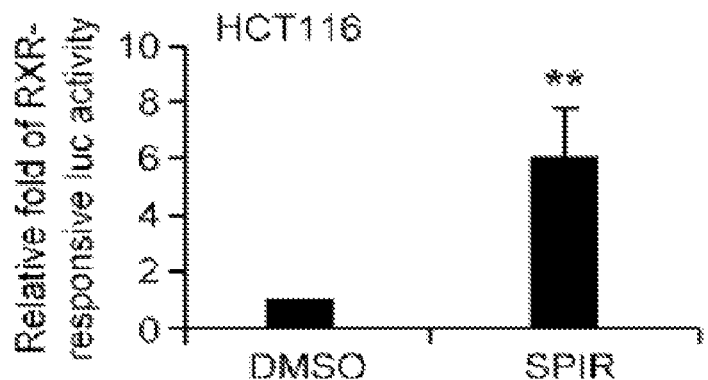
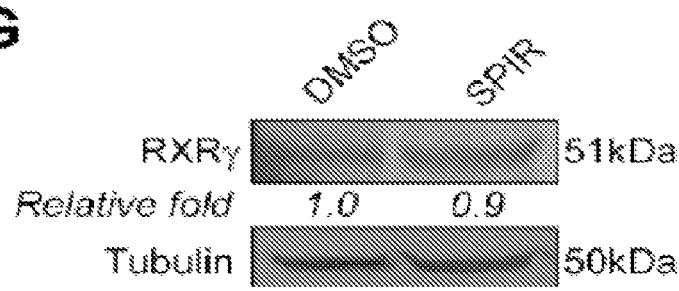
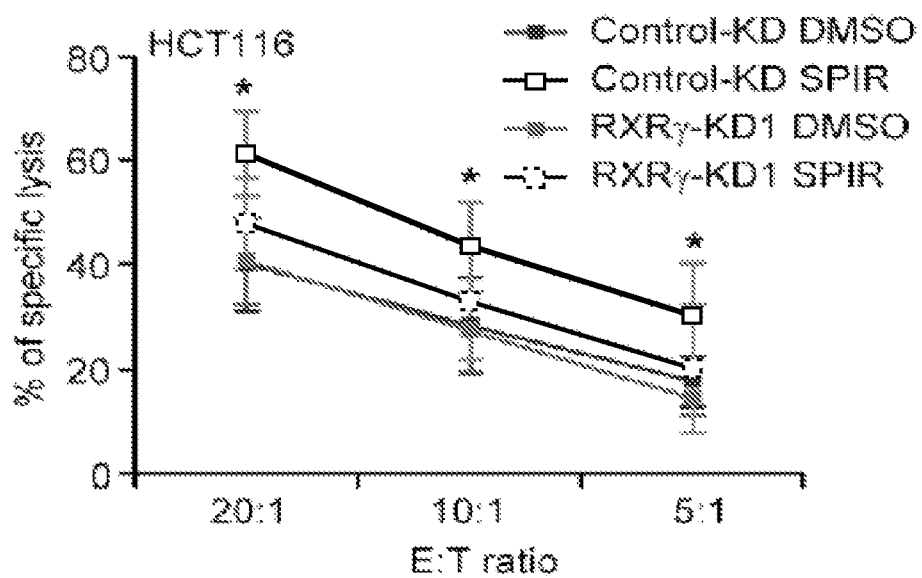

Figure 6.
A
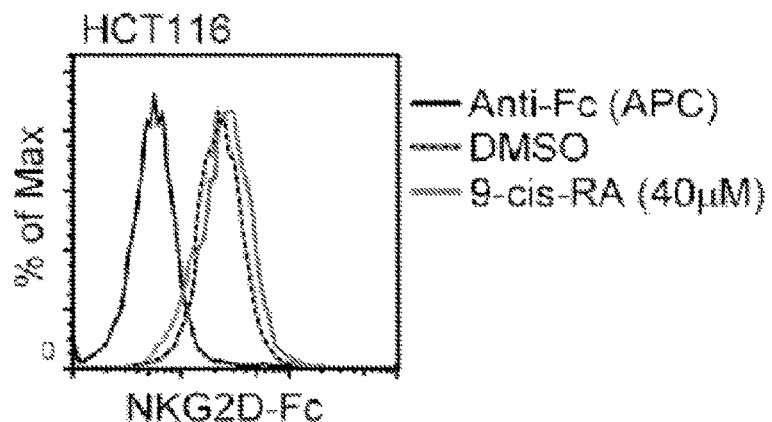
B
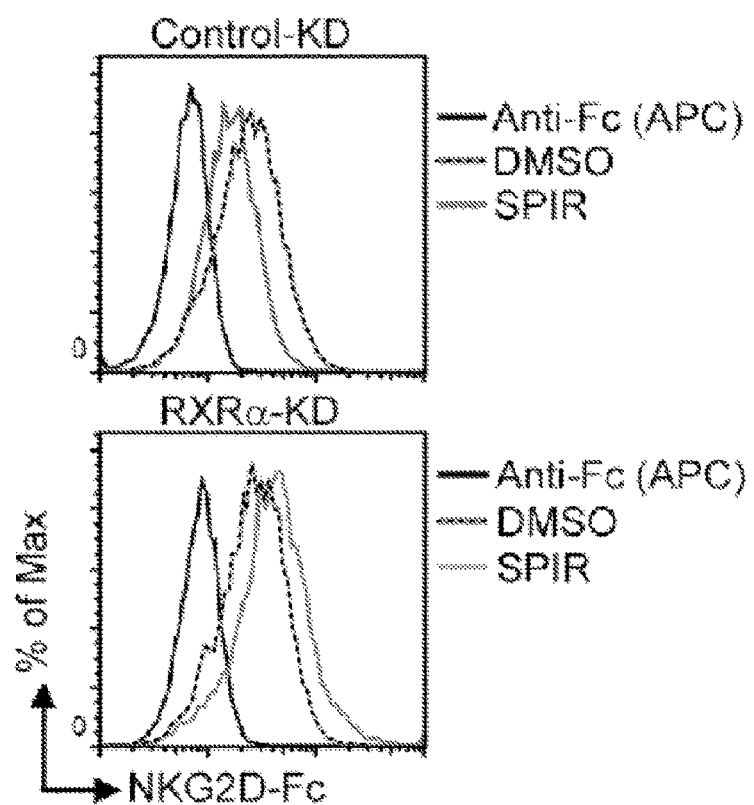

Figure 6.
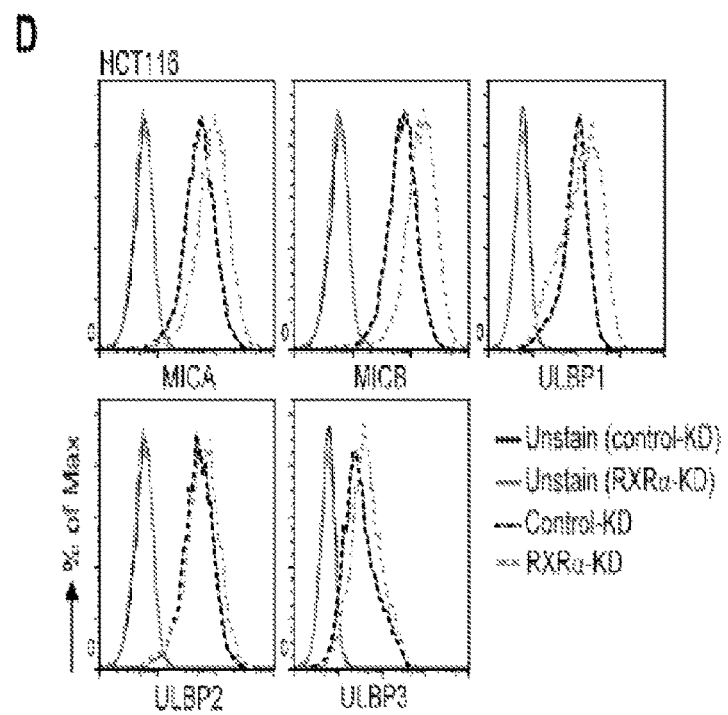
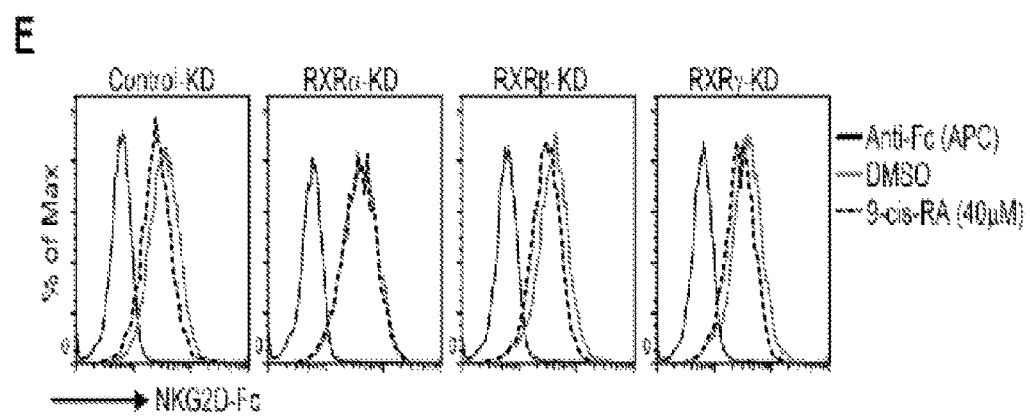

Figure 8.
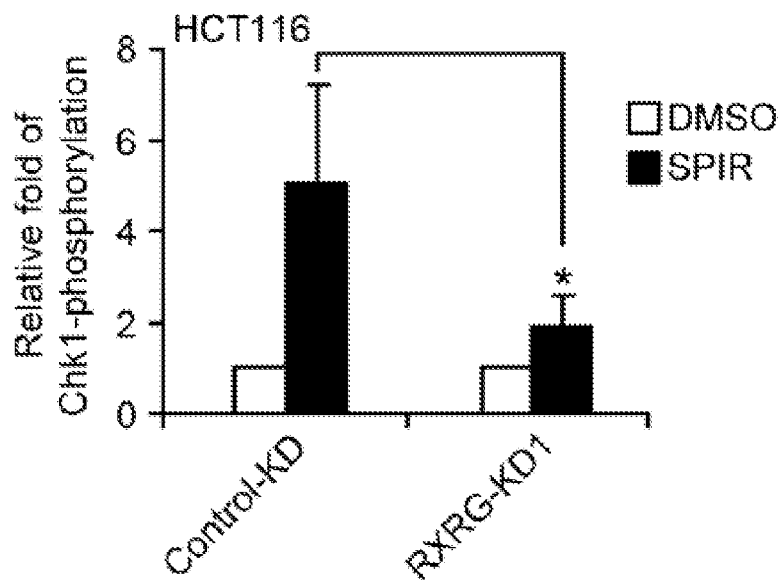
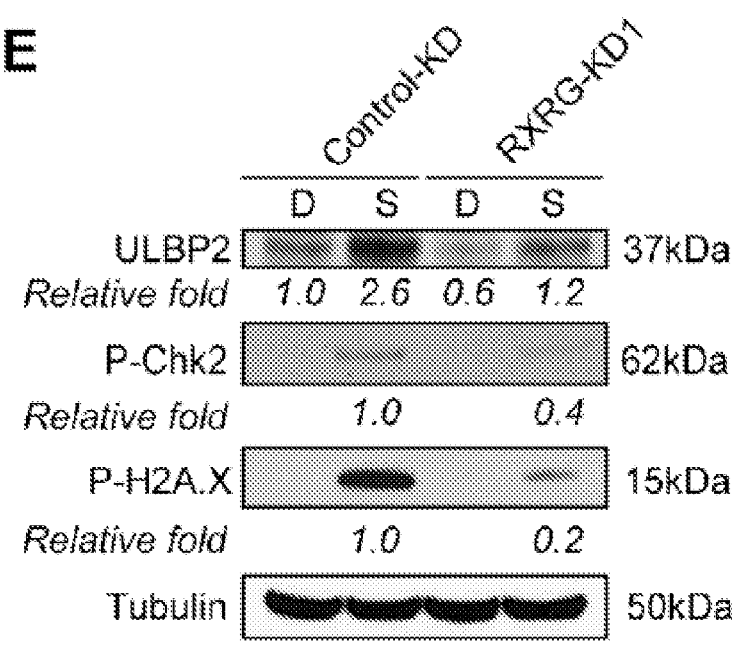

Figure 9.
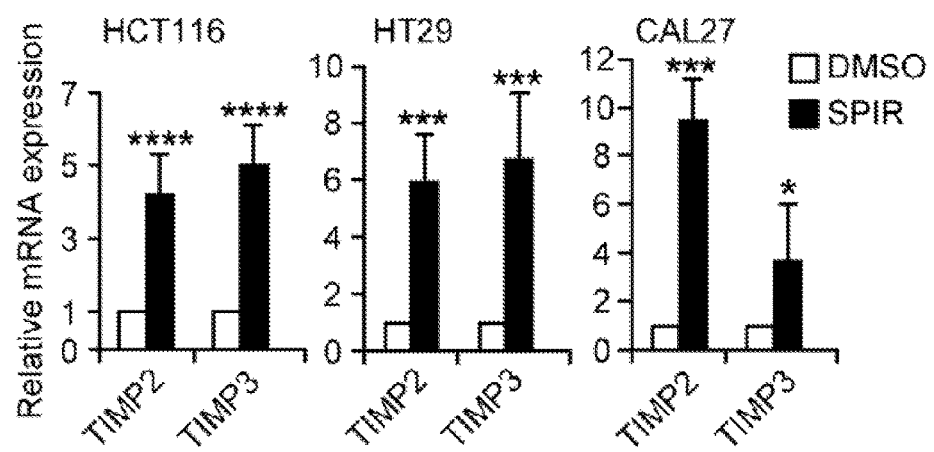
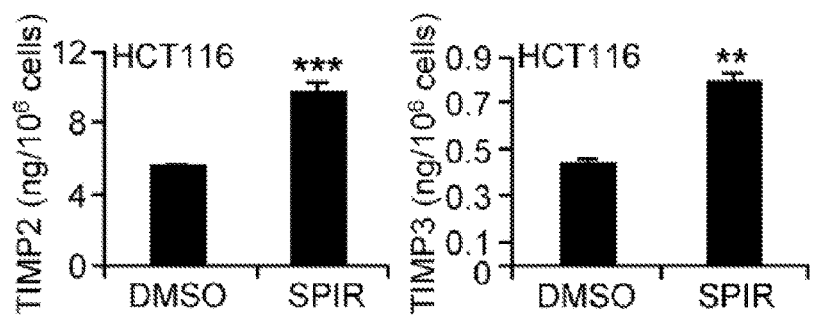

Figure 9.
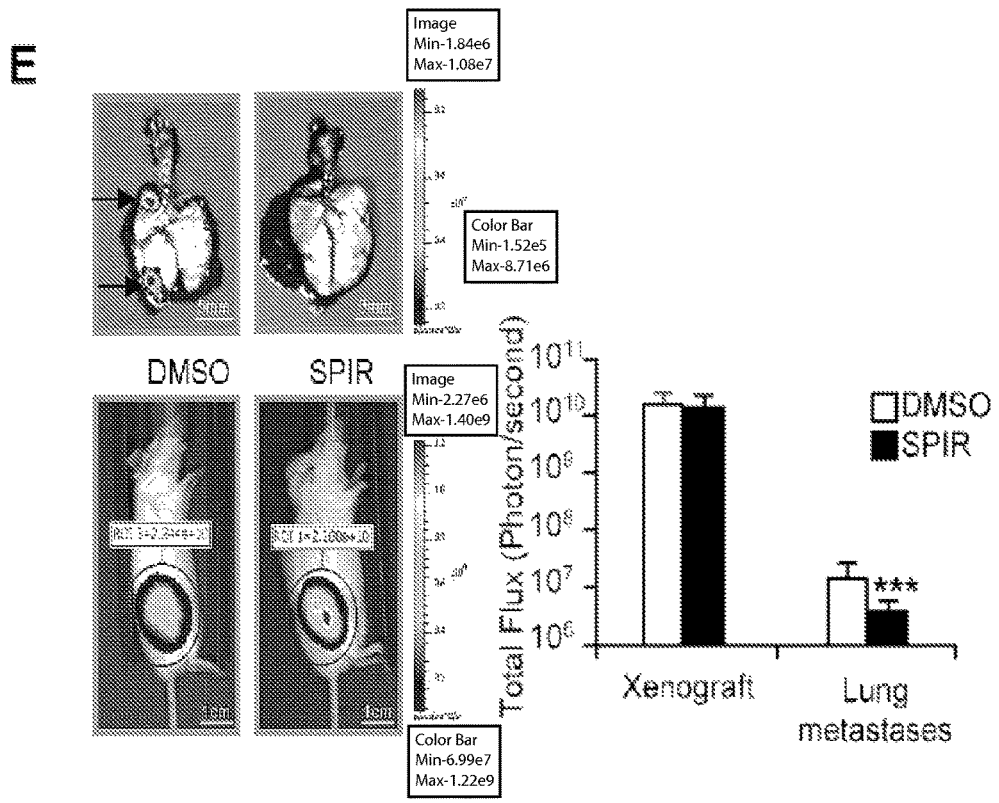
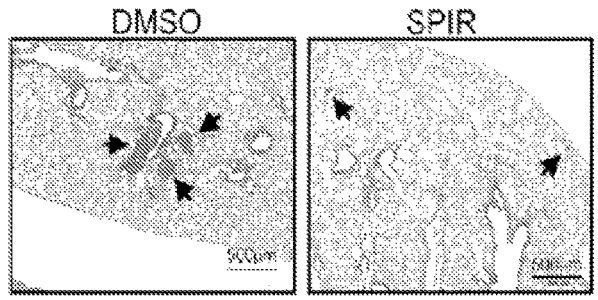

Figure 10.
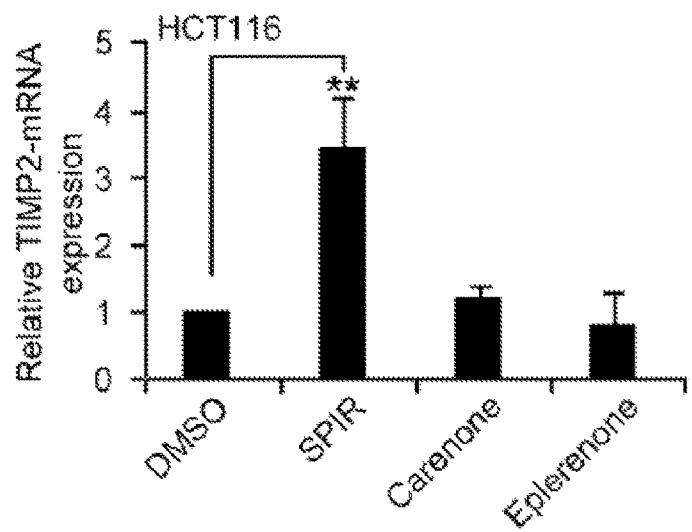
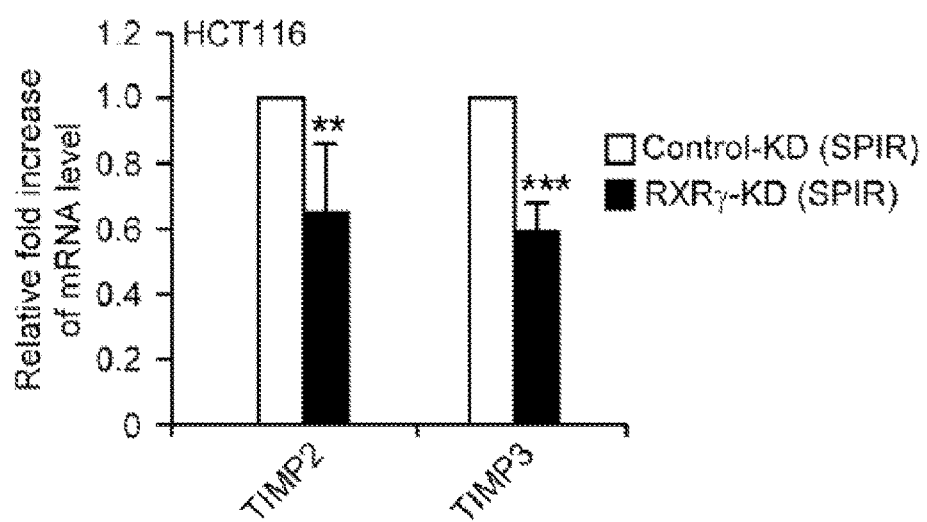

Figure 10.
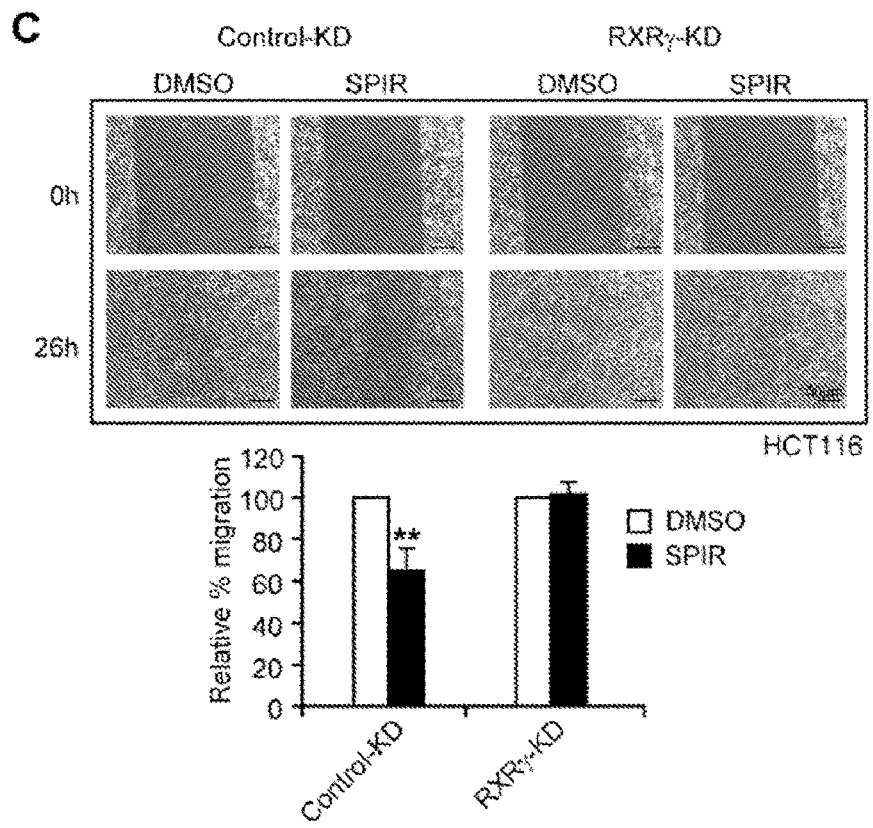
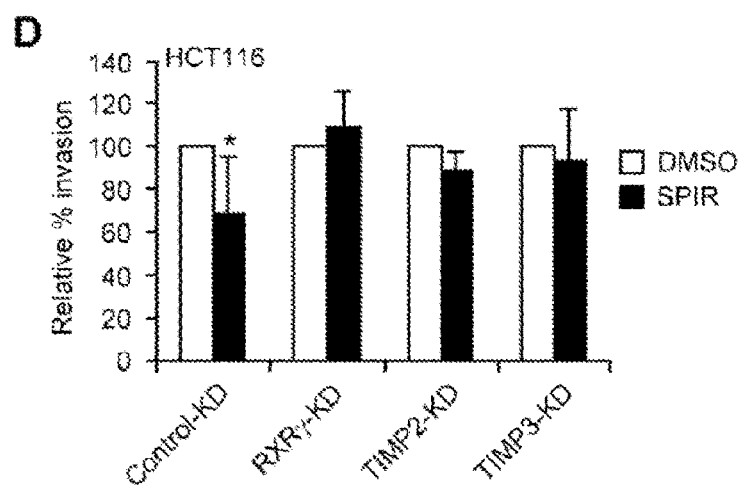

Figure 10.
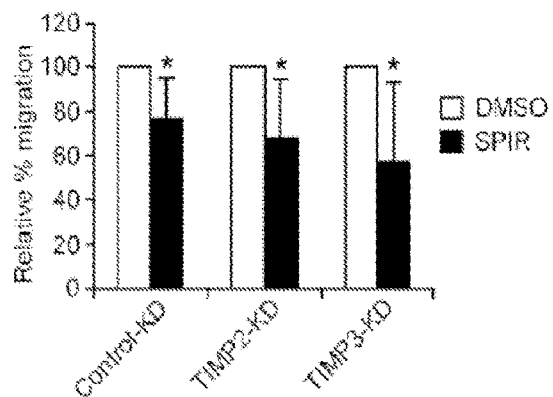
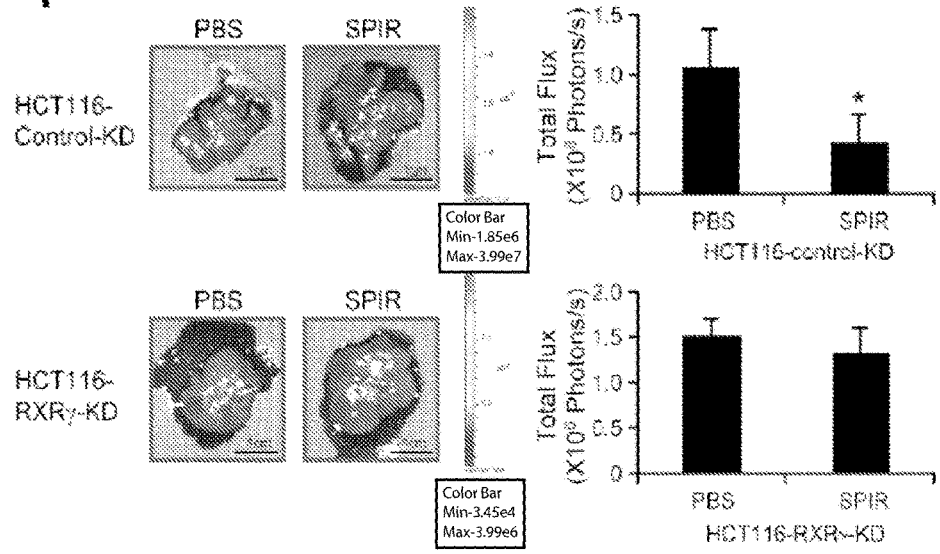

RETINOID X RECEPTOR-GAMMA AGONISTS AND RETINOID X RECEPTOR-ALPHA ANTAGONISTS FOR TREATMENT OF CANCER

CROSS-REFERENCE TO RELATED APPLICATIONS

This application is a U.S. National Phase of International Patent Application No. PCT/US14/62179, filed Oct. 24, 2014, which claims priority to U.S. Provisional Patent Application No. 61/895,767, filed Oct. 25, 2013, both of which applications are herein incorporated by reference in their entirety.

SEQUENCE LISTING

The instant application contains a Sequence Listing which has been submitted electronically in ASCII format and is hereby incorporated by reference in its entirety. Said ASCII copy, created on Oct. 20, 2014, is named 243734.000055_SL.txt and is 8,379 bytes in size.

FIELD OF THE INVENTION

The present invention is directed to the use of Retinoid X Receptor-gamma (RXR-gamma) agonists and Retinoid X Receptor-alpha (RXR-alpha) antagonists in treatment of cancer.

BACKGROUND OF THE INVENTION

Colorectal cancer afflicts approximately 150,000 Americans and one million people worldwide annually (Cappell, M. S. 2008. Gastroenterol Clin North Am 37:1-24). Progress has been made in understanding its molecular carcinogenesis and in early detection. Surgery, chemotherapy, and radiation have remained the mainstays of therapy. Unfortunately, colorectal cancer remains the second leading cause of death from cancer in the United States, and subject survival has improved only modestly during the past two decades. Therefore, further investigations into novel therapies, such as immunotherapies, are warranted.

Both natural killer (NK) cells and cytotoxic T cells express the NKG2D receptor that can recognize NKG2D ligands (NKG2DLs) (e.g., MICA, MICB and ULBP1-6) on tumor cells (Champsaur, M. & L. L. Lanier. 2010. Immunol Rev 235:267-285; Gonzalez et al. 2008. Trends Immunol 29:397-403). Although the molecular mechanism that regulates NKG2DL expression is not clear, a variety of stimuli, such as oxidation, heat shock, and DNA damage, which induce cell stress and tumor transformation, have been shown to selectively upregulate NKG2DL expression (Gasser et al. 2005. Nature 436:1186-1190; Groh et al. 1996. Proc Natl Acad Sci USA 93:12445-12450; Yamamoto et al. 2001. Biochim Biophys Acta 1526:10-12). During tumor progression, however, most tumor cells eventually acquire various mechanisms such as ligand shedding and microRNA expression that downregulate the surface expression of NKG2DLs, resulting in immunosurveillance escape (Salih, et al. 2002. J Immunol 169:4098-4102; Stern-Ginossar et al. 2008. Nat Immunol 9:1065-1073). In colorectal carcinoma, high expression of NKG2DLs is frequently observed in early stages of tumor development. The ligand expression, however, progressively decreases in later stages of the disease, and this lower level of expression correlates with reduced subject survival (McGilvray et al. 2009. Clin Cancer Res 15:6993-7002). Therefore, studies are needed to elucidate the mechanism of NKG2DL regulation and to identify therapeutic drugs that can upregulate their expression.

SUMMARY OF INVENTION

There is a great need in the art for new effective methods for treating and/or preventing cancer. The present invention addresses these and other needs.

In one embodiment, the invention provides a method for treating or preventing cancer in a subject in need thereof, said method comprising administering to said subject a therapeutically effective amount of an RXR-gamma agonist of formula (I)

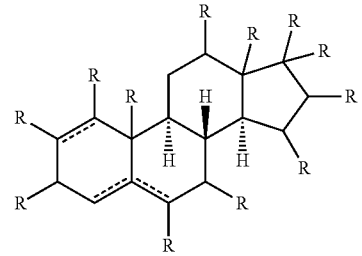

wherein, each of R is independently hydrogen, halogen, R*, —OH, =O, —NO$_2$, —CN, —OR$^\#$, —SR$^\#$, —N(R$^\#$)$_2$, —C(O)R$^\#$, —CO$_2$R$^\#$, —C(O)C(O)R$^\#$, —C(O)CH$_2$C(O)R$^\#$, —S(O)R$^\#$, —S(O)$_2$R$^\#$, —C(O)N(R$^\#$)$_2$, —SO$_2$N(R$^\#$)$_2$, —OC(O)R$^\#$, —N(R$^\#$)C(O)R$^\#$, —N(R$^\#$)N(R$^\#$)$_2$, —N(R$^\#$)C(=NR$^\#$)N(R$^\#$)$_2$, —C(=NR$^\#$)N(R$^\#$)$_2$, —C=NOR$^\#$, —N(R$^\#$)C(O)N(R$^\#$)$_2$, —N(R$^\#$)SO$_2$N(R$^\#$)$_2$, —N(R$^\#$)SO$_2$R$^\#$, —OC(O)N(R$^\#$)$_2$, or an optionally substituted C$_{1-12}$ aliphatic group, or two R groups are taken together with their intervening atoms to form an optionally substituted 3- to 7-membered ring having 0-4 heteroatoms selected from nitrogen, oxygen, or sulfur;

each R$^\#$ is independently hydrogen or R*;

each R* is independently an optionally substituted group selected from C$_{1-10}$ aliphatic, aryl, a 3-7 membered saturated or partially unsaturated carbocyclic ring, a 3-7 membered saturated or partially unsaturated monocyclic heterocyclic ring having 0-2 heteroatoms independently selected from nitrogen, oxygen, or sulfur, or a heteroaryl ring having 0-3 heteroatoms independently selected from nitrogen, oxygen, or sulfur; or: two R* groups on the same nitrogen are taken together with their intervening atoms to form an optionally substituted 3-7 membered saturated, partially unsaturated, or heteroaryl ring having 0-4 heteroatoms independently selected from nitrogen, oxygen, or sulfur, or an enantiomer, diastereomer, tautomer, solvate, prodrug or pharmaceutical acceptable salt thereof.

In another embodiment, the invention provides a method for enhancing cancer cell susceptibility to NK cell cytotoxicity in a subject having a cancer or a precancerous condition, said method comprising administering to said subject a therapeutically effective amount of an RXR-gamma agonist of formula (I)

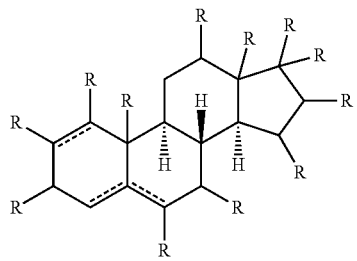

wherein,
each of R is independently hydrogen, halogen, R*, —OH, =O, —NO$_2$, —CN, —OR$^#$, —SR$^#$, —N(R$^#$)$_2$, —C(O)R$^#$, —CO$_2$R$^#$, —C(O)C(O)R$^#$, —C(O)CH$_2$C(O)R$^#$, —S(O)R$^#$, —S(O)$_2$R$^#$, —C(O)N(R$^#$)$_2$, —SO$_2$N(R$^#$)$_2$, —OC(O)R$^#$, —N(R$^#$)C(O)R$^#$, —N(R$^#$)N(R$^#$)$_2$, —N(R$^#$)C(=NR$^#$)N(R$^#$)$_2$, —C(=NR$^#$)N(R$^#$)$_2$, —C=NOR$^#$, —N(R$^#$)C(O)N(R$^#$)$_2$, —N(R$^#$)SO$_2$N(R$^#$)$_2$, —N(R$^#$)SO$_2$R$^#$, —OC(O)N(R$^#$)$_2$, or an optionally substituted C$_{1-12}$ aliphatic group, or two R groups are taken together with their intervening atoms to form an optionally substituted 3- to 7-membered ring having 0-4 heteroatoms selected from nitrogen, oxygen, or sulfur;
each R$^#$ is independently hydrogen or R*;
each R* is independently an optionally substituted group selected from C$_{1-10}$ aliphatic, aryl, a 3-7 membered saturated or partially unsaturated carbocyclic ring, a 3-7 membered saturated or partially unsaturated monocyclic heterocyclic ring having 0-2 heteroatoms independently selected from nitrogen, oxygen, or sulfur, or a heteroaryl ring having 0-3 heteroatoms independently selected from nitrogen, oxygen, or sulfur, or: two R* groups on the same nitrogen are taken together with their intervening atoms to form an optionally substituted 3-7 membered saturated, partially unsaturated, or heteroaryl ring having 0-4 heteroatoms independently selected from nitrogen, oxygen, or sulfur,
or an enantiomer, diastereomer, tautomer, solvate, prodrug or pharmaceutical acceptable salt thereof.

In a further embodiment, the invention provides a method for inhibiting cancer metastasis in a subject in need thereof, said method comprising administering to said subject a therapeutically effective amount of an RXR-gamma agonist of formula (I)

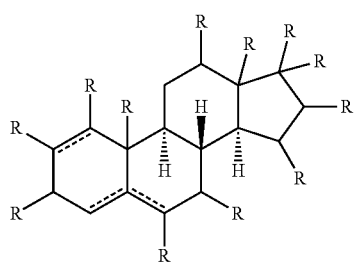

wherein,
each of R is independently hydrogen, halogen, R*, —OH, =O, —NO$_2$, —CN, —OR$^#$, —SR$^#$, —N(R$^#$)$_2$, —C(O)R$^#$, —CO$_2$R$^#$, —C(O)C(O)R$^#$, —C(O)CH$_2$C(O)R#, —S(O)R$^#$, —S(O)$_2$R$^#$, —C(O)N(R$^#$)$_2$, —SO$_2$N(R$^#$)$_2$, —OC(O)R$^#$, —N(R$^#$)C(O)R$^#$, —N(R$^#$)N(R$^#$)$_2$, —N(R$^#$)C(=NR$^#$)N(R$^#$)$_2$, —C(=NR$^#$)N(R$^#$)$_2$, —C=NOR$^#$, —N(R$^#$)C(O)N(R$^#$)$_2$, —N(R$^#$)SO$_2$N(R$^#$)$_2$, —N(R$^#$)SO$_2$R$^#$, —OC(O)N(R$^#$)$_2$, or an optionally substituted C$_{1-12}$ aliphatic group, or two R groups are taken together with their intervening atoms to form an optionally substituted 3- to 7-membered ring having 0-4 heteroatoms selected from nitrogen, oxygen, or sulfur;
each R$^#$ is independently hydrogen or R*;
each R* is independently an optionally substituted group selected from C$_{1-10}$ aliphatic, aryl, a 3-7 membered saturated or partially unsaturated carbocyclic ring, a 3-7 membered saturated or partially unsaturated monocyclic heterocyclic ring having 0-2 heteroatoms independently selected from nitrogen, oxygen, or sulfur, or a heteroaryl ring having 0-3 heteroatoms independently selected from nitrogen, oxygen, or sulfur; or: two R* groups on the same nitrogen are taken together with their intervening atoms to form an optionally substituted 3-7 membered saturated, partially unsaturated, or heteroaryl ring having 0-4 heteroatoms independently selected from nitrogen, oxygen, or sulfur,
or an enantiomer, diastereomer, tautomer, solvate, prodrug or pharmaceutical acceptable salt thereof.

In another embodiment, the invention provides a method for upregulating NKG2DL expression in a cancer cell comprising administering to said cell an effective amount of an RXR-gamma agonist of formula (I)

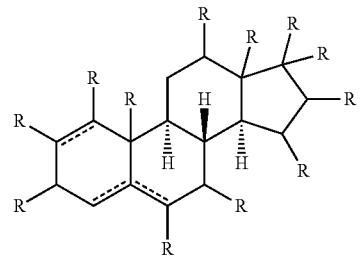

wherein,
each of R is independently hydrogen, halogen, R*, —OH, =O, —NO$_2$, —CN, —OR$^#$, —SR$^#$, —N(R$^#$)$_2$, —C(O)R$^#$, —CO$_2$R$^#$, —C(O)C(O)R$^#$, —C(O)CH$_2$C(O)R$^#$, —S(O)R$^#$, —S(O)$_2$R$^#$, —C(O)N(R$^#$)$_2$, —SO$_2$N(R$^#$)$_2$, —OC(O)R$^#$, —N(R$^#$)C(O)R$^#$, —N(R$^#$)N(R$^#$)$_2$, —N(R$^#$)C(=NR$^#$)N(R$^#$)$_2$, —C(=NR$^#$)N(R$^#$)$_2$, —C=NOR$^#$, —N(R$^#$)C(O)N(R$^#$)$_2$, —N(R$^#$)SO$_2$N(R$^#$)$_2$, —N(R$^#$)SO$_2$R$^#$, —OC(O)jN(R$^#$)$_2$, or an optionally substituted C$_{1-12}$ aliphatic group, or two R groups are taken together with their intervening atoms to form an optionally substituted 3- to 7-membered ring having 0-4 heteroatoms selected from nitrogen, oxygen, or sulfur;
each R$^#$ is independently hydrogen or R*;
each R* is independently an optionally substituted group selected from C$_{1-10}$ aliphatic, aryl, a 3-7 membered saturated or partially unsaturated carbocyclic ring, a 3-7 membered saturated or partially unsaturated monocyclic heterocyclic ring having 0-2 heteroatoms independently selected from nitrogen, oxygen, or sulfur, or a heteroaryl ring having 0-3 heteroatoms independently selected from nitrogen, oxygen, or sulfur, or: two R* groups on the same nitrogen are taken together with their intervening atoms to form an optionally substituted 3-7 membered saturated, partially unsaturated, or heteroaryl ring having 0-4 heteroatoms independently selected from nitrogen, oxygen, or sulfur,
or an enantiomer, diastereomer, tautomer, solvate, prodrug or pharmaceutical acceptable salt thereof.

In yet another embodiment, the invention provides a method for enhancing expression of TIMP2 and/or TIMP3 in a cancer cell comprising administering to said cell an effective amount of an RXR-gamma agonist of formula (I)

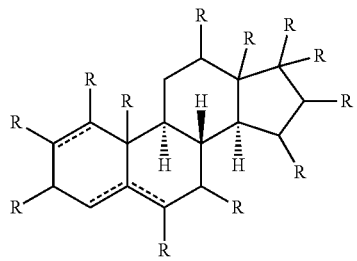

wherein,
each of R is independently hydrogen, halogen, R*, —OH, =O, —NO$_2$, —CN, —OR$^\#$, —SR$^\#$, —N(R$^\#$)$_2$, —C(O)R$^\#$, —CO$_2$R$^\#$, —C(O)C(O)R$^\#$, —C(O)CH$_2$C(O)R$^\#$, —S(O)R$^\#$, —S(O)$_2$R$^\#$, —C(O)N(R$^\#$)$_2$, —SO$_2$N(R$^\#$)$_2$, —OC(O)R$^\#$, —N(R$^\#$)C(O)R$^\#$, —N(R$^\#$)N(R$^\#$)$_2$, —N(R$^\#$)C(=NR$^\#$)N(R$^\#$)$_2$, —C(=NR$^\#$)N(R$^\#$)$_2$, —C=NOR$^\#$, —N(R$^\#$)C(O)N(R$^\#$)$_2$, —N(R$^\#$)SO$_2$N(R$^\#$)$_2$, —N(R$^\#$)SO$_2$R, —OC(O)N(R$^\#$)$_2$, or an optionally substituted C$_{1-12}$ aliphatic group, or two R groups are taken together with their intervening atoms to form an optionally substituted 3- to 7-membered ring having 0-4 heteroatoms selected from nitrogen, oxygen, or sulfur;
each R# is independently hydrogen or R*;
each R* is independently an optionally substituted group selected from C$_{1-10}$ aliphatic, aryl, a 3-7 membered saturated or partially unsaturated carbocyclic ring, a 3-7 membered saturated or partially unsaturated monocyclic heterocyclic ring having 0-2 heteroatoms independently selected from nitrogen, oxygen, or sulfur, or a heteroaryl ring having 0-3 heteroatoms independently selected from nitrogen, oxygen, or sulfur; or: two R* groups on the same nitrogen are taken together with their intervening atoms to form an optionally substituted 3-7 membered saturated, partially unsaturated, or heteroaryl ring having 0-4 heteroatoms independently selected from nitrogen, oxygen, or sulfur,
or an enantiomer, diastereomer, tautomer, solvate, prodrug or pharmaceutical acceptable salt thereof.

In a further embodiment, the invention provides a method for suppressing motility and invasiveness of a cancer cell comprising administering to said cell an effective amount of an RXR-gamma agonist of formula (I)

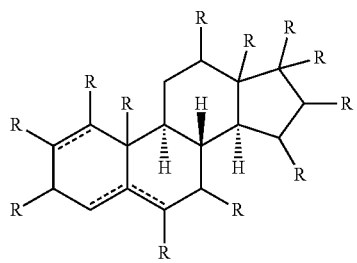

wherein,
each of R is independently hydrogen, halogen, R*, —OH, =O, —NO$_2$, —CN, —OR$^\#$, —SR$^\#$, —N(R$^\#$)$_2$, —C(O)R$^\#$, —CO$_2$R$^\#$, —C(O)C(O)R$^\#$, —C(O)CH$_2$C(O)R$^\#$, —S(O)R$^\#$, —S(O)$_2$R$^\#$, —C(O)N(R$^\#$)$_2$, —SO$_2$N(R$^\#$)$_2$, —OC(O)R$^\#$, —N(R$^\#$)C(O)R$^\#$, —N(R$^\#$)N(R$^\#$)$_2$, —N(R$^\#$)C(=NR$^\#$)N(R$^\#$)$_2$, —C(=NR$^\#$)N(R$^\#$)$_2$, —C=NOR$^\#$, —N(R$^\#$)C(O)N(R$^\#$)$_2$, —N(R$^\#$)SO$_2$N(R$^\#$)$_2$, —N(R$^\#$)SO$_2$R$^\#$, —OC(O)N(R$^\#$)$_2$, or an optionally substituted C$_{1-12}$ aliphatic group, or two R groups are taken together with their intervening atoms to form an optionally substituted 3- to 7-membered ring having 0-4 heteroatoms selected from nitrogen, oxygen, or sulfur;
each R# is independently hydrogen or R*;
each R* is independently an optionally substituted group selected from C$_{1-10}$ aliphatic, aryl, a 3-7 membered saturated or partially unsaturated carbocyclic ring, a 3-7 membered saturated or partially unsaturated monocyclic heterocyclic ring having 0-2 heteroatoms independently selected from nitrogen, oxygen, or sulfur, or a heteroaryl ring having 0-3 heteroatoms independently selected from nitrogen, oxygen, or sulfur; or: two R* groups on the same nitrogen are taken together with their intervening atoms to form an optionally substituted 3-7 membered saturated, partially unsaturated, or heteroaryl ring having 0-4 heteroatoms independently selected from nitrogen, oxygen, or sulfur,
or an enantiomer, diastereomer, tautomer, solvate, prodrug or pharmaceutical acceptable salt thereof.

In another embodiment, the invention provides a method for inhibiting expression of one or more Matrix Metalloproteinases (MMPs), in a cancer cell comprising administering to said cell an effective amount of an RXR-gamma agonist of formula (I)

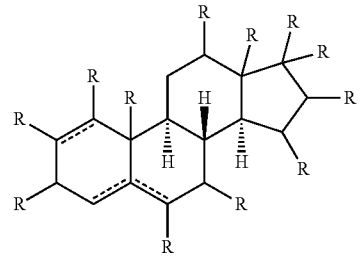

wherein,
each of R is independently hydrogen, halogen, R*, —OH, =O, —NO$_2$, —CN, —OR$^\#$, —SR$^\#$, —N(R$^\#$)$_2$, —C(O)R$^\#$, —CO$_2$R$^\#$, —C(O)C(O)R$^\#$, —C(O)CH$_2$C(O)R#, —S(O)R$^\#$, —S(O)$_2$R$^\#$, —C(O)N(R$^\#$)$_2$, —SO$_2$N(R$^\#$)$_2$, —OC(O)R$^\#$, —N(R$^\#$)C(O)R$^\#$, —N(R$^\#$)N(R$^\#$)$_2$, —N(R$^\#$)C(=NR$^\#$)N(R$^\#$)$_2$, —C(=NR$^\#$)N(R$^\#$)$_2$, —C=NOR$^\#$, —N(R$^\#$)C(O)N(R$^\#$)$_2$, —N(R$^\#$)SO$_2$N(R$^\#$)$_2$, —N(R$^\#$)SO$_2$R$^\#$, —OC(O)N(R$^\#$)$_2$, or an optionally substituted C$_{1-12}$ aliphatic group, or two R groups are taken together with their intervening atoms to form an optionally substituted 3- to 7-membered ring having 0-4 heteroatoms selected from nitrogen, oxygen, or sulfur;
each R# is independently hydrogen or R*;
each R* is independently an optionally substituted group selected from C$_{1-10}$ aliphatic, aryl, a 3-7 membered saturated or partially unsaturated carbocyclic ring, a 3-7 membered saturated or partially unsaturated monocyclic heterocyclic ring having 0-2 heteroatoms independently selected from nitrogen, oxygen, or sulfur, or a heteroaryl ring having 0-3 heteroatoms independently selected from nitrogen, oxygen, or sulfur; or: two R* groups on the same nitrogen are taken together with their intervening atoms to form an optionally substituted 3-7 membered saturated, partially unsaturated, or heteroaryl ring having 0-4 heteroatoms independently selected from nitrogen, oxygen, or sulfur,
or an enantiomer, diastereomer, tautomer, solvate, prodrug or pharmaceutical acceptable salt thereof.

In one specific embodiment, MMP expression in said cancer cell is higher than in a corresponding normal cell. In one specific embodiment, said one or more MMPs are selected from the group consisting of MMP-1, MMP-7, MMP-10, MMP-12 and MMP-13.

In one embodiment of any of the above methods, each of R within formula (I) is independently selected from a substituted or unsubstituted nitrogen, oxygen or sulfur, such as, for example, any of structures (a)-(f), or a =O, or a group (g):

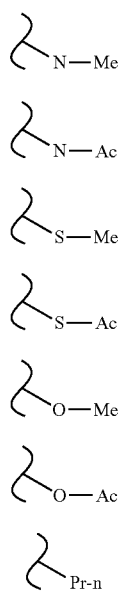

In one embodiment of any of the above methods, two R groups are taken together with their intervening atoms to form an optionally substituted group selected from heterocyclic lactone, lactam, lactim, or lactide, or a 3-7 membered saturated or partially unsaturated carbocyclic ring, or a 3-7 membered saturated or partially unsaturated monocyclic heterocyclic ring having 0-2 heteroatoms independently selected from nitrogen, oxygen, or sulfur, or a 5-6 membered heteroaryl ring having 0-3 heteroatoms independently selected from nitrogen, oxygen, or sulfur, or two R groups on the same nitrogen taken together with their intervening atoms to form an optionally substituted 3-7 membered saturated, partially unsaturated, or heteroaryl ring having 0-4 heteroatoms independently selected from nitrogen, oxygen, or sulfur.

In one embodiment of any of the above methods, two R groups are taken together with their intervening atoms to form an optionally substituted group selected from the following (h)-(l):

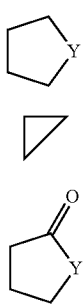

wherein Y can be N, O, S, S=O, or $SO_2$, preferably N or O, more preferably O.

In one embodiment of any of the above methods, the RXR-gamma agonist is a compound of formula (II)

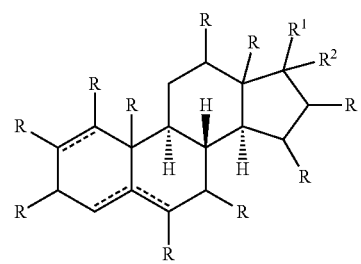

wherein R is as defined above, $R^1$ and $R^2$ taken together with the carbon to which they are attached form a ring (h), (j), (k) or (l), as disclosed above, with Y being O, and $R^3$ a substituted or unsubstituted nitrogen, oxygen or sulfur, such as, for example, any of structures (a)-(f), or a =O.

In one embodiment of any of the above methods, the RXR-gamma agonist is a compound of formula (III)

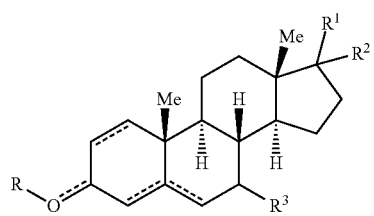

wherein R is as defined above, $R^1$ and $R^2$ taken together with the carbon to which they are attached form a ring (h), (j), (k) or (l), as disclosed above, with Y being O, and $R^3$ a substituted or unsubstituted nitrogen, oxygen or sulfur, such as, for example, any of structures (a)-(f), or a =O.

In one embodiment of any of the above methods, the RXR-gamma agonist is a compound of formula (IV):

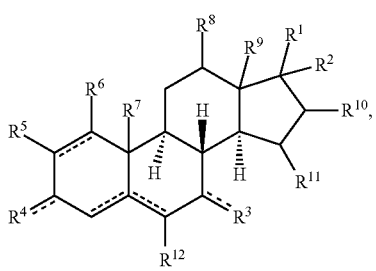

wherein:
----- is an optional double bond;
$R^1$ and $R^2$ together with the atom to which they are attached form a 3-, 4-, 5- or 6-membered heterocycloalkyl group;

$R^3$ is H; $SR^a$; O; $C_{1-6}$alkyl;
$R^4$ is O; $OR^b$;
$R^5$, $R^6$, $R^7$, $R^8$, $R^9$, $R^{10}$, and $R^{11}$ are each, independently, H or $C_{1-6}$alkyl;
or $R^{10}$ and $R^{11}$ together with the atoms from which they are attached form a 3-, 4-, or 5-membered cycloalkyl group;
$R^{12}$ is H or $OR^e$;
or $R^3$ and $R^{12}$ together with the atoms from which they are attached form a 3-, 4-, or 5-membered cycloalkyl group; and
$R^a$, $R^b$, and $R^c$ are each, independently, H; $C_{1-6}$alkyl; $C(O)C_{1-6}$alkyl.

In one embodiment of any of the above methods, the compound of formula (I) is selected from compounds 1-20:

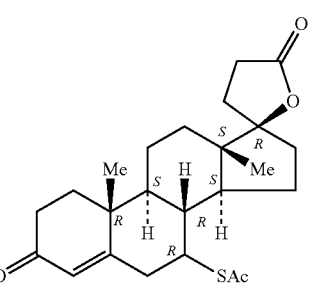

Absolute stereochemistry.
CAS (52-01-7) Spironolactone (1)

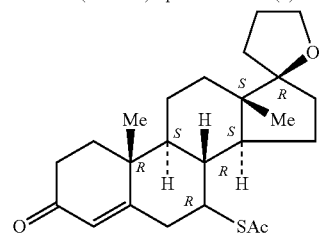

Absolute stereochemistry.
(6673-97-8) SPIROXASONE (2)

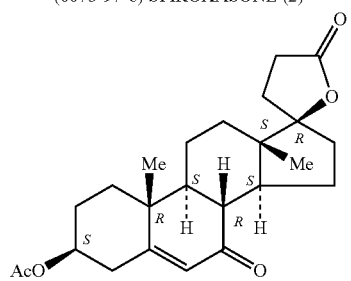

Absolute stereochemistry.
(30597-62-7) 7-Ketoandrenolactone acetate (3)

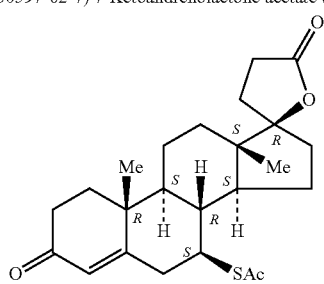

Absolute stereochemistry.
(33784-05-3) 7-β-Spironolactone (4)

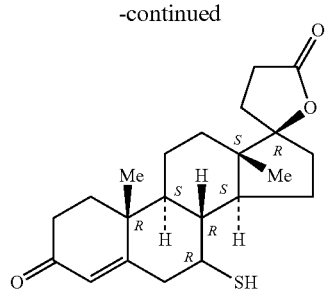

Absolute stereochemistry.
(38753-76-3) Deacetylspironolactone (5)

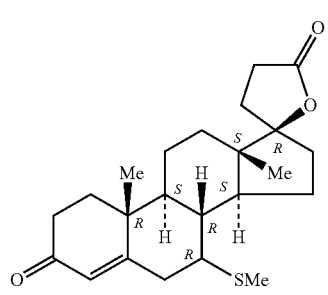

Absolute stereochemistry.
(38753-77-4) 7-α-(Thiomethyl)spirolactone (6)

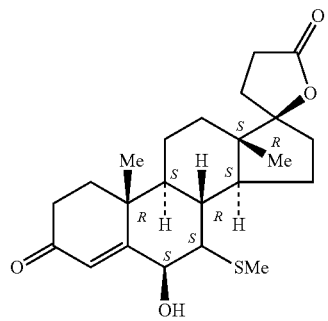

Absolute stereochemistry.
(42219-60-3) 6β-Hydroxy-7α-(thiomethyl)spirolactone (7)

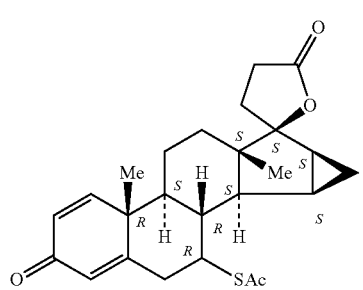

Absolute stereochemistry.
(87952-98-5) Mespirenone (8)

-continued

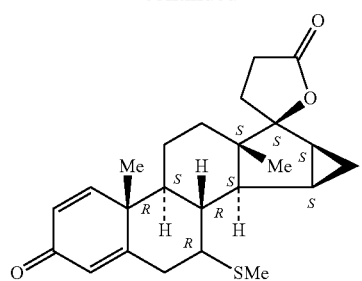

Absolute stereochemistry.
(97870-25-2) ZK 97894 (9)

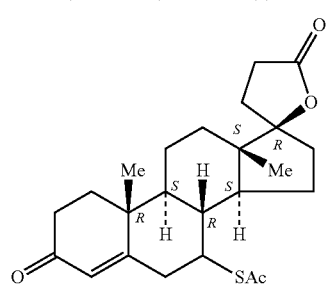

Absolute stereochemistry.
(244290-14-0) 17α-Pregn-4-ene-21-carboxylic acid, 17-hydroxy-7-mercapto-3-oxo-, γ-lactone acetate (10)

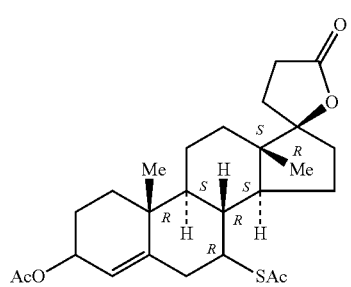

Absolute stereochemistry.
(452920-31-9) (11)

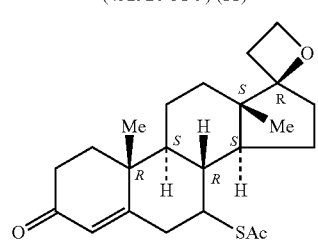

Absolute stereochemistry.
(1260150-03-5) (12)

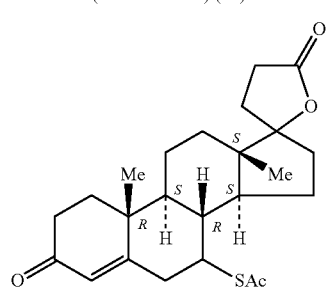

Absolute stereochemistry.
(1301717-71-4) (13)

-continued

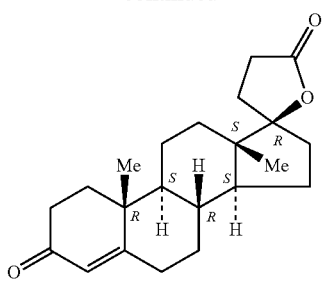

Absolute stereochemistry.
(976-70-5) 6,7-Dihydrocanrenone (14)

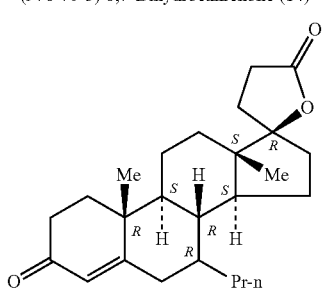

Absolute stereochemistry.
(76676-33-0) RU 26752 (15)

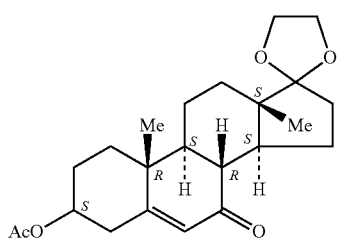

Absolute stereochemistry., Rotation (-).
(40573-86-2) 3β-Acetoxy-17-ethylenedioxy-5-androsten-7-one (16)

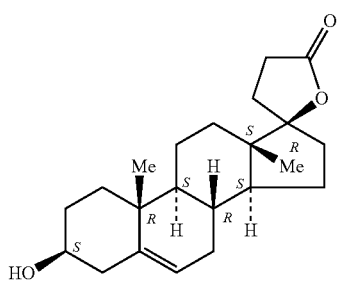

Absolute stereochemistry., Rotation (-).
(13934-61-7) Andrenolactone (17)

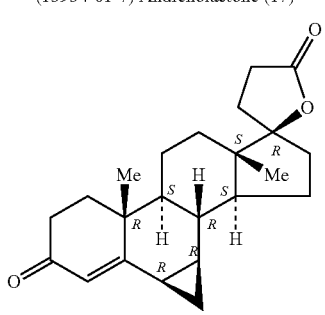

Absolute stereochemistry.
(40574-52-5) Prorenone (18)

-continued

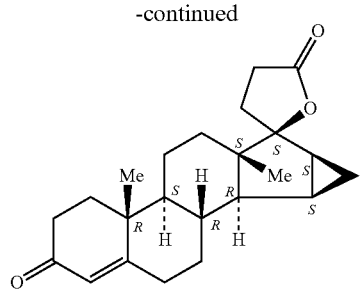

Absolute stereochemistry.
(67372-68-3) 6,7-Desmethylenedrospirenone (19)

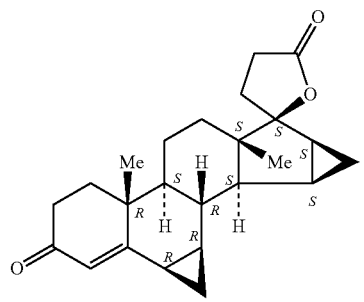

Absolute stereochemistry., Rotation (-).
(67392-87-4) Dihydrospirorenone (20)

or an enantiomer, diastereomer, tautomer, solvate, prodrug or pharmaceutical acceptable salt thereof.

In one embodiment of any of the above methods, the compound of formula (I) is

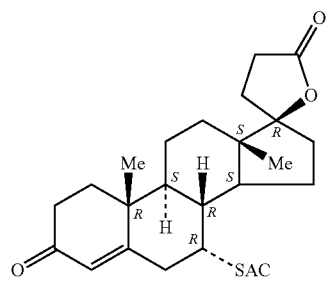

Absolute stereochemistry.
CAS (52-01-7) Spironolactone (1)

or an enantiomer, diastereomer, tautomer, solvate, prodrug or pharmaceutical acceptable salt thereof.

In a separate embodiment, the invention provides a method for treating cancer in a subject in need thereof, said method comprising administering to said subject a therapeutically effective amount of an antagonist of RXR-alpha.

In a further embodiment, the invention provides a method for enhancing cancer cell susceptibility to NK cell cytotoxicity in a subject having a cancer or a precancerous condition, said method comprising administering to said subject a therapeutically effective amount of an antagonist of RXR-alpha.

In a preferred embodiment of the above methods involving an antagonist of RXR-alpha, said antagonist of RXR-alpha said antagonist of RXR-alpha does not inhibit RXR-gamma.

In one embodiment of the above methods involving an antagonist of RXR-alpha, said antagonist of RXR-alpha is siRNA. In one specific embodiment, said siRNA comprises the sequence GGGAGAAGGUCUAUGCGUC (SEQ ID NO: 1). In one specific embodiment, said siRNA consists of the sequence GGGAGAAGGUCUAUGCGUC (SEQ ID NO: 1).

In one embodiment of the above methods involving an antagonist of RXR-alpha, said antagonist of RXR-alpha is an antibody.

In one embodiment of the above methods involving a cancer cell, said cancer cell is in a subject. In one embodiment of the above methods involving a cancer cell, is characterized by a decreased NKG2DL expression, as compared to a corresponding normal cell.

In one embodiment of any of the above methods, the cancer is selected from the group consisting of colorectal cancer, head and neck cancer, prostate cancer, hepatocellular carcinoma, rhabdomyosarcoma, hepatocellular adenoma, cholangiocarcinoma, colorectal adenoma, ileal adenoma, renal cancer, oesophageal cancer, gastric cancer, breast cancer, and esophageal cancer.

In one embodiment of any of the above methods, the subject is human. In another embodiment of any of the above methods, the subject is an experimental animal model of a cancer.

These and other aspects of the present invention will be apparent to those of ordinary skill in the art in the following description, claims and drawings.

BRIEF DESCRIPTION OF THE DRAWINGS

FIG. 2 demonstrates that SPIR enhances tumor cell sensitivity to NK cell killing. (A) NKL cells express high level of NKG2D but not NKp30 on their cell surface as determined by flow cytometry. Results are representative of two independent experiments. Therefore, the use of anti-NKp30 in NKL killing assay described in 2 F below was considered as a non-specific IgG blockade relative to anti-NKG2D. (B) NK cell cytotoxicity on the colon cancer cell lines treated with DMSO or SPIR (56 µM) for 3 days was determined by a BATDA release assay using NKL cells as effector cells (n=3). (C) NK cell cytotoxicity on HT29 and SW480 cells treated with DMSO or SPIR (56 µM) for 3 days was determined by a BATDA release assay using IL-2 (10 U/ml)-primed primary NK cells isolated from healthy donors at various E:T ratios (n=3). (D) HCT116 cells transduced with control or a ULBP2-overexpressing lentiviral construct were analyzed by flow cytometry for the surface expression of ULBP2. Results are representative of two independent experiments. (E) NK cell cytotoxicity on the ULBP2-transduced HCT116 cells was determined by a BATDA release assay using NKL cells as effector cells (n=3). (F) DMSO- or SPIR-treated (3 days) HCT116 cells were subjected to a BATDA release assay using NKL cells in the presence or absence of anti-NKp30 or anti-NKG2D antibodies (10 µg/mL) (n=3). (G) DMSO- or SPIR-treated (3 days) HCT116 cells were subjected to a BATDA release assay using IL-2 (10 U/ml)-primed primary NK cells isolated from healthy donors at various E:T ratios in the presence or absence of anti-NKp30 or anti-NKG2D antibodies (10 µg/mL) (n=3). * $P<0.05$,  $P<0.005$, * $P<0.0001$.

every other day for three times. HCT116 xenograft growth was analyzed by performing bioluminescence imaging on day 10. * P<0.05, ** P<0.0001.

Figure 6:
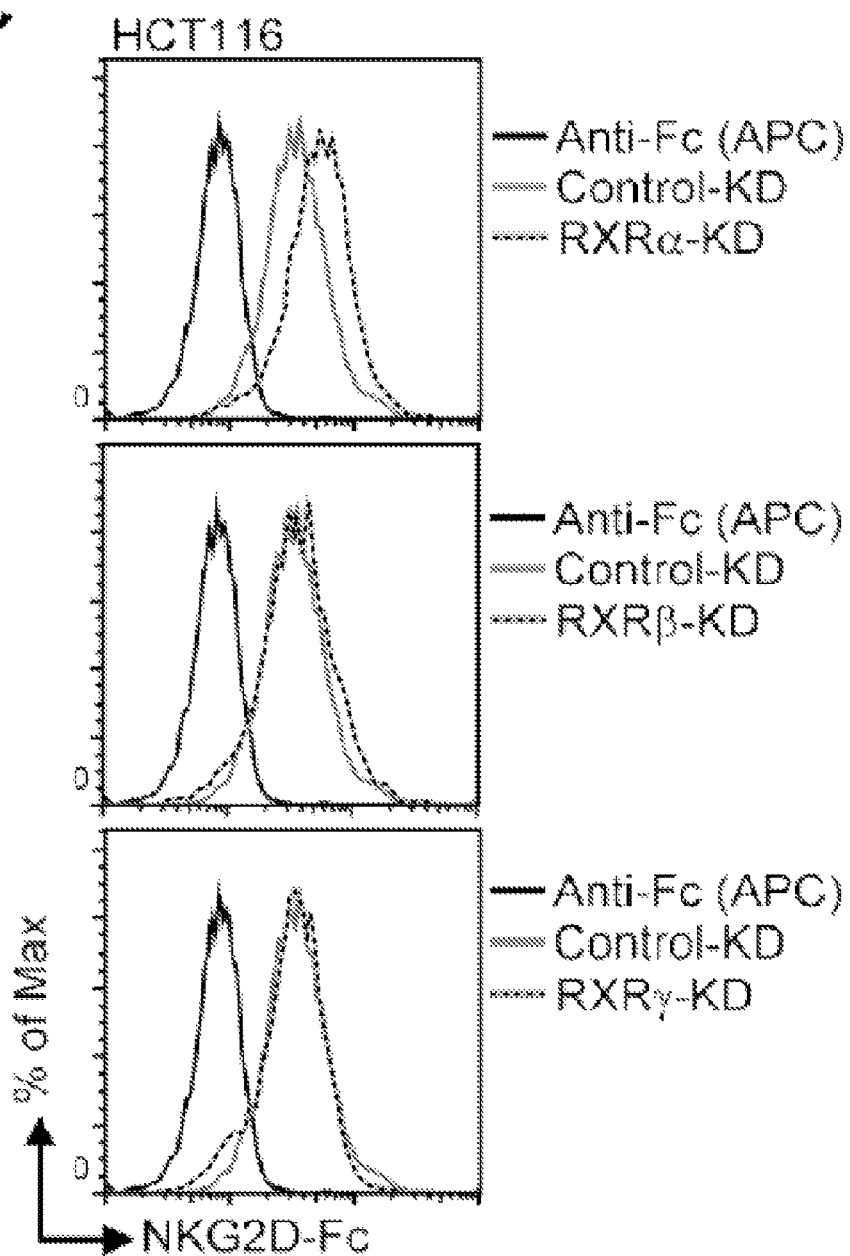

FIG. 6 demonstrates that 9-cis-retinoic acid treatment reduces NKG2DL expression while specific siRNA knockdown of RXR-alpha upregulates NKG2DL expression. (A) Total NKG2DL expression was analyzed in HCT116 cells treated with DMSO or 9-cis-RA (40 µM) for 3 days by flow cytometry. Results are representative of three independent experiments. (B) HCT116 cells were transfected with control-KD or RXR-alpha-KD siRNAs 48 h before treatment with DMSO or SPIR (56 µM). The expression of total NKG2DLs was analyzed by flow cytometry 3 days after the drug treatment. Results are representative of three independent experiments. (C) Total NKG2DL expression was analyzed in HCT116 cells 48 h after transfected with specific siRNAs targeting RXR-alpha, RXRβ or RXR-gamma. Results are representative of three independent experiments. (D) MICA-B and ULBP1-3 expression were analyzed in HCT116 cells transfected with control-KD or RXR-alpha-KD siRNAs after DMSO or SPIR treatment for 3 days. Results are representative of three independent experiments. (E) HCT116 cells were transfected with control, RXR-alpha, RXRβ or RXR-gamma specific siRNAs 48 h before treatment with DMSO or 9-cis-RA (40 µM). The expression of total NKG2DLs was analyzed by flow cytometry 3 days after the drug treatment. Results are representative of three independent experiments.

Figure 7:
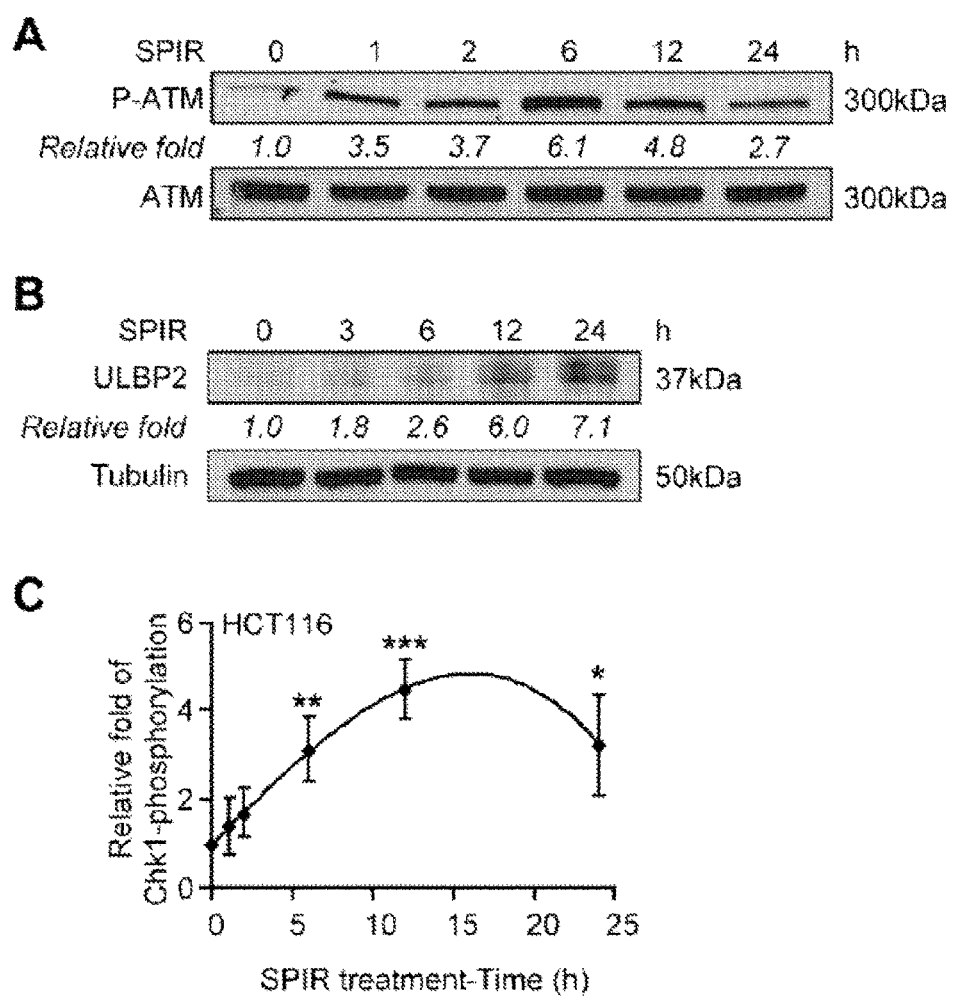
Figure 7:
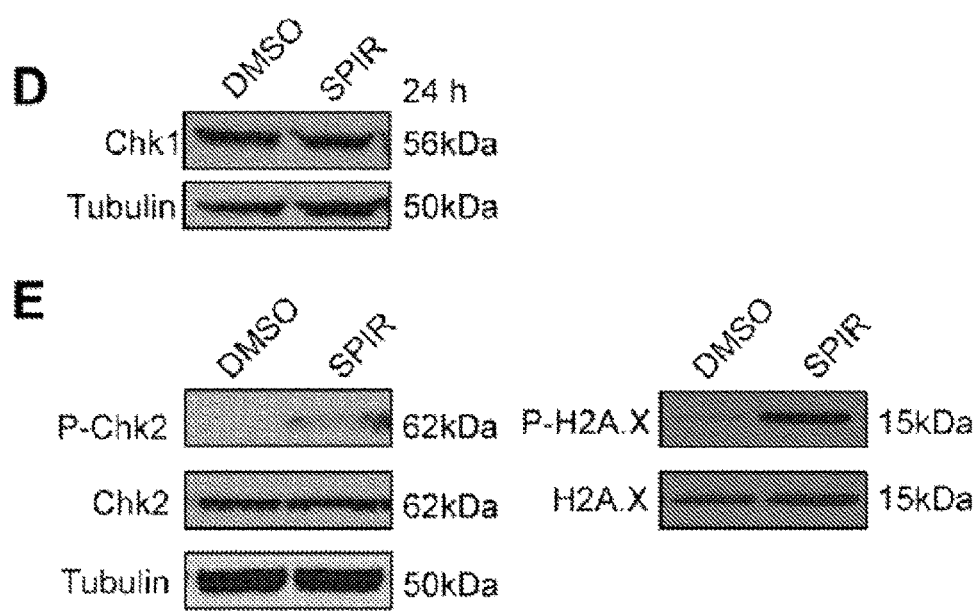
Figure 7:
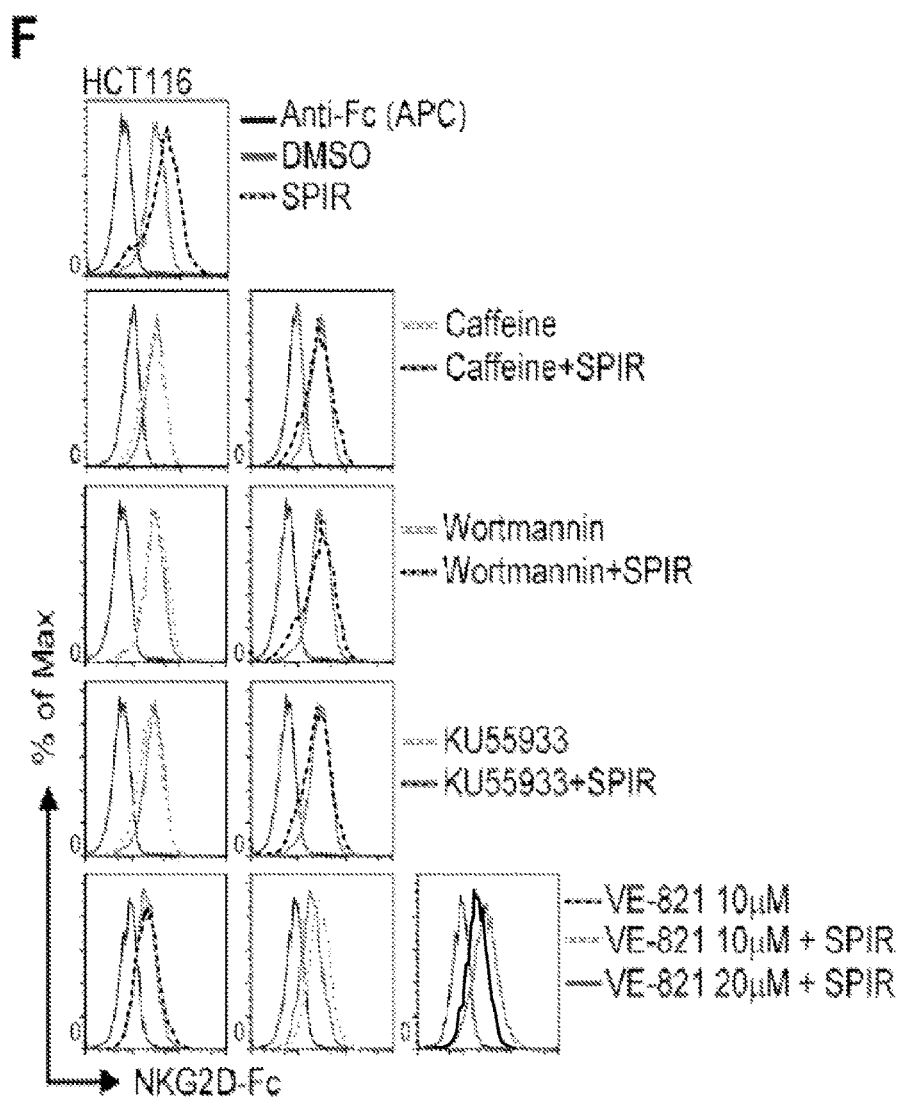
Figure 7:
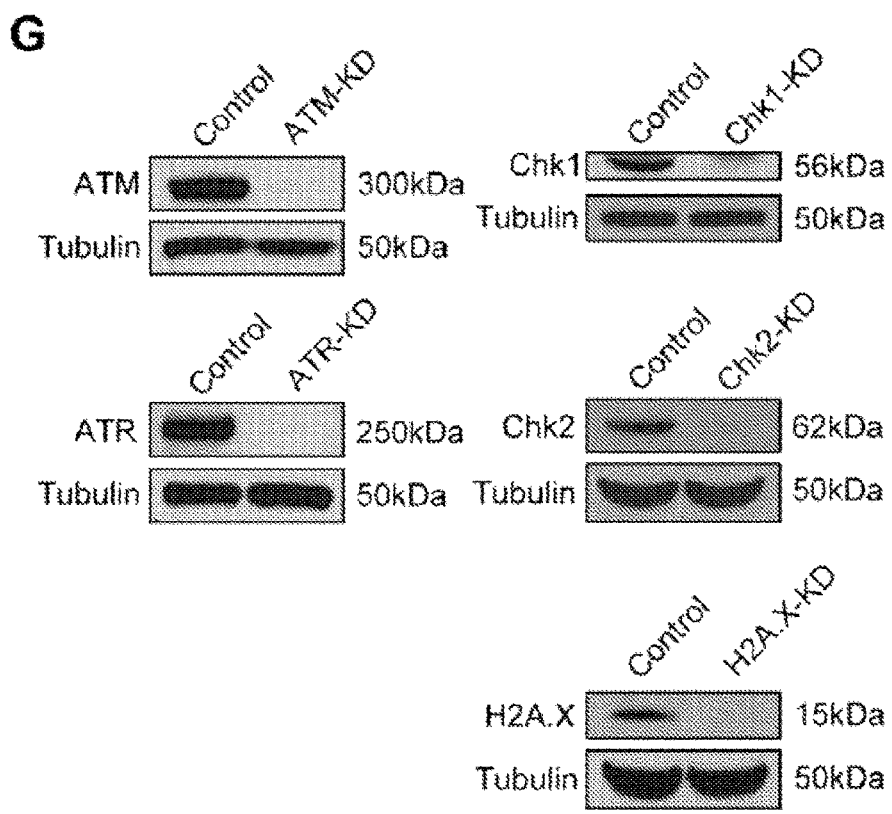
Figure 7:
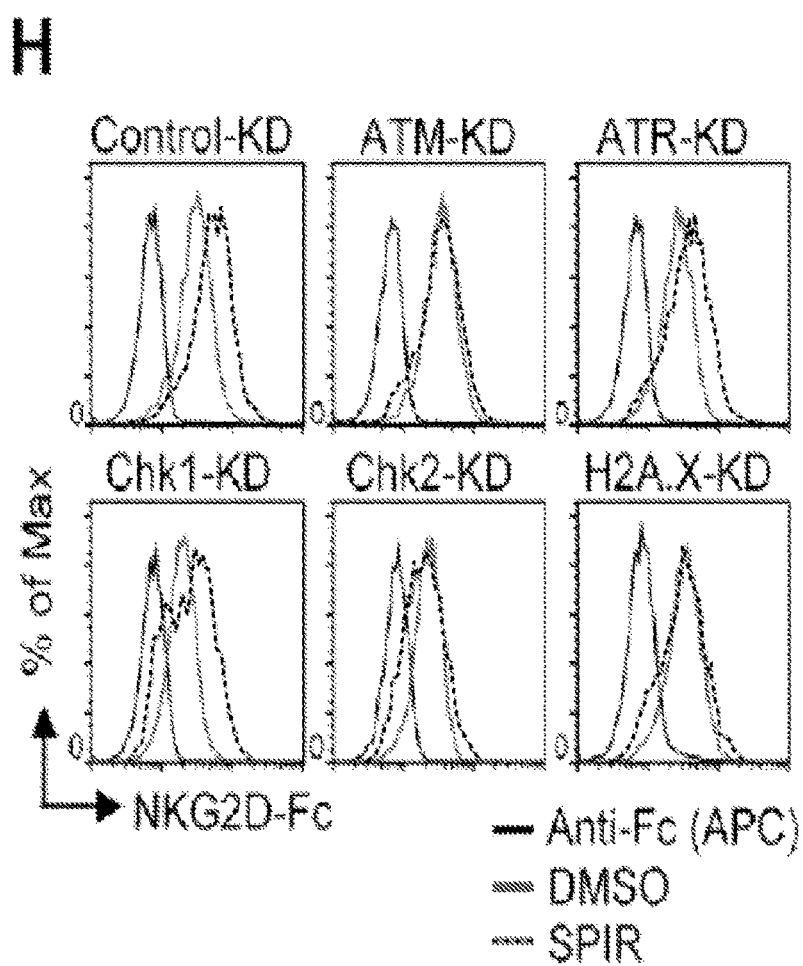

FIG. 7 demonstrates that the upregulation of NKG2DLs by SPIR requires activation of the ATM-Chk2 signaling pathway. HCT116 cells were treated with SPIR (56 µM). Total cell lysates were collected at various time points for Western blot analysis to detect (A) ATM (Ser1981) and ATR (Ser428) phosphorylation and (B) ULBP2 expression. Data shown are representative of three independent experiments. (C) HCT116 cells were cultured with SPIR (56 µM). Total cell lysates were prepared at various time points (with the same total protein concentration as determined by BCA protein assay) (0 h to 24 h) for phospho-Chk1 by ELISA. Data were expressed as fold change relative to the degree of Chk1 phosphorylation at 0 h (n=3). (D) The protein level of Chk1 upon SPIR treatment for 24 h was determined by Western blot analysis. Data are representative of three independent experiments. (E) Phosphorylation of Chk2 (Thr68), and histone H2A.X (Ser139) in HCT116 cells treated with DMSO or SPIR for 24 h were determined by Western blot analysis. Data are representative of three independent experiments. (F) NKG2DL expression was analyzed in HCT116 cells treated with SPIR (56 µM), with or without caffeine (1.5 mM), wortmannin (10 µM), KU55933 (10 µM) or VE-821 (10 and 20 µM) for 3 days. Data shown are representative of three independent experiments. (G) The knockdown efficiencies of various siRNAs in HCT116 cells were evaluated by Western blot analysis. Results are representative of three independent experiments. (H) NKG2DL expression was analyzed in HCT116 cells transfected with various siRNAs after DMSO or SPIR treatment for 3 days. Data shown are representative of three independent experiments. * P<0.05,  P<0.01, * P<0.001.

Figure 8:
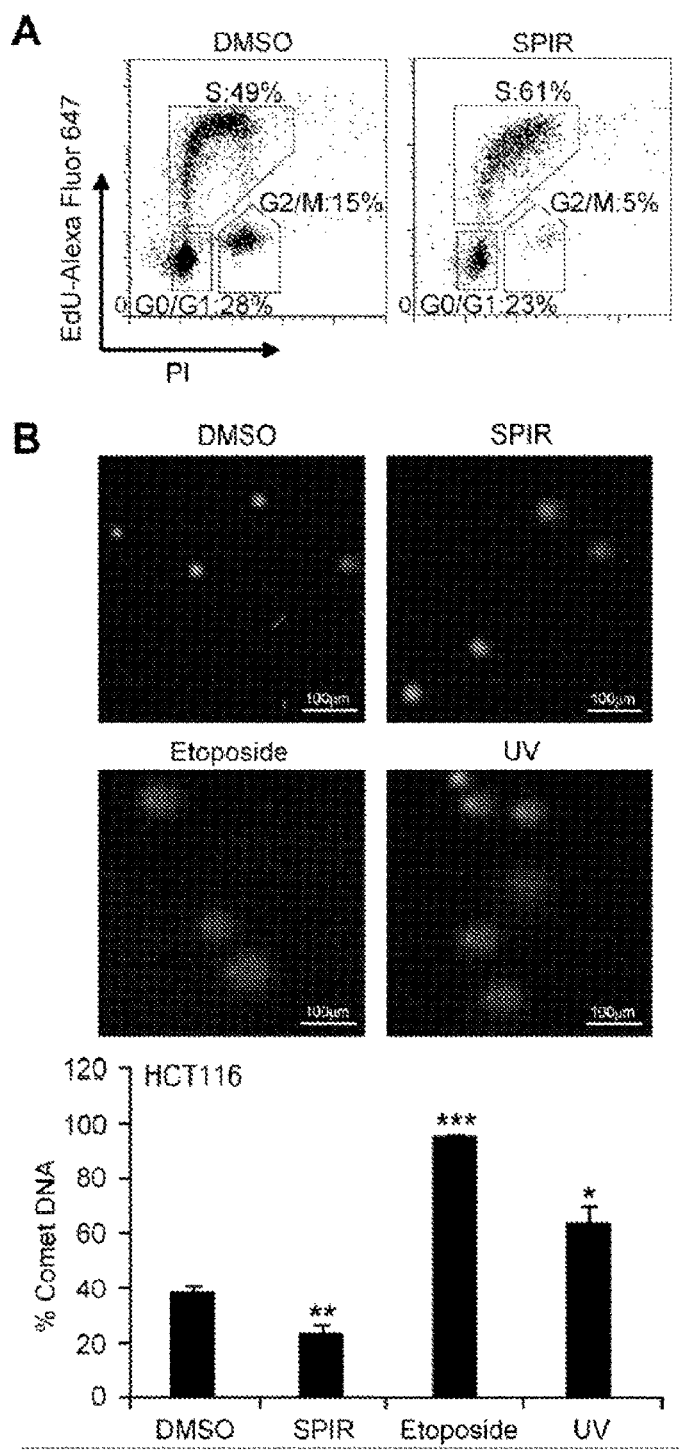
Figure 8:
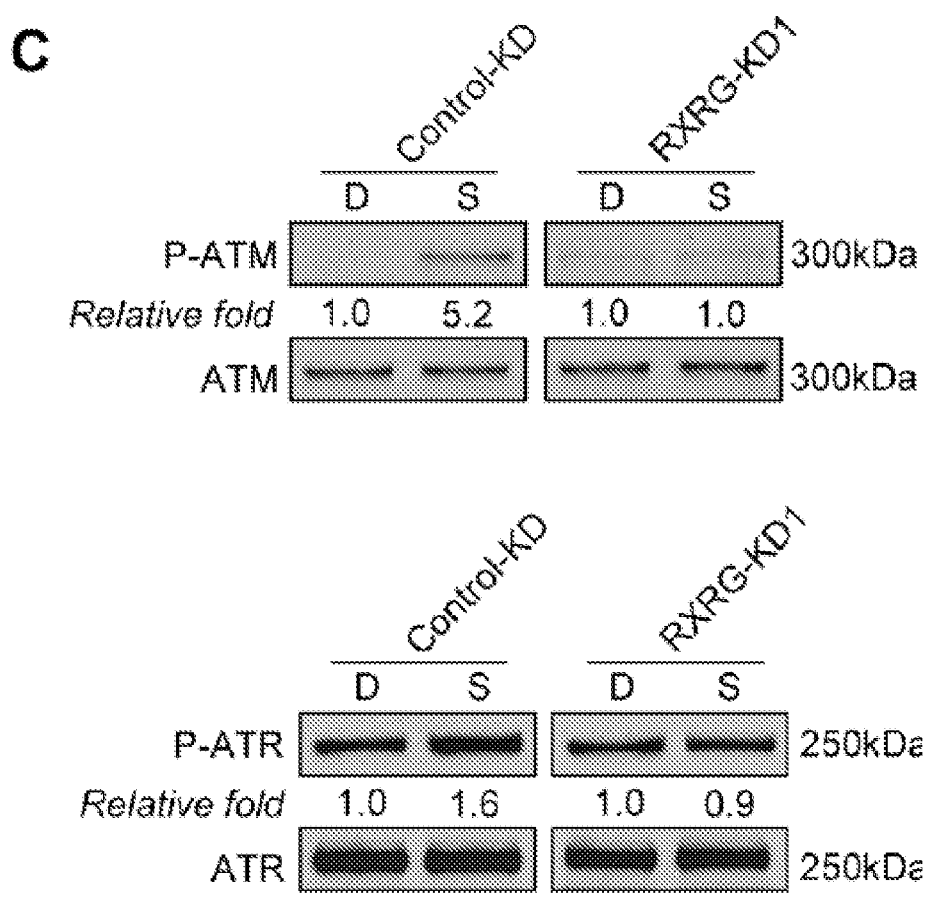

FIG. 8 demonstrates that SPIR does not induce DNA damage, and its activation of the ATM/ATR pathway requires the activation of RXR-gamma. (A) Cell-cycle analysis of HCT116 cells after DMSO or SPIR treatment for 24 h was performed by staining the cells with propidium iodide and EdU-Alexa Fluor 647. Data shown are representative of three independent experiments. (B) DNA damage in HCT116 cells after treatment with SPIR (56 µM for 24 h), etoposide (20 µM for 24 h), or UV exposure (4 h) was analyzed by performing comet assays (n=3). (C) HCT116 cells were transfected with control-KD or RXR-gamma-KD1 siRNA on day 0. Transfected cells were treated with DMSO or SPIR (56 µM) on day 2. Total cell lysates were collected 6 h after the drug treatment for Western blot analysis to detect phosphorylated ATM and ATR, or (D) 24 h after the drug treatment for ELISA to detect phosphorylated Chk1, and for (E) Western blot analysis to detect ULBP2 expression and phosphorylated Chk2 and H2A.X. Data shown are representative of three independent experiments. * P<0.05,  P<0.01, * P<0.0001.

Figure 9:
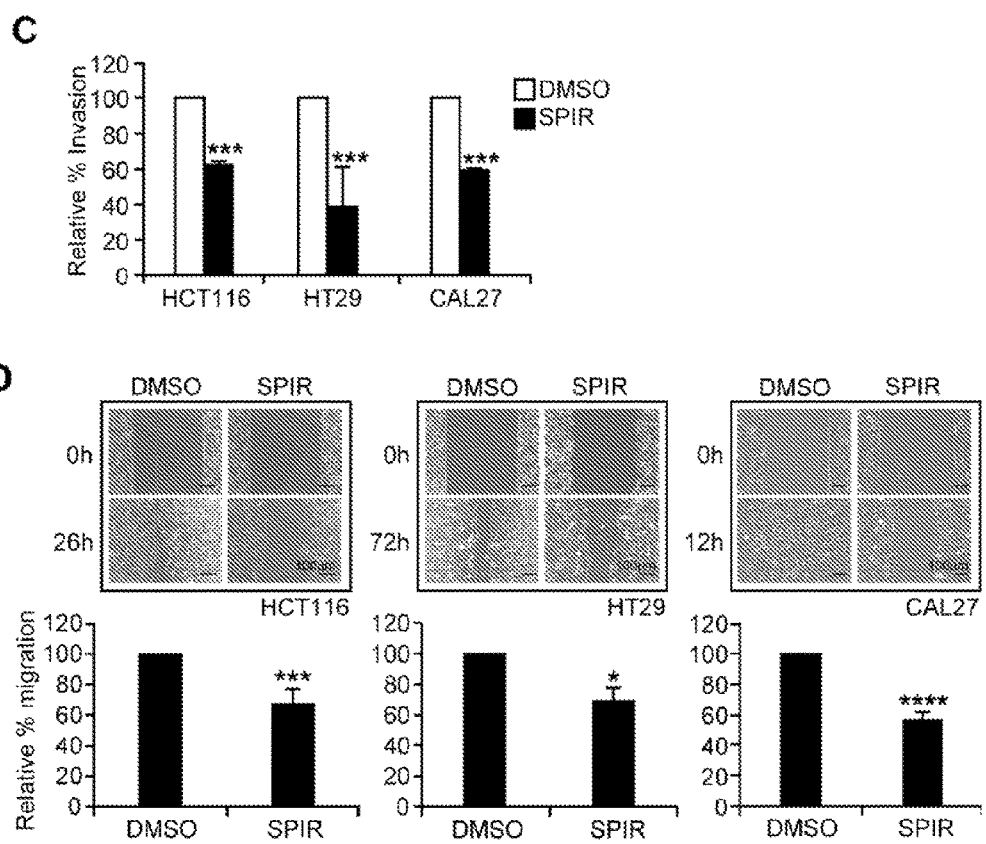

FIG. 9 demonstrates that SPIR inhibits tumor metastasis. (A) qRT-PCR was performed to analyze the mRNA expression of TIMP2 and TIMP3 in HCT116, HT29, and CAL27 cells treated with DMSO or SPIR (56 µM) for 3 days (n=3). (B) The protein level of TIMP2 and TIMP3 in the culture supernatant of HCT116 cells treated for 3 days with DMSO or SPIR (56 µM) was detected by ELISA (n=3). (C) Extracellular matrix (ECM) invasion assays were performed by culturing HCT116, HT29, and CAL27 cells on ECM-coated Transwell membranes with DMSO or SPIR. The number of cells that invaded the ECM was determined after 24 h. Data are expressed as percentage change in tumor invasion relative to that of DMSO-treated cells (n=3). (D) Wound healing by DMSO- and SPIR-treated HCT116, HT29, and CAL27 cells was compared. Data are calculated as the percentage change in distance of migration relative to that of DMSO-treated cells (n=3). (E) NSG mice (n=8) given subcutaneous injections (Day 0) of luciferase-expressing HT29 cells ($1\times10^7$) were treated with PBS or SPIR (1.25 mg) (intraperitoneally) twice a week for 3 weeks. Tumor xenografts and lung metastases were detected by bioluminescence imaging on day 25. Data are shown as the average total flux (photons/second)±standard deviation (n=8). (F) The lung metastases (arrows) were confirmed by examining lung tissue sections. * P≤0.05,  P<0.01, * P<0.005, **** P<0.0001.

FIG. 10 demonstrates that the antimetastatic effect of SPIR is independent of MR but requires the activation of RXR-gamma. (A) TIMP2 mRNA expression was compared by qRT-PCR on HCT116 cells treated with DMSO, SPIR, canrenone, or eplerenone for 3 days (n=3). (B) HCT116 cells were transfected with control KD or RXR-gamma-KD1 siRNA on day 0. The cells were treated with DMSO or SPIR (56 µM) on day 2. The mRNA expression of TIMP2 and TIMP3 was analyzed by qRT-PCR on day 5. Data are shown as relative mRNA fold change of SPIR-treated RXR-gamma-KD1 cells to control KD cells (n=3). (C) HCT116 cells were transfected with control KD or RXR-gamma-KD1 siRNA on day 0. Wound healing assay on the cells treated with DMSO or SPIR (56 µM) was performed on day 2. Data are calculated as the percentage change in distance of migration relative to that of DMSO-treated cells (n=3). (D) HCT116 cells were transfected with control KD, RXR-gamma-KD1, TIMP2-KD or TIMP3-KD siRNA on day 0. Transfected cells were cultured on ECM-coated Transwell membranes with DMSO or SPIR on day 2. The number of cells that invaded the ECM was determined after 36 h. Data are expressed as percentage change in tumor invasion relative to that of DMSO-treated cells (n=3). (E) HCT116 cells were transfected with control-KD, TIMP2-KD or TIMP3-KD siRNA on day 0. Wound healing assay on the cells treated with DMSO or SPIR (56 µM) was performed on day 2 (n=3). (F) Luciferase-expressing HCT116 cells were transfected with either control-KD or RXR-gamma-KD1 siRNA on Day 0. The transfected cells were collected on the next day to inject ($5 \times 10^5$ cells/mouse) intrasplenically into 8- to 10-week-old NSG mice (n=8 per group). SPIR (1.25 mg/mouse) or PBS was intraperitoneally injected into the mice (n=4 per group) every other day for three times. Hepatic metastasis was analyzed by performing bioluminescence imaging on day 10.* $P<0.05$,  $P<0.005$, * $P<0.0001$.

Figure 11:
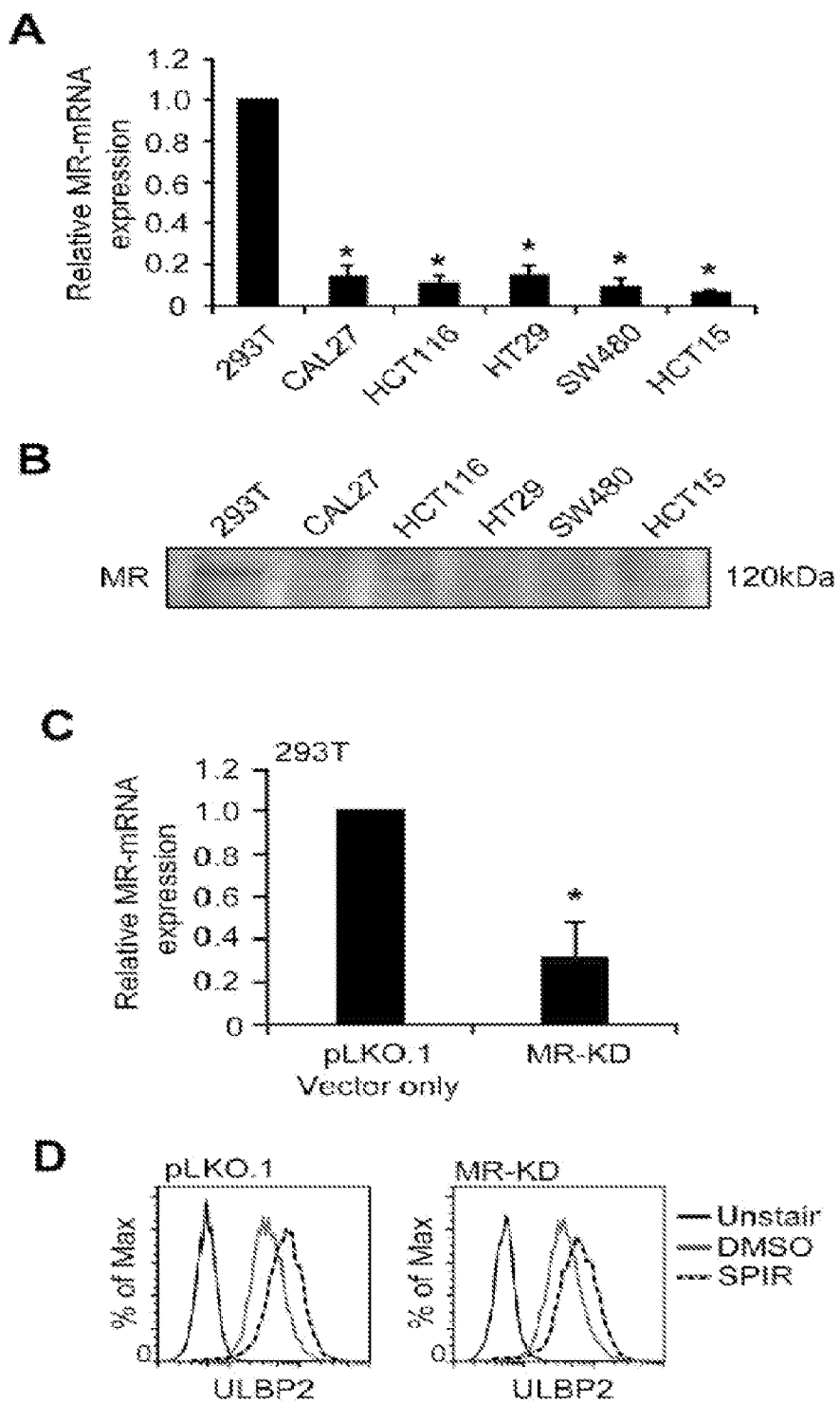

FIG. 11 demonstrates that SPIR's upregulation of NKG2DL is independent of MR. (A) MR mRNA expression was determined by qRT-PCR in various cell lines (n=3). (B) MR protein expression was determined by Western blot analysis. Data shown are representative of two independent experiments. (C) MR-knockdown 293T cells were generated by lentiviral transduction with an shRNA vector (pLKO.1) targeting MR. The relative mRNA expression of MR was analyzed by qRT-PCR (n=3). (D) Surface expression of ULBP2 in control and MR-knockdown 293T cells after DMSO or SPIR treatment for 3 days was analyzed by using flow cytometry. Data shown are representative of two independent experiments. * $P<0.0001$.

Figure 12:
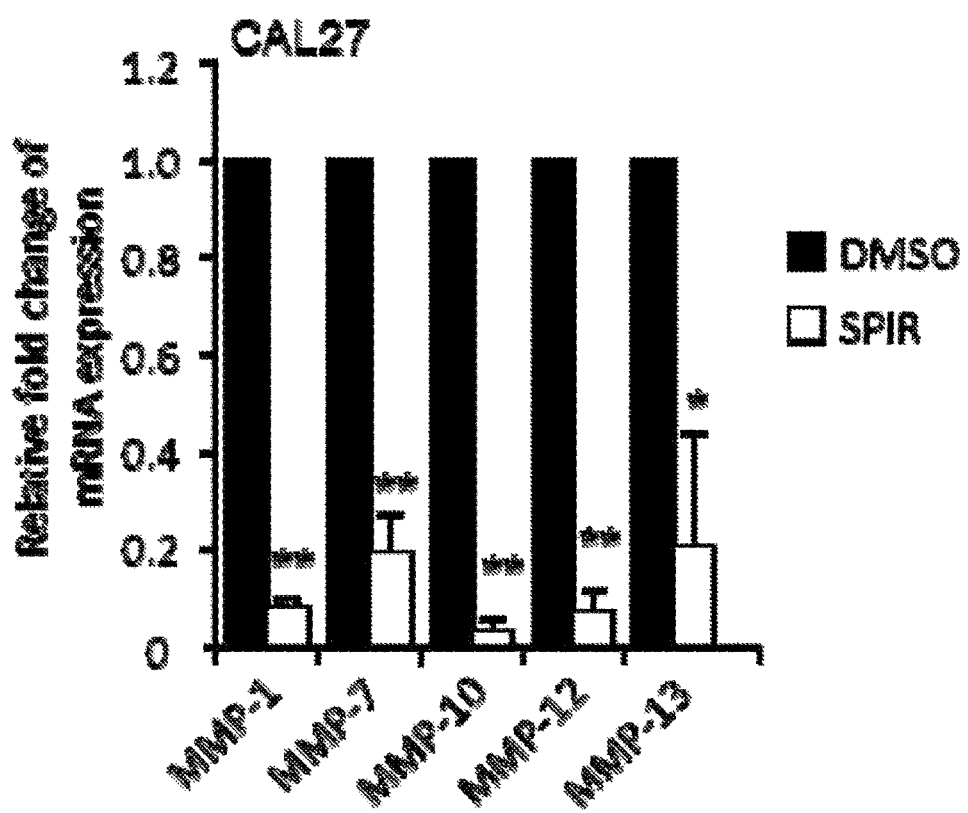

FIG. 12 demonstrates SPIR altered gene expression of various MMPs. RT-qPCR was performed to analyze the mRNA expression of various MMPs (MMP-1, 7, 10, 12, and 13) in CAL27 cells treated with DMSO or SPIR for 3 days. Data were normalized to GAPDH mRNA levels and presented as fold change relative to the mRNA expression in DMSO treated cells (n=3). * $P<0.005$, ** $P<0.001$.

DETAILED DESCRIPTION OF THE INVENTION

The present invention is based on the unexpected observation that spironolactone (SPIR) upregulates NKG2DL expression in multiple colon cancer cell lines by activating the ATM-Chk2-mediated Checkpoint Pathway, which in turn enhances tumor elimination by NK cells. SPIR also upregulates expression of metastasis-suppressor genes TIMP2 and TIMP3, and downregulates expression of Matrix Metalloproteinases (MMPs), including MMP-1, MMP-7, MMP-10, MMP-12, and MMP-13, thereby reducing tumor cell invasiveness. Although SPIR is an aldosterone antagonist, the present invention is based on the unexpected observation that its antitumor effects are independent of the Mineralocorticoid Receptor (MR) Pathway. By screening a human nuclear hormone receptor siRNA library, the present inventors identified Retinoid X Receptor-gamma (RXR-gamma) as being indispensable for the antitumor functions of SPIR. In addition, as demonstrated herein, siRNAs that downregulate the Retinoid X Receptor-alpha (RXR-alpha), also upregulate NKG2DL expression.

Definitions

The term "agonist" as used herein in connection with RXR-gamma encompasses direct activators of a function of RXR-gamma, activators of expression of RXR-gamma, as well as activators of upstream signaling pathways of RXR-gamma.

The term "antagonist" as used herein in connection with RXR-alpha encompasses direct inhibitors of a function of RXR-alpha, inhibitors of expression of RXR-alpha, as well as inhibitors of downstream signaling pathways of RXR-alpha.

The characteristics of agonists and antagonists of the present invention can be assessed by any of the methods known in the art.

For therapeutic applications, the agonists and antagonists of the present invention can be used as pharmaceutical compositions and can be optionally combined with other agonists/antagonists of the invention or other therapeutic (e.g., anti-cancer) molecules and/or treatments.

The term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

In the context of the present invention insofar as it relates to any of the disease conditions recited herein, the terms "treat", "treatment", and the like mean to relieve or alleviate at least one symptom associated with such condition, or to slow or reverse the progression of such condition. Within the meaning of the present invention, the term "treat" also denotes to arrest, delay the onset (i.e., the period prior to clinical manifestation of a disease) and/or reduce the risk of developing or worsening a disease (e.g., in connection with cancer the term "treat" may mean eliminate or reduce a subject's tumor burden, or prevent, delay or inhibit metastasis, etc.).

As used herein the term "therapeutically effective" applied to dose or amount refers to that quantity of a compound or pharmaceutical composition that is sufficient to result in a desired activity upon administration to a subject in need thereof. Within the context of the present invention, the term "therapeutically effective" refers to that quantity of a compound (e.g., an agonist of RXR-gamma or an antagonist of RXR-alpha) or pharmaceutical composition containing such compound that is sufficient to delay the manifestation, arrest the progression, relieve or alleviate at least one symptom of a disorder treated by the methods of the present invention. Note that when a combination of active ingredients is administered the effective amount of the combination may or may not include amounts of each ingredient that would have been effective if administered individually.

The phrase "pharmaceutically acceptable", as used in connection with compositions of the invention, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

As used herein, the term "subject" refers to any mammal. In a preferred embodiment, the subject is human. In another preferred embodiment, the subject is an experimental animal model of a cancer.

As used in this specification and the appended claims, the singular forms "a," "an," and "the" include plural references unless the context clearly dictates otherwise.

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or tricyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-30 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "cycloaliphatic," as used herein, refers to saturated or partially unsaturated cyclic aliphatic monocyclic, bicyclic, or polycyclic ring systems, as described herein, having from 3 to 14 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic," may also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a 'carbocyclic group is tricyclic. In some embodiments, a carbocyclic group is polycyclic. In some embodiments, "cycloaliphatic" (or "carbocycle" or "cycloalkyl") refers to a monocyclic $C_3$-$C_6$ hydrocarbon, or a $C_8$-$C_{10}$ bicyclic hydrocarbon that is completely saturated or that contains one or more units of unsaturation, but which is not aromatic, that has a single point of attachment to the rest of the molecule, or a $C_9$-$C_{16}$ tricyclic hydrocarbon that is completely saturated or that contains one or more units of unsaturation, but which is not aromatic, that has a single point of attachment to the rest of the molecule.

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, a cycloalkyl ring has from about 3-10 carbon atoms in their ring structure where such rings are monocyclic or bicyclic, and alternatively about 5, 6 or 7 carbons' in the ring structure. In some embodiments, an alkyl group may be a lower alkyl group, wherein a lower alkyl group comprises 1-4 carbon atoms (e.g., $C_1$-$C_4$ for straight chain lower alkyls).

As used herein, the term "alkenyl" refers to an alkyl group, as defined herein, having one or more double bonds.

As used herein, the term "alkynyl" refers to an alkyl group, as defined herein, having one or more triple bonds.

The term "heteroalkyl" is given its ordinary meaning in the art and refers to alkyl groups as described herein in which one or more carbon atoms is replaced with a heteroatom (e.g., oxygen, nitrogen, sulfur, and the like). Examples of heteroalkyl groups include, but are not limited to, alkoxy, poly(ethylene glycol)-, alkyl-substituted amino, tetrahydrofuranyl, piperidinyl, morpholinyl, etc.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, binaphthyl, anthracyi and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone of as part of a larger moiety, e.g., "heteroaralkyl," or "heteroaralkoxy," refer to groups having 5 to 10 ring atoms (i.e., monocyclic or bicyclic), in some embodiments 5, 6, 9, or 10 ring atoms. In some embodiments, such rings have 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic, tricyclic, tetracyclic, and/or otherwise polycyclic The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic, tricyclic, tetracyclic, and/or otherwise polycyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring.

The term "unsaturated," as used herein, means that a moiety has one or more units of unsaturation.

The term "halogen" means F, Cl, Br, or I.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{11}$C- or $^{13}$C- or $^{14}$C-enriched carbon are within the scope of this invention. Such compounds are useful, for example, as analytical tools or probes in biological assays.

In accordance with the present invention there may also be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A practical Approach, Volumes I and II (D. N. Glover ed. 1985); Oligonucleotide Synthesis (M J. Gait ed. 1984); Nucleic Acid Hybridization (B. D. Hames & S. J. Higgins eds. (1985)); Transcription and Translation (B. D. Hames & S. J. Higgins, eds. (1984)); Animal Cell Culture (R. I. Freshney, ed. (1986)); Immobilized Cells and Enzymes (IRL Press, (1986)); B. Perbal, A practical Guide To Molecular Cloning (1984); F. M. Ausubel et al. (eds.), Current Protocols in Molecular Biology, John Wiley & Sons, Inc. (1994); among others.

Therapeutic/Treatment Methods of the Invention

As disclosed in detail in the Examples, below, it was unexpectedly discovered by the present inventors that aldosterone antagonist SPIR upregulates NKG2DL surface expression on multiple colorectal cancer cells through the activation of the ATM-Chk2-mediated Checkpoint Pathway, greatly enhancing cancer cell susceptibility to NK cell cytolysis. As further disclosed herein, SPIR enhances expression of metastasis-suppressor genes TIMP2 and TIMP3, and reduces expression of Matrix Metalloproteinases (MMPs), resulting in a significant reduction of cancer metastasis in animal models. Surprisingly, SPIR's effects were independent of the MR Pathway but instead required the activation of RXR-gamma.

In addition, disclosed in detail in the Examples, below, siRNAs that downregulate RXR-alpha, also upregulate NKG2DL expression.

In one embodiment, the invention provides a method for treating or preventing cancer in a subject in need thereof, said method comprising administering to said subject a therapeutically effective amount of an RXR-gamma agonist of formula (I).

In another embodiment, the invention provides a method for enhancing cancer cell susceptibility to NK cell cytotoxicity in a subject having a cancer or a precancerous condition, said method comprising administering to said subject a therapeutically effective amount of an RXR-gamma agonist of formula (I)

In a further embodiment, the invention provides a method for inhibiting cancer metastasis in a subject in need thereof, said method comprising administering to said subject a therapeutically effective amount of an RXR-gamma agonist of formula (I).

In another embodiment, the invention provides a method for upregulating NKG2DL expression in a cancer cell comprising administering to said cell an effective amount of an RXR-gamma agonist of formula (I).

In yet another embodiment, the invention provides a method for enhancing expression of TIMP2 and/or TIMP3 in a cancer cell comprising administering to said cell an effective amount of an RXR-gamma agonist of formula (I).

In a further embodiment, the invention provides a method for suppressing motility and invasiveness of a cancer cell comprising administering to said cell an effective amount of an RXR-gamma agonist of formula (I).

In another embodiment, the invention provides a method for inhibiting expression of one or more Matrix Metalloproteinases (MMPs), in a cancer cell comprising administering to said cell an effective amount of an RXR-gamma agonist of formula (I). In one specific embodiment, MMP expression in said cancer cell is higher than in a corresponding normal cell. In one specific embodiment, said one or more MMPs are selected from the group consisting of MMP-1, MMP-7, MMP-10, MMP-12 and MMP-13.

In one embodiment of any of the above methods, the RXR-gamma agonist is Spironolactone.

In a separate embodiment, the invention provides a method for treating cancer in a subject in need thereof, said method comprising administering to said subject a therapeutically effective amount of an antagonist of RXR-alpha.

In a further embodiment, the invention provides a method for enhancing cancer cell susceptibility to NK cell cytotoxicity in a subject having a cancer or a precancerous condition, said method comprising administering to said subject a therapeutically effective amount of an antagonist of RXR-alpha.

In a preferred embodiment of the above methods involving an antagonist of RXR-alpha, said antagonist of RXR-alpha said antagonist of RXR-alpha does not inhibit RXR-gamma.

In one embodiment of the above methods involving an antagonist of RXR-alpha, said antagonist of RXR-alpha is siRNA. In one specific embodiment, said siRNA comprises the sequence GGGAGAAGGUCUAUGCGUC (SEQ ID NO: 1). In one specific embodiment, said siRNA consists of the sequence GGGAGAAGGUCUAUGCGUC (SEQ ID NO: 1).

In one embodiment of the above methods involving an antagonist of RXR-alpha, said antagonist of RXR-alpha is an antibody.

In one embodiment of the above methods involving a cancer cell, said cancer cell is in a subject. In one embodiment of the above methods involving a cancer cell, is characterized by a decreased NKG2DL expression, as compared to a corresponding normal cell.

In one embodiment of any of the above methods, the subject is human. In another embodiment of any of the above methods, the subject is an experimental animal model of a cancer.

Non-limiting examples of cancers treatable by the methods of the invention include, e.g., colorectal cancer, head and neck cancer, prostate cancer, hepatocellular carcinoma, rhabdomyosarcoma, hepatocellular adenoma, cholangiocarcinoma, colorectal adenoma, ileal adenoma, renal cancer, oesophageal cancer, gastric cancer, breast cancer, and esophageal cancer.

It is contemplated that when used to treat cancer, more than one RXR-gamma agonist and/or RXR-alpha antagonist can be used, and/or such one or more RXR-gamma agonists and/or RXR-alpha antagonists can be further combined with each other and/or with other therapeutic agents and/or treatments suitable for treatment of cancer. Two or more active agents may be co-administered to generate additive or synergistic effects. Suitable therapeutically effective dosages for each agent may be lowered due to the additive action or synergy.

Therapeutic methods of the invention can be combined with additional anti-cancer therapies such as, e.g., surgery, radiotherapy, chemotherapy or combinations thereof, depending on type of the tumor, patient condition, other health issues, and a variety of factors. In certain aspects, other therapeutic agents useful for combination cancer therapy with the inhibitors of the invention include anti-angiogenic agents. Many anti-angiogenic agents have been identified and are known in the art, including, e.g., TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alpha, soluble KDR and FLT-1 receptors, placental proliferin-related protein, VEGF antagonists, VEGF receptor antagonists (such as anti-VEGF antibodies), VEGF variants, soluble VEGF receptor fragments, aptamers capable of blocking VEGF or VEGFR, neutralizing anti-VEGFR antibodies, inhibitors of VEGFR tyrosine kinases, and any combinations thereof (e.g., anti-hVEGF antibody A4.6.1, bevacizumab or ranibizumab). See also Carmeliet and Jain (2000).

Non-limiting examples of chemotherapeutic compounds which can be used in combination treatments of the present invention include, for example, aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estramnustine, etoposide, exemestane, filgrastim, fludarabine, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, thioguanine, thiotepa, titanocene dichloride, topotecan, trastuzumab, tretinoin, vinblastine, vincristine, vindesine, vinorelbine, sorafenib, sunitinib, erlotinib imatinib, panitumumab, trastuzumab These chemotherapeutic compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); anti-proliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethyhnelamineoxaliplatin, phosphamide, melphalan, merchloretamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan); growth factor signal transduction kinase inhibitors; mitochondrial dysfunction inducers; and chromatin disruptors.

Appropriate combination treatment for tumors depends on the type of cell from which the tumor derived, the stage and severity of the malignancy, and the genetic abnormality that contributes to the tumor.

In some embodiments, the at least one RXR-gamma agonist and/or RXR-alpha antagonist is formulated into a suitable pharmaceutical preparation such as, e.g., solution, suspension, tablet, dispersible tablet, pill, capsule, powder, sustained release formulation or elixir, for oral administration or in sterile solution or suspension for parenteral administration, or as transdermal patch preparation or dry powder inhaler. RXR-gamma agonist and/or RXR-alpha antagonist can be formulated into pharmaceutical compositions using any of the techniques and procedures known in the art (see, e.g., Ansel Introduction to Pharmaceutical Dosage Forms, Fourth Edition 1985, 126).

In the compositions, effective concentrations of one or more RXR-gamma agonists and/or RXR-alpha antagonists or pharmaceutically acceptable derivatives thereof is (are) mixed with a suitable pharmaceutical carrier or vehicle.

Pharmaceutically acceptable derivatives include acids, bases, enol ethers and esters, salts, esters, hydrates, solvates and prodrug forms. A suitable derivative is selected such that its pharmacokinetic properties are superior with respect to at least one characteristic to the corresponding parent agent. The RXR-gamma agonist and/or RXR-alpha antagonist may be derivatized prior to formulation.

The concentrations of the RXR-gamma agonist and/or RXR-alpha antagonist in the compositions are effective for delivery of an amount, upon administration, that treats one or more of the symptoms of at least one tumor.

Typically, by way of example and without limitation, the compositions are formulated for single dosage administration. To formulate a composition, the weight fraction of RXR-gamma agonist and/or RXR-alpha antagonist is dissolved, suspended, dispersed or otherwise mixed in a selected vehicle at an effective concentration such that the treated condition, a malignancy, is relieved or ameliorated. Pharmaceutical carriers or vehicles suitable for administration of the RXR-gamma agonist and/or RXR-alpha antagonist include any such carriers known to those skilled in the art to be suitable for the particular mode of administration.

The RXR-gamma agonist and/or RXR-alpha antagonist may be included in the pharmaceutically acceptable carrier in an amount sufficient to exert a therapeutically useful effect in the absence of certain undesirable side effects on the subject treated. The therapeutically effective concentration may be determined empirically by testing the agents in in vitro and in vivo systems described herein and in WO/2011/020615.

The concentration of active RXR-gamma agonist and/or RXR-alpha antagonist in the pharmaceutical composition will depend on absorption, inactivation and excretion rates of the active agent, the physicochemical characteristics of the agent, the dosage schedule, and amount administered as well as other factors known to those of skill in the art. For example, the amount that is delivered is sufficient to treat at least one tumor as described herein.

Typically a therapeutically effective dosage should produce a serum concentration of active agent of from about 0.1 ng/mL to about 50-100 g/mL. The pharmaceutical compositions typically should provide a dosage of from about 0.001 mg to about 2000 mg of RXR-gamma agonist and/or RXR-alpha antagonist per kilogram of body weight per day. Pharmaceutical dosage unit forms are prepared to provide from about 1 mg to about 1000 mg, such as from about 10 to about 500 mg of the active agent or a combination of agents per dosage unit form.

The active agent may be administered at once, or may be divided into a number of smaller doses to be administered at intervals of time. It is understood that the precise dosage and duration of treatment is a function of the tumor being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed methods.

Thus, effective concentrations or amounts of one or more RXR-gamma agonist and/or RXR-alpha antagonist or pharmaceutically acceptable derivatives thereof are mixed with a suitable pharmaceutical carrier or vehicle for systemic, topical or local administration to form pharmaceutical compositions. RXR-gamma agonists and/or RXR-alpha antagonists are included in an amount effective for treating at least one tumor. The concentration of active agent in the composition will depend on absorption, inactivation, excretion rates of the active agent, the dosage schedule, amount administered, particular formulation as well as other factors known to those of skill in the art.

The compositions are intended to be administered by a suitable route, including by way of example and without limitation orally, parenterally, rectally, topically and locally. For oral administration, capsules and tablets can be used. The compositions are in liquid, semi-liquid or solid form and are formulated in a manner suitable for each route of administration.

Solutions or suspensions used for parenteral, intradermal, subcutaneous, or topical application can include any of the following components, in any combination: a sterile diluent, including by way of example without limitation, water for injection, saline solution, fixed oil, polyethylene glycol, glycerine, propylene glycol or other synthetic solvent; anti-microbial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampoules, disposable syringes or single or multiple dose vials made of glass, plastic or other suitable material.

In instances in which the agents exhibit insufficient solubility, methods for solubilizing agents may be used. Such methods are known to those of skill in this art, and include, but are not limited to, using co-solvents, such as dimethylsulfoxide (DMSO), using surfactants, such as TWEEN® 80, or dissolution in aqueous sodium bicarbonate. Pharmaceutically acceptable derivatives of the agents may also be used in formulating effective pharmaceutical compositions.

Upon mixing or addition of the agent(s), the resulting mixture may be a solution, suspension, emulsion or the like. The form of the resulting mixture depends upon a number of factors, including the intended mode of administration and the solubility of the agent in the selected carrier or vehicle. The effective concentration is sufficient for treating one or more symptoms of at least one malignancy and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the agents or pharmaceutically acceptable derivatives thereof. The pharmaceutically therapeutically active agents and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active agent sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can contain along with the active agent, for example and without limitation: a diluent such as lactose, sucrose, dicalcium phosphate, or carboxymethylcellulose; a lubricant, such as magnesium stearate, calcium stearate and talc; and a binder such as starch, natural gums, such as gum acacia gelatin, glucose, molasses, polyvinylpyrrolidone, celluloses and derivatives thereof, povidone, crospovidones and other such binders known to those of skill in the art. Liquid pharmaceutically administrable compositions can, for example, be prepared by dissolving, dispersing, or otherwise mixing an active agent as defined above and optional pharmaceutical adjuvants in a carrier, such as, by way of example and without limitation, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, such as, by way of example and without limitation, acetate, sodium citrate, cyclodextrin derivatives, sorbitan monolaurate, triethanolamine sodium acetate, triethanolamine oleate, and other such agents. Actual methods of preparing such dosage forms are known, or will be apparent, to those skilled in this art (e.g., Remington's Pharmaceutical Sciences, Mack Publishing Company, Easton, Pa., 15th Edition, 1975). The composition or formulation to be administered will, in any event, contain a quantity of the active agent in an amount sufficient to alleviate the symptoms of the treated subject.

Dosage forms or compositions containing active agent in the range of 0.005% to 100% with the balance made up from non-toxic carrier may be prepared. For oral administration, a pharmaceutically acceptable non-toxic composition is formed by the incorporation of any of the normally employed excipients, such as, for example and without limitation, pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain 0.001%-100% active agent, such as 0.1-85%, or such as 75-95%.

The active agents or pharmaceutically acceptable derivatives may be prepared with carriers that protect the agent against rapid elimination from the body, such as time release formulations or coatings. The compositions may include other active agents to obtain desired combinations of properties. RXR-gamma agonists and/or RXR-alpha antagonists or pharmaceutically acceptable derivatives thereof, may also be advantageously administered for therapeutic or prophylactic purposes together with another pharmacological agent known in the general art to be of value in treating at least one malignancy.

Oral pharmaceutical dosage forms include, by way of example and without limitation, solid, gel and liquid. Solid dosage forms include tablets, capsules, granules, and bulk powders. Oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or agents of a similar nature: a binder; a diluent; a disintegrating agent; a lubricant; a glidant; a sweetening agent; and a flavoring agent.

Examples of binders include, by way of example and without limitation, microcrystalline cellulose, gum tragacanth, glucose solution, acacia mucilage, gelatin solution, sucrose, and starch paste. Lubricants include, by way of example and without limitation, talc, starch, magnesium or calcium stearate, lycopodium and stearic acid. Diluents include, by way of example and without limitation, lactose, sucrose, starch, kaolin, salt, mannitol, and dicalcium phosphate. Glidants include, by way of example and without limitation, colloidal silicon dioxide. Disintegrating agents include, by way of example and without limitation, crosscarmellose sodium, sodium starch glycolate, alginic acid, corn starch, potato starch, bentonite, methylcellulose, agar and carboxymethylcellulose. Coloring agents include, by way of example and without limitation, any of the approved certified water soluble FD and C dyes, mixtures thereof; and water insoluble FD and C dyes suspended on alumina hydrate. Sweetening agents include, by way of example and without limitation, sucrose, lactose, mannitol and artificial sweetening agents such as saccharin, and any number of spray dried flavors. Flavoring agents include, by way of example and without limitation, natural flavors extracted from plants such as fruits and synthetic blends of agents which produce a pleasant sensation, such as, but not limited to peppermint and methyl salicylate. Wetting agents include, by way of example and without limitation, propylene glycol monostearate, sorbitan monooleate, diethylene glycol monolaurate, and polyoxyethylene laural ether. Emetic-coatings include, by way of example and without limitation, fatty acids, fats, waxes, shellac, ammoniated shellac and cellulose acetate phthalates. Film coatings include, by way of example and without limitation, hydroxyethylcellulose, sodium carboxymethylcellulose, polyethylene glycol 4000 and cellulose acetate phthalate.

If oral administration is desired, the agent could be provided in a composition that protects it from the acidic environment of the stomach. For example, the composition can be formulated in an enteric coating that maintains its integrity in the stomach and releases the active agent in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The agents can also be administered as a component of an elixir, suspension, syrup, wafer, sprinkle, chewing gum or the like. A syrup may contain, in addition to the active agents, sucrose as a sweetening agent and certain preservatives, dyes and colorings and flavors. The active materials can also be mixed with other active materials which do not impair the desired action, or with materials that supplement the desired action, such as antacids, H2 blockers, and diuretics.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents may be used in any of the above dosage forms.

Solvents, include by way of example and without limitation, glycerin, sorbitol, ethyl alcohol and syrup. Examples of preservatives include without limitation glycerin, methyl and propylparaben, benzoic add, sodium benzoate and alcohol. Non-aqueous liquids utilized in emulsions, include by way of example and without limitation, mineral oil and cottonseed oil. Emulsifying agents, include by way of example and without limitation, gelatin, acacia, tragacanth, bentonite, and surfactants such as polyoxyethylene sorbitan monooleate. Suspending agents include, by way of example and without limitation, sodium carboxymethylcellulose, pectin, tragacanth, Veegum and acacia. Diluents include, by way of example and without limitation, lactose and sucrose. Sweetening agents include, by way of example and without limitation, sucrose, syrups, glycerin and artificial sweetening agents such as saccharin. Wetting agents, include by way of example and without limitation, propylene glycol monostearate, sorbitan monooleate, diethylene glycol monolaurate, and polyoxyethylene lauryl ether. Organic acids include, by way of example and without limitation, citric and tartaric acid. Sources of carbon dioxide include, by way of example and without limitation, sodium bicarbonate and sodium carbonate. Coloring agents include, by way of example and without limitation, any of the approved certified water soluble FD and C dyes, and mixtures thereof. Flavoring agents include, by way of example and without limitation, natural flavors extracted from plants such fruits, and synthetic blends of agents which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245, 4,409,239, and 4,410,545. For a liquid dosage form, the solution (e.g., in a polyethylene glycol) may be diluted with a sufficient quantity of a pharmaceutically acceptable liquid carrier (e.g., water) to be easily measured for administration.

Alternatively, liquid or semi-solid oral formulations may be prepared by dissolving or dispersing the active agent or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. RE28819 and U.S. Pat. No. 4,358,603. Briefly, such formulations include, but are not limited to, those containing an agent provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Tablets and capsules formulations may be coated as known by those of skill in the art in order to modify or sustain dissolution of the active ingredient. Thus, for example and without limitation, they may be coated with a conventional enterically digestible coating, such as phenyl-salicylate, waxes and cellulose acetate phthalate.

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients, include by way of example and without limitation, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (e.g., U.S. Pat. No. 3,710,795) is also contemplated herein. Briefly, an RXR-gamma agonist is dispersed in a solid inner matrix (e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate) that is surrounded by an outer polymeric membrane (e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer) that is insoluble in body fluids. The agent diffuses through the outer polymeric membrane in a release rate controlling step. The percentage of active agent contained in such parenteral compositions is highly dependent on the specific nature thereof, as well as the activity of the agent and the needs of the subject.

Parenteral administration of RXR-gamma agonists includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble, products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Aqueous vehicles include, by way of example and without limitation, sodium chloride injection, Ringers injection, isotonic dextrose injection, sterile water injection, dextrose and lactated Ringers injection. Nonaqueous parenteral vehicles include, by way of example and without limitation, fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl para-hydroxybenzoic acid esters, thimerosal, benzalkonium chloride and benzethonium chloride. Isotonic agents include, by way of example and without limitation, sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropylmethylcellulose and polyvinylpyrrolidone. Emulsifying agents include Polysorbate 80 (TWEEN® 80). A sequestering or chelating agent of metal ions include EDTA. Pharmaceutical carriers also include, by way of example and without limitation, ethyl alcohol, polyethylene glycol and propylene glycol for water miscible vehicles and sodium hydroxide, hydrochloric acid, citric acid or lactic acid for pH adjustment.

The concentration of the pharmaceutically active agent is adjusted so that an injection provides an effective amount to produce the desired pharmacological effect. The exact dose depends on the age, weight and condition of the subject or animal as is known in the art.

The unit-dose parenteral preparations are packaged in an ampoule, a vial or a syringe with a needle. Preparations for parenteral administration should be sterile, as is known and practiced in the art.

Illustratively, intravenous or intraarterial infusion of a sterile aqueous solution containing an active agent is an effective mode of administration. Another embodiment is a sterile aqueous or oily solution or suspension containing an active agent injected as necessary to produce the desired pharmacological effect.

Injectables are designed for local and systemic administration. Typically a therapeutically effective dosage is formulated to contain a concentration of at least about 0.1% w/w up to about 90% w/w or more, such as more than 1% w/w of the active agent to the treated tissue(s). The active agent may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The agent may be suspended in micronized or other suitable form or may be derivatized (e.g., to produce a more soluble active product or to produce a prodrug or other pharmaceutically acceptable derivative). The form of the resulting mixture depends upon a number of factors, including the intended mode of administration and the solubility of the agent in the selected carrier or vehicle. The effective concentration is sufficient for ameliorating the symptoms of the condition and may be empirically determined.

Lyophilized powders can be reconstituted for administration as solutions, emulsions, and other mixtures or formulated as solids or gels.

The sterile, lyophilized powder is prepared by dissolving an agent provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain, by way of example and without limitation, a single dosage (10-1000 mg, such as 100-500 mg) or multiple dosages of the agent. The lyophilized powder can be stored under appropriate conditions, such as at about 4° C. to room temperature. Reconstitution of this lyophilized powder with water for injection provides a formulation for use in parenteral administration. For reconstitution, about 1-50 mg, such as about 5-35 mg, for example, about 9-30 mg of lyophilized powder, is added per mL of sterile water or other suitable carrier. The precise amount depends upon the selected agent. Such amount can be empirically determined.

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The agents or pharmaceutically acceptable derivatives thereof may be formulated as aerosols for topical application, such as by inhalation (e.g., U.S. Pat. Nos. 4,044,126, 4,414,209, and 4,364,923 which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, by way of example and without limitation, have diameters of less than about 50 microns, such as less than about 10 microns.

The agents may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active agent alone or in combination with other pharmaceutically acceptable excipients can also be administered.

These solutions, particularly those intended for ophthalmic use, may be formulated, by way of example and without limitation, as about 0.01% to about 10% isotonic solutions, pH about 5-7, with appropriate salts.

Other routes of administration, such as transdermal patches, and rectal administration are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010,715, 5,985,317, 5,983,134, 5,948,433, and 5,860,957.

Pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is, by way of example and without limitation, about 2 to 3 g.

Tablets and capsules for rectal administration are manufactured using the same pharmaceutically acceptable substance and by the same methods as for formulations for oral administration.

RXR-gamma agonists and/or RXR-alpha antagonist, or pharmaceutically acceptable derivatives thereof, may also be formulated to be targeted to a particular tissue or other area of the body of the subject to be treated. Many such targeting methods are well known to those of skill in the art. Such targeting methods are contemplated herein for use in the instant compositions. For non-limiting examples of targeting methods, see e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In some embodiments, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles may be formed by drying down egg phosphatidyl choline and brain phosphatidyl serine (7:3 molar ratio) on the inside of a flask. A solution of an agent provided herein in phosphate buffered saline lacking divalent cations (PBS) is added and the flask shaken until the lipid film is dispersed. The resulting vesicles are washed to remove unencapsulated agent, pelleted by centrifugation, and then resuspended in PBS.

RXR-gamma agonists and/or RXR-alpha antagonists or pharmaceutically acceptable derivatives for use in the present invention may be packaged as articles of manufacture containing packaging material, an RXR-gamma agonist and/or RXR-alpha antagonist or pharmaceutically acceptable derivative thereof provided herein, which is effective for modulating the activity of RXR-gamma or RXR-alpha or for treatment, of one or more symptoms of at least one tumor within the packaging material, and a label that indicates that the RXR-gamma agonist and/or RXR-alpha antagonist or composition, or pharmaceutically acceptable derivative thereof, is used for modulating the activity of RXR-gamma for treatment of one or more symptoms of at least one tumor.

In the methods of the invention, when determination of metastasis or invasiveness is involved, the invasive and metastatic activities of cells can be measured using standard in vitro and in vivo methods. In some embodiments, invasion potential can be measured with assays that monitor the ability of cells to migrate through synthetic matrix. In some embodiments, metastatic potential can be measured in assays that monitor the dissemination of implants of test cells in animals.

In some embodiments, the effects of agents and compositions on RXR-gamma or RXR-alpha activity can be evaluated in cells. Typically, the cells will express RXR-gamma or RXR-alpha either endogenously or heterogeneously by co-transfection. Cells that express RXR-gamma or RXR-alpha endogenously include, by way of example and without limitation: hepatocytes, including primary hepatocytes isolated from human, monkey, mouse, or rat, or hepatocyte cell lines, including HepG2, Huh7, or SK-Hep-1 cells; and intestinal cells including HCT116, HT-29, CaCo2 and FHs 74 Int.

In some embodiments, the effects of agents and compositions on RXR-gamma or RXR-alpha activity can be evaluated in animals. Without limitation, for example, after the administration of agents, various tissues can be harvested to determine the effect of agents on activities directly or indirectly regulated by RXR-gamma or RXR-alpha.

RXR-Gamma Agonists of the Invention

In some embodiments, the present invention provides methods comprising the step of administering a compound of formula (I):

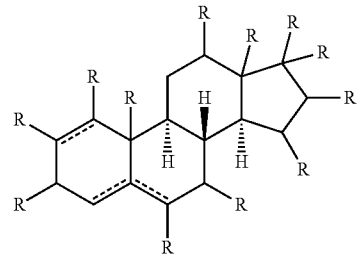

wherein,
each of R is independently hydrogen, halogen, R*, —OH, =O, —NO$_2$, —CN, —OR$^\#$, —SR$^\#$, —N(R$^\#$)$_2$, —C(O)R$^\#$, —CO$_2$R$^\#$, —C(O)C(O)R, —C(O)CH$_2$C(O)R$^\#$, —S(O)R#, —S(O)$_2$R$^\#$, —C(O)N(R$^\#$)$_2$, —SO$_2$N(R$^\#$)$_2$, —OC(O)R$^\#$, —N(R$^\#$)C(O)R$^\#$, —N(R$^\#$)N(R$^\#$)$_2$, —N(R$^\#$)C(=NR$^\#$)N(R$^\#$)$_2$, —C(=NR$^\#$)N(R$^\#$)$_2$, —C=NOR$^\#$, —N(R$^\#$)C(O)N(R$^\#$)$_2$, —N(R$^\#$)SO$_2$N(R$^\#$)$_2$, —N(R$^\#$)SO$_2$R, —OC(O)N(R$^\#$)$_2$, or an optionally substituted C$_{1-12}$ aliphatic group, or two R groups are taken together with their intervening atoms to form an optionally substituted 3- to 7-membered ring having 0-4 heteroatoms selected from nitrogen, oxygen, or sulfur;
each R$^\#$ is independently hydrogen or R*;
each R* is independently an optionally substituted group selected from C$_{1-10}$ aliphatic, aryl, a 3-7 membered saturated or partially unsaturated carbocyclic ring, a 3-7 membered saturated or partially unsaturated monocyclic heterocyclic ring having 0-2 heteroatoms independently selected from nitrogen, oxygen, or sulfur, or a heteroaryl ring having 0-3 heteroatoms independently selected from nitrogen, oxygen, or sulfur; or: two R* groups on the same nitrogen are taken together with their intervening atoms to form an optionally substituted 3-7 membered saturated, partially unsaturated, or heteroaryl ring having 0-4 heteroatoms independently selected from nitrogen, oxygen, or sulfur.

In certain embodiments, each of R is independently selected from a substituted or unsubstituted nitrogen, oxygen or sulfur, such as for example any of structures (a)-(f), or a =O, or a group (g):

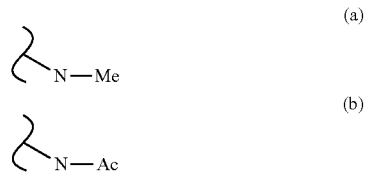

-continued

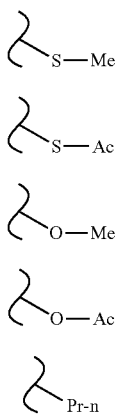

(c)
(d)
(e)
(f)
(g)

In certain embodiment, two R groups are taken together with their intervening atoms to form an optionally substituted group selected from heterocyclic lactone, lactam, lactim, or lactide, or a 3-7 membered saturated or partially unsaturated carbocyclic ring, or a 3-7 membered saturated or partially unsaturated monocyclic heterocyclic ring having 0-2 heteroatoms independently selected from nitrogen, oxygen, or sulfur, or a 5-6 membered heteroaryl ring having 0-3 heteroatoms independently selected from nitrogen, oxygen, or sulfur, or two R groups on the same nitrogen taken together with their intervening atoms to form an optionally substituted 3-7 membered saturated, partially unsaturated, or heteroaryl ring having 0-4 heteroatoms independently selected from nitrogen, oxygen, or sulfur.

In certain embodiments, two R groups are taken together with their intervening atoms to form an optionally substituted group selected from the following (h)-(l):

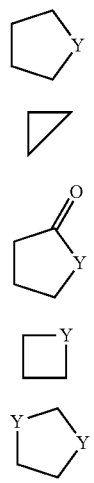

(h)
(i)
(j)
(k)
(l)

wherein Y can be N, O, S, S=O, or $SO_2$, preferably N or O, more preferably O.

In certain embodiments, the compound of formula I contains multiple such groups (i.e., containing two R groups taken together with their intervening atoms to form an optionally substituted group) as described above, herein and as demonstrated by the non-limited exemplary groups (h)-(l).

As would be appreciated by one of skill in the art, the dashed bonds of formula I can represent a single bond or a double bond. Thus, the structure in formula I would include formula I(a), I(b), and I(c), as shown below.

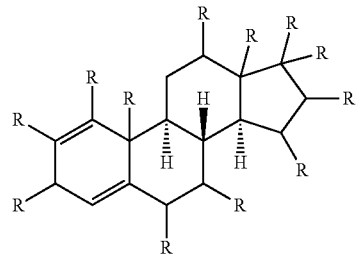

I(a)

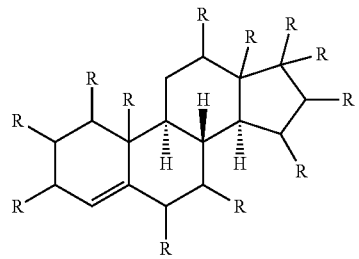

I(b)

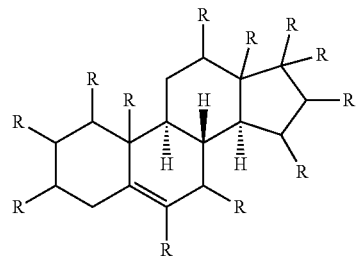

I(c)

In some embodiments, the present invention provides methods comprising the step of administering a compound of formula (II):

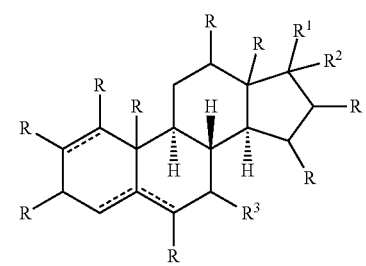

II wherein R is as defined above, $R^1$ and $R^2$ taken together with the carbon to which they are attached form a ring (h), (j), (k) or (l), as disclosed above, with Y being O, and $R^3$ a substituted or unsubstituted nitrogen, oxygen or sulfur, such as any of structures (a)-(f), or a =O.

In some embodiments, the present invention provides methods comprising the step of administering a compound of formula (III)

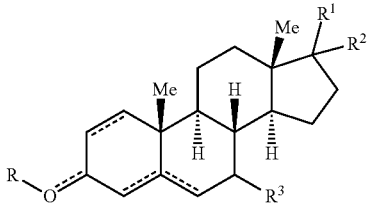

III wherein R is as defined above, $R^1$ and $R^2$ taken together with the carbon to which they are attached form a ring (h), (j), (k) or (l), as disclosed above, with Y being O, and $R^3$ a substituted or unsubstituted nitrogen, oxygen or sulfur, such as any of structures (a)-(f), or a =O.

In some embodiments, the compound of Formula I is a compound of Formula IV:

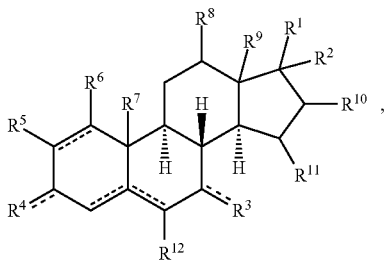

IV wherein:
----- is an optional double bond;
or $R^1$ and $R^2$ together with the atom to which they are attached form a 3-, 4-, 5- or 6-membered heterocycloalkyl group;
$R^3$ is H; $SR^a$; O; $C_{1-6}$-alkyl;
$R^4$ is O; $OR^b$;
$R^5$, $R^6$, $R^7$, $R^8$, $R^9$, $R^{10}$, and $R^{11}$ are each, independently, H or $C_{1-6}$alkyl;
or $R^{10}$ and $R^{11}$ together with the atoms from which they are attached form a 3-, 4-, or 5-membered cycloalkyl group;
$R^{12}$ is H or $OR^c$;
or $R^3$ and $R^{12}$ together with the atoms from which they are attached form a 3-, 4-, or 5-membered cycloalkyl group; and
$R^a$, $R^b$, and $R^c$ are each, independently, H; $C_{1-6}$-alkyl; $C(O)C_{1-6}$-alkyl.

In some embodiments, the compound of Formula IV is a compound of Formula IV(a):

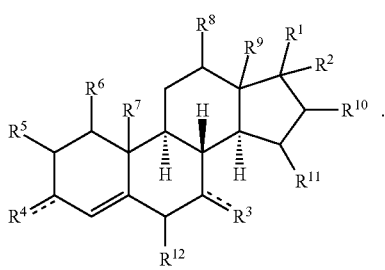

IV(a)

In some embodiments, the compound of Formula IV is a compound of Formula IV(b):

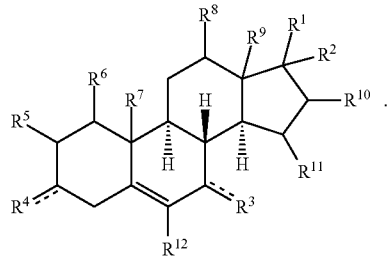

IV(b)

In some embodiments, the compound of Formula IV is a compound of Formula IV(c):

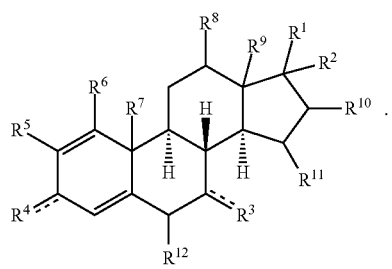

IV(c)

In some embodiments, $R^1$ and $R^2$, together with the atom to which they are attached form a 4- or 5-membered heterocycloalkyl group.

In some embodiments, $R^1$ and $R^2$, together with the atom to which they are attached form a 4-membered hetercycloalkyl group.

In some embodiments, $R^1$ and $R^2$, together with the atom to which they are attached form a 5-membered heterocycloalkyl group.

In some embodiments, the heterocycloalkyl group is a dihydrofuranonyl or an oxetanyl group.

In some embodiments, the heterocycloalkyl group is a dihydrofuranonyl group.

In some embodiments, the heterocycloalkyl group is an oxetanyl group.

In some embodiments, $R^3$ is H.
In some embodiments, $R^3$ is $SR^a$.
In some embodiments, $SR^a$ is SH; $SC_{1-6}$alkyl; or $SC(O)C_{1-6}$alkyl.
In some embodiments, $R^3$ is SH.
In some embodiments, $R^3$ is $SC_{1-6}$alkyl.
In some embodiments, $R^3$ is $SCH_3$.
In some embodiments, $R^3$ is $SC(O)C_{1-6}$alkyl.
In some embodiments, $R^3$ is $SC(O)CH_3$.
In some embodiments, $R^3$ is O.
In some embodiments, $R^3$ is $C_{1-6}$alkyl.
In some embodiments, $R^3$ is $C_{1-3}$alkyl.
In some embodiments, $R^3$ is methyl.
In some embodiments, $R^3$ is ethyl.
In some embodiments, $R^3$ is propyl.
In some embodiments, $R^3$ is n-propyl.
In some embodiments, $R^4$ is O or $OR^b$;
In some embodiments, $R^4$ is O.
In some embodiments, $R^4$ is $OR^b$.
In some embodiments, $OR^b$ is OH; $OC_{1-6}$alkyl; or $OC(O)C_{1-6}$-alkyl.

In some embodiments, $R^4$ is OH.
In some embodiments, $R^4$ is $OC_{1-6}$-alkyl.
In some embodiments, $R^4$ is $OC_{1-3}$alkyl.
In some embodiments, $R^4$ is $OC(O)C_{1-6}$alkyl.
In some embodiments, $R^4$ is $OC(O)C_{1-3}$alkyl.
In some embodiments, $R^4$ is $OC(O)CH_3$.
In some embodiments, $R^5$ is H.
In some embodiments, $R^5$ is $C_{1-6}$ alkyl.
In some embodiments, $R^6$ is H.
In some embodiments, $R^6$ is $C_{1-6}$ alkyl.
In some embodiments, $R^7$ is H.
In some embodiments, $R^7$ is $C_{1-6}$ alkyl.
In some embodiments, $R^7$ is $C_{1-3}$ alkyl.
In some embodiments, $R^7$ is methyl.
In some embodiments, $R^7$ is ethyl.
In some embodiments, $R^7$ is propyl.
In some embodiments, $R^8$ is H.
In some embodiments, $R^8$ is $C_{1-6}$alkyl.
In some embodiments, $R^9$ is H.
In some embodiments, $R^9$ is $C_{1-6}$alkyl.
In some embodiments, $R^9$ is $C_{1-3}$ alkyl.
In some embodiments, $R^9$ is methyl.
In some embodiments, $R^9$ is ethyl.
In some embodiments, $R^9$ is propyl.
In some embodiments, $R^{10}$ is H.
In some embodiments, $R^{10}$ is $C_{1-6}$alkyl.
In some embodiments, $R^{11}$ is H.
In some embodiments, $R^{11}$ is $C_{1-6}$alkyl.
In some embodiments, $R^{10}$ and $R^{11}$, together with the atoms from which they are attached form a 3- or 4-membered cycloalkyl group.
In some embodiments, $R^{10}$ and $R^{11}$, together with the atoms from which they are attached form a 3-membered cycloalkyl group.
In some embodiments, the 3-membered cycloalkyl group is a cyclopropyl group.
In some embodiments, $R^{12}$ is H or $OR^c$.
In some embodiments, $R^{12}$ is H.
In some embodiments, $R^{12}$ is $OR^c$.
In some embodiments, $OR^c$ is OH; $OC_{1-6}$alkyl; or $OC(O)C_{1-6}$alkyl.
In some embodiments, $R^{12}$ is OH.
In some embodiments $R^{12}$ is $OC_{1-6}$alkyl.
In some embodiments, $R^{12}$ is $OC(O)C_{1-6}$alkyl.
In some embodiments, $R^3$ and $R^{12}$, together with the atoms from which they are attached form a 3- or 4-membered cycloalkyl group.
In some embodiments, $R^3$ and $R^{12}$, together with the atoms from which they are attached form a 3-membered cycloalkyl group.
In some embodiments, the 3-membered cycloalkyl group is a cyclopropyl group.
In some embodiments, the present invention provides methods comprising the step of administering a compound of formula (IV).
In certain embodiments, a compound of formula I is selected from the non-limiting exemplary compounds 1-20 below:

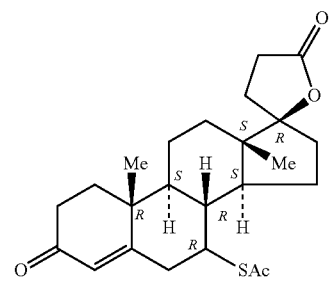

Absolute stereochemistry.
CAS (52-01-7) Spironolactone (1)

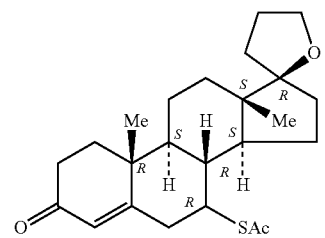

Absolute stereochemistry.
(6673-97-8) SPIROXASONE (2)

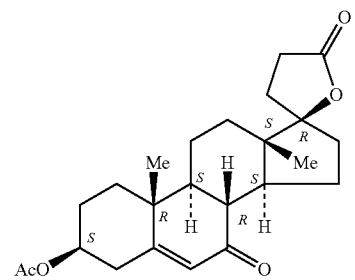

Absolute stereochemistry.
(30597-62-7) 7-Ketoandrenolactone acetate (3)

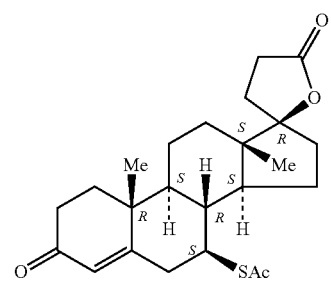

Absolute stereochemistry.
(33784-05-3) 7-β-Spironolactone (4)

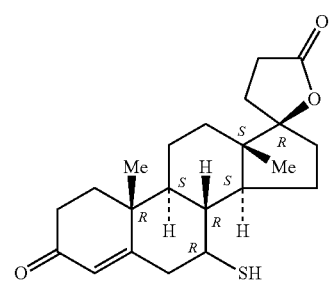

Absolute stereochemistry.
(38753-76-3) Deacetylspironolactone (5)

-continued

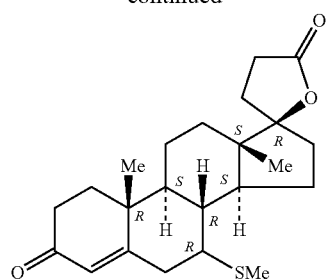

Absolute stereochemistry.
(38753-77-4) 7-α-(Thiomethyl)spirolactone (6)

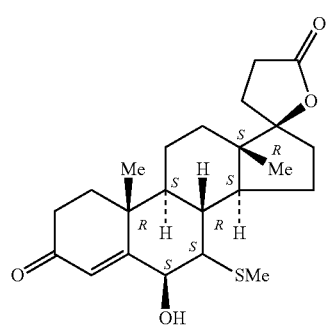

Absolute stereochemistry.
(42219-60-3) 6β-Hydroxy-7α-(thiomethyl)spirolactone (7)

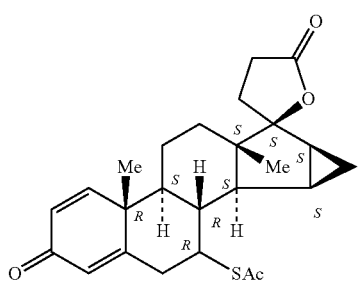

Absolute stereochemistry.
(87952-98-5) Mespirenone (8)

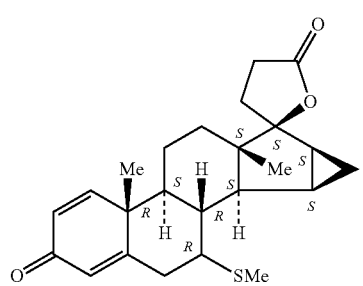

Absolute stereochemistry.
(97870-25-2) ZK 97894 (9)

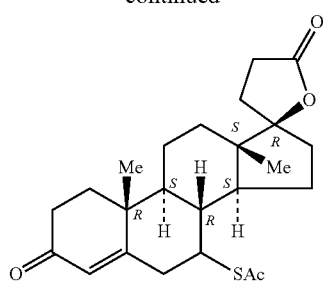

Absolute stereochemistry.
(244290-14-0) 17α-Pregn-4-ene-21-carboxylic acid, 17-hydroxy-7-mercapto-3-oxo-, γ-lactone acetate (10)

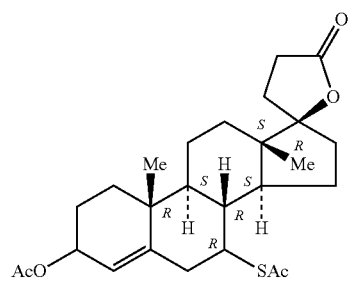

Absolute stereochemistry.
(452920-31-9) (11)

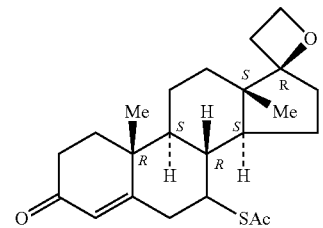

Absolute stereochemistry.
(1260150-03-5) (12)

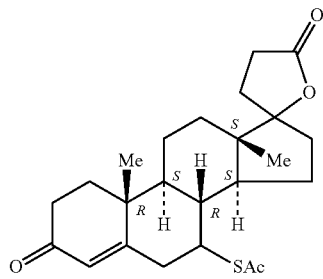

Absolute stereochemistry.
(1301717-71-4) (13)

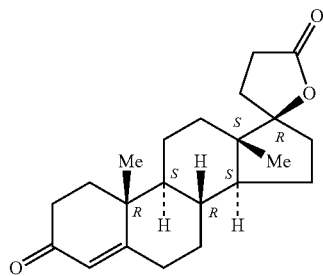

Absolute stereochemistry.
(976-70-5) 6,7-Dihydrocanrenone (14)

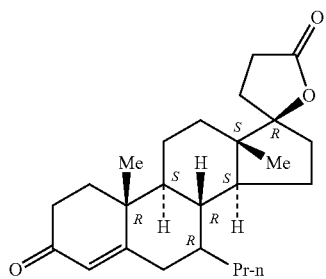

Absolute stereochemistry.
(76676-33-0) RU 26752 (15)

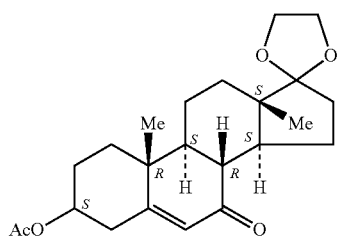

Absolute stereochemistry., Rotation (-).
(40573-86-2) 3β-Acetoxy-17-ethylenedioxy-5-androsten-7-one (16)

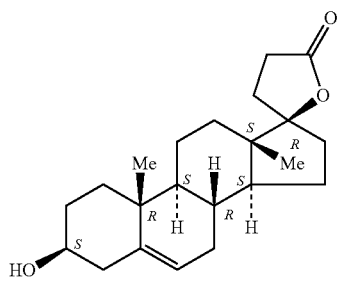

Absolute stereochemistry., Rotation (-).
(13934-61-7) Andrenolactone (17)

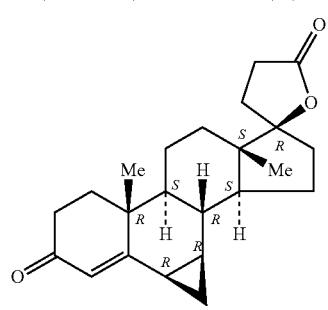

Absolute stereochemistry.
(40574-52-5) Prorenone (18)

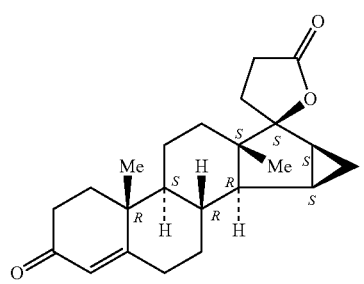

Absolute stereochemistry.
(67372-68-3) 6,7-Desmethylenedrospirenone (19)

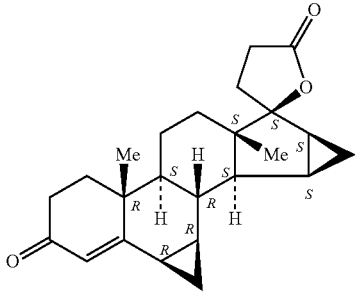

Absolute stereochemistry., Rotation (-).
(67392-87-4) Dihydrospirorenone (20)

RXR-Alpha Antagonists of the Invention

The present invention also encompasses antagonists of RXR-alpha. In a preferred embodiment, such antagonists of RXR-alpha do not inhibit RXR-gamma.

In one embodiment, the present invention provides antagonists of RXR-alpha which inhibit RXR-alpha gene expression and/or RXR-alpha protein production. Non-limiting examples of such inhibitors include, e.g., interfering RNA (e.g., siRNA or shRNA), dsRNA, RNA polymerase III transcribed DNAs, ribozymes, and antisense nucleic acids.

Antisense oligonucleotides, including antisense DNA, RNA, and DNA/RNA molecules, act to directly block the translation of mRNA by binding to targeted mRNA and preventing protein translation. Preferably, antisense oligonucleotides are of at least about 15 bases and are complementary to unique regions of the target DNA sequence. Such antisense oligonucleotides can be synthesized, e.g., by conventional techniques (see, e.g., Dallas et al., (2006) Med. Sci. Monit. 12(4):RA67-74; Kalota et al., (2006) Handb. Exp. Pharmacol. 173:173-96; Lutzelburger et al., (2006) Handb. Exp. Pharmacol. 173:243-59).

siRNA comprises a double stranded structure typically containing 15 to 50 base pairs and preferably 21 to 25 base pairs and having a nucleotide sequence identical or nearly identical to an expressed target gene or RNA within the cell. In one specific embodiment, the antagonist of RXR-alpha is siRNA which comprises the sequence GGGAGAAGGUC-UAUGCGUC (SEQ ID NO: 1). In one specific embodiment, the antagonist of RXR-alpha is siRNA which consists of the sequence GGGAGAAGGUCUAUGCGUC (SEQ ID NO: 1).

RNA polymerase III transcribed DNAs contain promoters, such as the U6 promoter. These DNAs can be transcribed to produce small hairpin RNAs in the cell that can function as siRNA or linear RNAs that can function as antisense RNA. The inhibitor may be polymerized in vitro, recombinant RNA, contain chimeric sequences, or derivatives of these groups. The inhibitor may contain ribonucleotides, deoxyribonucleotides, synthetic nucleotides, or any suitable combination such that the target RNA and/or gene is inhibited. In addition, these forms of nucleic acid may be single, double, triple, or quadruple stranded. (see for example Bass (2001) Nature, 411, 428 429; Elbashir et al., (2001) Nature, 411, 494 498; and PCT Publication Nos. WO 00/44895, WO 01/36646, WO 99/32619, WO 00/01846, WO 01/29058, WO 99/07409, WO 00/44914).

Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hammerhead motif ribozyme molecules that specifically and efficiently catalyze endonucleolytic cleavage of mRNA sequences are also within the scope of the present invention. Scanning the target molecules for ribozyme cleavage sites that include the following sequences, GUA, GUU, and GUC initially identifies specific ribozyme cleavage sites within any potential RNA target. Once identified, short RNA sequences of between about 15 and 20 ribonucleotides corresponding to the region of the target gene containing the cleavage site can be evaluated for predicted structural features such as secondary structure that may render the oligonucleotide sequence unsuitable. The suitability of candidate targets can also be evaluated by testing their accessibility to hybridization with complementary oligonucleotides using, e.g., ribonuclease protection assays.

Expression inhibitors of the present invention can be prepared by known methods. These include techniques for chemical synthesis such as, e.g., by solid phase phosphoamite chemical synthesis. Alternatively, antisense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. See, e.g., Weintraub, H. et al., Antisense RNA as a molecular tool for genetic analysis, Reviews—Trends in Genetics, Vol. 1 (1) 1986.

Various modifications to the oligonucleotides can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Aptamers nucleic acid sequences are readily made that bind to a wide variety of target molecules. The aptamer nucleic acid sequences useful in the methods of the invention can be comprised entirely of RNA or partially of RNA, or entirely or partially of DNA and/or other nucleotide analogs. Aptamers are typically developed to bind particular ligands by employing known in vivo or in vitro (most typically, in vitro) selection techniques known as SELEX (Systematic Evolution of Ligands by Exponential Enrichment). Methods of making aptamers are described in, for example, Ellington and Szostak (1990) Nature 346:818, Tuerk and Gold (1990) Science 249:505, U.S. Pat. No. 5,582,981; PCT Publication No. WO 00/20040; U.S. Pat. No. 5,270,163; Lorsch and Szostak (1994) Biochem. 33:973; Mannironi et al., (1997) Biochem. 36:9726; Blind (1999) Proc. Nat'l. Acad. Sci. USA 96:3606-3610; Huizenga and Szostak (1995) Biochem. 34:656-665; PCT Publication Nos. WO 99/54506, WO 99/27133, and WO 97/42317; and U.S. Pat. No. 5,756,291.

The present invention also encompasses various small molecule inhibitors of RXR-alpha gene expression and/or RXR-alpha protein function. Small molecules are a diverse group of synthetic and natural substances generally having low molecular weights (preferably less than about 2000 Daltons, less than about 1000 Daltons, or less than about 500 Daltons). Small molecules, without limitation, may be, for example, nucleic acids, peptides, polypeptides, peptide nucleic acids, peptidomimetics, carbohydrates, lipids, or other organic (carbon containing) or inorganic molecules and may be synthetic or naturally occurring or optionally derivatized. Such small molecules may be a therapeutically deliverable substance or may be further derivatized to facilitate delivery or targeting.

Some RXR-alpha inhibitors useful in the methods of the present invention are known in the art. See, e.g., PCT Publication No. WO 2012/112623.

The above compounds may be obtained by methods known to skilled practitioners, including the methods disclosed in documents cited herein.

Additional RXR-alpha inhibitors can be isolated from natural sources (for example, plants, fungi, microbes and the like) or isolated from random or combinatorial chemical libraries of synthetic or natural compounds, or synthesized. See Werner et al., (2006) Brief Funct. Genomic Proteomic 5(1):32-6. Many random or combinatorial libraries are known in the art that can be used. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (N.C.), or are readily producible. Additionally, natural and synthetically produced libraries and compounds are readily modified through conventional chemical, physical, and biochemical means (Blondelle et al., (1996) Tib Tech 14:60).

Methods for preparing libraries of molecules are well known in the art and many libraries are commercially available. Libraries of interest in the invention include peptide libraries, randomized oligonucleotide libraries, synthetic organic combinatorial libraries, and the like. Degenerate peptide libraries can be readily prepared in solution, in immobilized form as bacterial flagella peptide display libraries or as phage display libraries. Peptide ligands can be selected from combinatorial libraries of peptides containing at least one amino acid. Libraries can be synthesized of peptoids and non-peptide synthetic moieties. Such libraries can further be synthesized which contain non-peptide synthetic moieties, which are less subject to enzymatic degradation compared to their naturally-occurring counterparts. Libraries are also meant to include for example but are not limited to peptide-on-plasmid libraries, polysome libraries, aptamer libraries, synthetic peptide libraries, synthetic small molecule libraries and chemical libraries. The libraries can also comprise cyclic carbon or heterocyclic structure and/or aromatic or polyaromatic structures substituted with one or more of the above-identified functional groups.

Examples of chemically synthesized libraries are described in Fodor et al., (1991) Science 251:767-773; Houghten et al., (1991) Nature 354:84-86; Lam et al., (1991) Nature 354:82-84; Medynski, (1994) BioTechnology 12:709-710; Gallop et al., (1994) J. Medicinal Chemistry 37(9):1233-1251; Ohlmeyer et al., (1993) Proc. Natl. Acad. Sci. USA 90:10922-10926; Erb et al., (1994) Proc. Natl. Acad. Sci. USA 91:11422-11426; Houghten et al., (1992) Biotechniques 13:412; Jayawickreme et al., (1994) Proc. Natl. Acad. Sci. USA 91:1614-1618; Salmon et al., (1993) Proc. Natl. Acad. Sci. USA 90:11708-11712; PCT Publication No. WO 93/20242, dated Oct. 14, 1993; and Brenner et al., (1992) Proc. Natl. Acad. Sci. USA 89:5381-5383.

Examples of phage display libraries are described in Scott et al., (1990) Science 249:386-390; Devlin et al., (1990) Science, 249:404-406; Christian, et al., (1992) J. Mol. Biol.

227:711-718; Lenstra, (1992) J. Immunol. Meth. 152:149-157; Kay et al., (1993) Gene 128:59-65; and PCT Publication No. WO 94/18318.

Screening the libraries can be accomplished by any variety of commonly known methods. See, for example, the following references, which disclose screening of peptide libraries: Parmley and Smith, (1989) Adv. Exp. Med. Biol. 251:215-218; Scott and Smith, (1990) Science 249:386-390; Fowlkes et al., (1992) BioTechniques 13:422-427; Oldenburg et al., (1992) Proc. Natl. Acad. Sci. USA 89:5393-5397; Yu et al., (1994) Cell 76:933-945; Staudt et al., (1988) Science 241:577-580; Bock et al., (1992) Nature 355:564-566; Tuerk et al., (1992) Proc. Natl. Acad. Sci. USA 89:6988-6992; Ellington et al., (1992) Nature 355:850-852; U.S. Pat. Nos. 5,096,815; 5,223,409; and 5,198,346, all to Ladner et al.; Rebar et al., (1993) Science 263:671-673; and PCT Pub. WO 94/18318.

Identification and screening of RXR-alpha antagonists can be further facilitated by X-ray crystallography, neutron diffraction, nuclear magnetic resonance spectrometry, and other techniques for structure determination. These techniques provide for the rational design or identification of inhibitors.

Another class of RXR-alpha antagonists useful in the methods of the invention are inhibitory antibodies. The antibodies for use in accordance with the present invention may be monoclonal or polyclonal as appropriate. The antibody fragments can be also used and include, for example, Fab, Fab', F(ab')$_2$ or Fv fragments. The antibody may be a single chain antibody. Other suitable modifications and/or agents will be apparent to those skilled in the art. Chimeric and humanized antibodies are also within the scope of the invention. It is expected that chimeric and humanized antibodies would be less immunogenic in a human subject than the corresponding non-chimeric antibody. A variety of approaches for making chimeric antibodies, comprising for example a non-human variable region and a human constant region, have been described. See, for example, Morrison et al., Proc. Natl. Acad. Sci. U.S.A. 81,6851 (1985); Takeda, et al., Nature 314,452 (1985), Cabilly et al., U.S. Pat. No. 4,816,567; Boss et al., U.S. Pat. No. 4,816,397; Tanaguchi et al., European Patent Publication EP 171496; European Patent Publication 0173494, United Kingdom Patent GB 2177096B. Additionally, a chimeric antibody can be further "humanized" such that parts of the variable regions, especially the conserved framework regions of the antigen-binding domain, are of human origin and only the hypervariable regions are of non-human origin. Such altered immunoglobulin molecules may be made by any of several techniques known in the art, (e.g., Teng et al., Proc. Natl. Acad. Sci. U.S.A., 80, 7308-7312 (1983); Kozbor et al., Immunology Today, 4, 7279 (1983); Olsson et al., Meth. Enzymol., 92, 3-16 (1982)), and are preferably made according to the teachings of PCT Publication WO92/06193 or EP 0239400. Humanized antibodies can be commercially produced by, for example, Scotgen Limited, 2 Holly Road, Twickenham, Middlesex, Great Britain.

In certain embodiments, anti-idiotypic antibodies can be also used. Anti-idiotypic antibodies recognize antigenic determinants associated with the antigen-binding site of another antibody. Anti-idiotypic antibodies can be prepared against a second antibody by immunizing an animal of the same species, and preferably of the same strain, as the animal used to produce the second antibody. See, e.g., U.S. Pat. No. 4,699,880. In one embodiment, antibodies are raised against RXR-alpha or a portion thereof, and these antibodies are used in turn to produce an anti-idiotypic antibody.

To screen for antibodies which bind to a particular epitope on the antigen of interest (e.g., RXR-alpha), a routine cross-blocking assay such as that described in Antibodies, A Laboratory Manual, Cold Spring Harbor Laboratory, Ed Harlow and David Lane (1988), can be performed. Alternatively, epitope mapping, e.g. as described in Champe et al. (1995) J. Biol. Chem. 270:1388-1394, can be performed to determine whether the antibody binds an epitope of interest.

Additional antibodies useful in the methods of the present invention can be also generated and selected using phage display approach as described, e.g., in U.S. Patent Appl. Publ. No. 2008/0213268.

Antibodies can be further modified to generate antibody mutants with improved physical, chemical and or biological properties over the parent antibody. See, e.g., Amit et al. (1986) Science 233:747-753; Chothia et al. (1987) J. Mol. Biol. 196:901-917; EP 239400B; Cunningham and Wells (1989) Science 244:1081-1085.

Antibodies can be prepared by standard means. See, e.g., Kohler et al., Nature 256:495-497 (1975) and Eur. J. Immunol. 6:511-519 (1976); Milstein et al., Nature 266:550-552 (1977); Koprowski et al., U.S. Pat. No. 4,172,124; Harlow and Lane, "Antibodies: A Laboratory Manual," (Cold Spring Harbor Laboratory: Cold Spring Harbor, N.Y., 1988); and "Current Protocols In Molecular Biology," (Ausubel et al., Eds.; John Wiley & Sons: New York, N.Y., 1991); Kozbar et al., Immunology Today 4:72 (1983)), Cole et al., "Monoclonal Antibodies and Cancer Therapy" (Alan R. Liss, Inc. pp. 77-96 (1985)); Cabilly et al., U.S. Pat. No. 4,816,567; Winter, U.S. Pat. No. 5,225,539; Cabilly et al., European Patent No. 0,125,023; Boss et al., U.S. Pat. No. 4,816,397; Boss et al., European Patent No. 0,120,694; Neuberger et al., WO 86/01533; Neuberger et al., European Patent No. 0,194,276; Winter, European Patent No. 0,239,400; Newman et al., *BioTechnology* 10:1455-1460 (1992); Ladner et al., U.S. Pat. No. 4,946,778; Bird et al., *Science* 242:423-426 (1988); Kamman et al., Nucl. Acids Res., 17:5404 (1989)); Sato et al., Cancer Research 53:851-856 (1993); Daugherty et al., Nucleic Acids Res. 19(9):2471-2476 (1991); Lewis and Crowe, Gene 101:297-302 (1991); Krebber et al., U.S. Pat. No. 5,514,548; and Hoogenboom et al., WO 93/06213; Jakobovits et al., *Proc. Natl. Acad. Sci. USA* 90:2551-2555 (1993); Jakobovits et al., *Nature* 362:255-258 (1993); Lonberg et al., U.S. Pat. No. 5,545,806; Surani et al., U.S. Pat. No. 5,545,807; Queen et al., European Patent No. 0,451,216; Boss et al., U.S. Pat. No. 4,816,397; Boss et al., European Patent No. 0,120,694; Neuberger et al., WO 86/01533; Padlan et al., European Patent Application No. 0,519,596; Ladner et al., U.S. Pat. No. 4,946,778; and Huston, U.S. Pat. No. 5,476,786.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the

Example 1

NK cells can be an immunotherapy for cancers, including colorectal cancer (Ljunggren & Malmberg. 2007. Nat Rev Immunol 7:329-339). Most studies have focused on extrinsic conditions to optimize missing self-recognition and to activate NK cells (Chan et al. 2012. Clin Cancer Res 18:6296-6305; Fujisaki et al. 2009. Cancer research 69:4010-4017; Rujkijyanont et al. 2013. Cancer research 73:2608-2618). Instead, the applicants here identify new drugs that enhance intrinsic tumor sensitivity to immunotherapy with minimal side effects. By performing a high-throughput screening of a bioactive compound library, it was found that SPIR can upregulate NKG2DL expression in multiple colorectal carcinoma cell lines, thereby enhancing tumor susceptibility to NK cell cytotoxicity.

Although these findings showed a general increase in both mRNA and protein levels of NKG2DLs in SPIR-treated cells, the level of mRNA transcript increase (e.g. MICB in some cell lines such as HT29) did not always correlate with an increase in NKG2DL protein expression on the cell surface. Without being limited to any theory, the reason could be that cell surface expression of NKG2DLs is affected by various post-transcriptional controls such as ligand shedding and intracellular retention (Fuertes et al. 2008. J Immunol 180:4606-4614; Waldhauer & Steinle. 2006. Cancer research 66:2520-2526). NKG2DLs may therefore undergo diverse protein maturation processes in different cell lines that significantly affect protein stability and cell surface expression independent of gene transcription.

Without being limited to any theory, at least one embodiment of the present invention demonstrates that SPIR activates RXR-gamma, which initiates chromatin remodeling, resulting in DNA damage-independent activation of the ATM-Chk2 DNA repair checkpoint pathway that enhances NKG2DL expression. The chromatin decondensation and the establishment of transcription factor "hotspots" induced by activated RXR-gamma facilitates not only NKG2DLs, but also the expression of metastasis suppressor genes such as TIMP2 and TIMP3, which ultimately enhance tumor susceptibility to NK cell cytolysis and inhibit tumor metastasis.

The RXR family consists of three members: RXR-alpha, RXR-beta, and RXR-gamma (Dawson & Xia. 2012. Biochim Biophys Acta 1821:21-56). Various naturally occurring and synthetic retinoids have been identified as RXR ligands. However, due to the observation of numerous side effects upon short- and long-term administration (partly because of their ability to activate multiple RXR members), the systemic use of these agents has been limited (Boehm et al. 1994. J Med Chem 37:2930-2941). Therefore, identification and development of novel, receptor-subtype-specific compounds is critical to improve the therapeutic potential of RXR agonists.

In one embodiment, the present invention demonstrates that SPIR upregulates NKG2DLs specifically by activating RXR-gamma. In another embodiment, specific siRNA knockdown of RXR-alpha (but not RXR-beta or RXR-gamma) enhances the expression of NKG2DLs without SPIR treatment (FIG. 6C-D). Treating HCT116 cells with 9-cis-RA (an agonist that can broadly bind to all members of RXR families) did not induce the upregulation of NKG2DL expression, showing that negative signaling through RXR-alpha overrides the positive effect via RXR-gamma.

Figure 3:
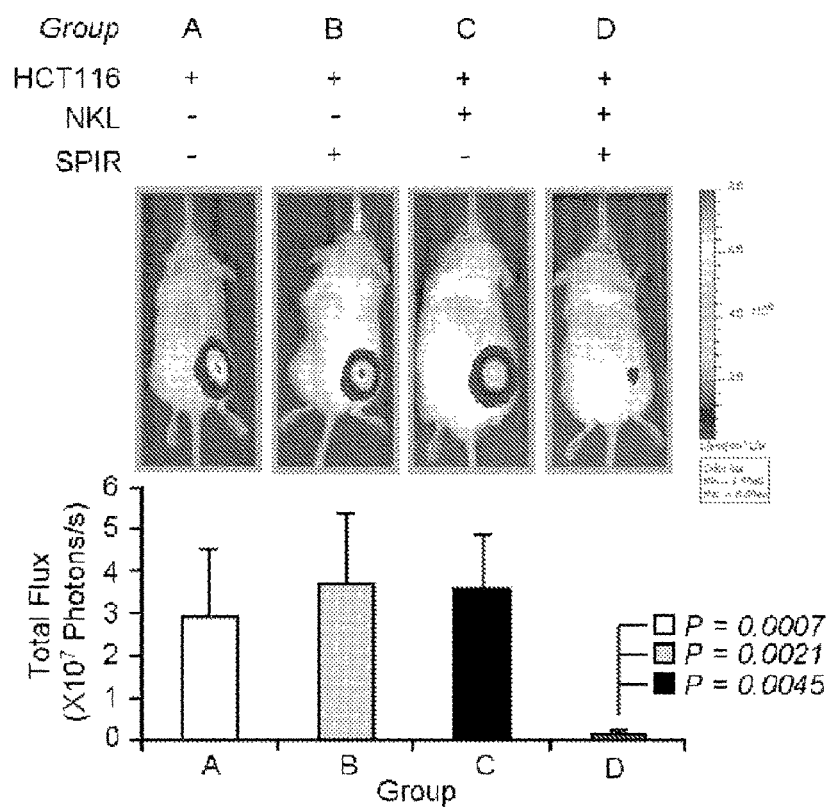
FIG. 3 demonstrates that SPIR exerts antitumor activities in vivo. (A) $1 \times 10^6$ luciferase-expressing HCT116 cells, alone or with $2 \times 10^7$ NKL cells, were subcutaneously injected into 8- to 10-week-old NSG mice (n=4). Two days after the cell injection, SPIR (1.25 mg/mouse) or PBS was intraperitoneally injected into the mice twice a week for 2 weeks. HCT116 xenograft growth was analyzed by performing bioluminescence imaging on day 15. (B) $1 \times 10^6$ HCT116 cells were subcutaneously injected into 8- to 10-week-old NSG mice. Two days after the cell injection, SPIR (1.25 mg/mouse) or PBS was intraperitoneally injected into the mice twice a week for 2 weeks (n=3 per group). Tumor sections were prepared for ULBP2 immunohistochemical staining on day 15. (C) NKG2D expression on the cell surface of YT-INDY and YT-INDY-NKG2D cells was analyzed by flow cytometry. Results are representative of two independent experiments. (D) $1 \times 10^6$ luciferase-expressing HCT116 cells were subcutaneously injected into 8- to 10-week-old NSG mice with either $1 \times 10^6$ YT-INDY or YT-INDY-NKG2D cells (n=8 per group). Two days after the cell injection, SPIR (1.25 mg/mouse) or PBS was intraperitoneally injected into the mice (n=4 per group) twice a week for 2 weeks. HCT116 xenograft growth was analyzed by performing bioluminescence imaging on day 15. (E) MICA-B and ULBP1-3 expressions on the cell surface of HCT116 or HCT116-ΔNKG2DLs cells were analyzed by flow cytometry. Results are representative of two independent experiments. (F) $1 \times 10^6$ luciferase-expressing HCT116 or HCT116-ΔNKG2DLs cells were subcutaneously injected into 8- to 10-week-old NSG mice with $1 \times 10^6$ YT-INDY-NKG2D cells (n=8 per group). Two days after the cell injection, SPIR (1.25 mg/mouse) or PBS was intraperitoneally injected into the mice (n=4 per group) every other day for three times. HCT116 xenograft growth was analyzed by performing bioluminescence imaging on day 10. (G) Eight to ten week-old NSG mice were intraperitoneally injected with PBS or SPIR (1.25 mg per mouse) twice a week for two weeks (n=10 per group). $1 \times 10^6$ each of luciferase-expressing HCT116 cells and YT-INDY-NKG2D were injected subcutaneously into the mice on day 0. HCT116 xenograft growth was analyzed by performing bioluminescence imaging on day 3. * $P<0.05$,  $P<0.01$, * $P<0.005$, **** $P<0.0005$.
Figure 3:
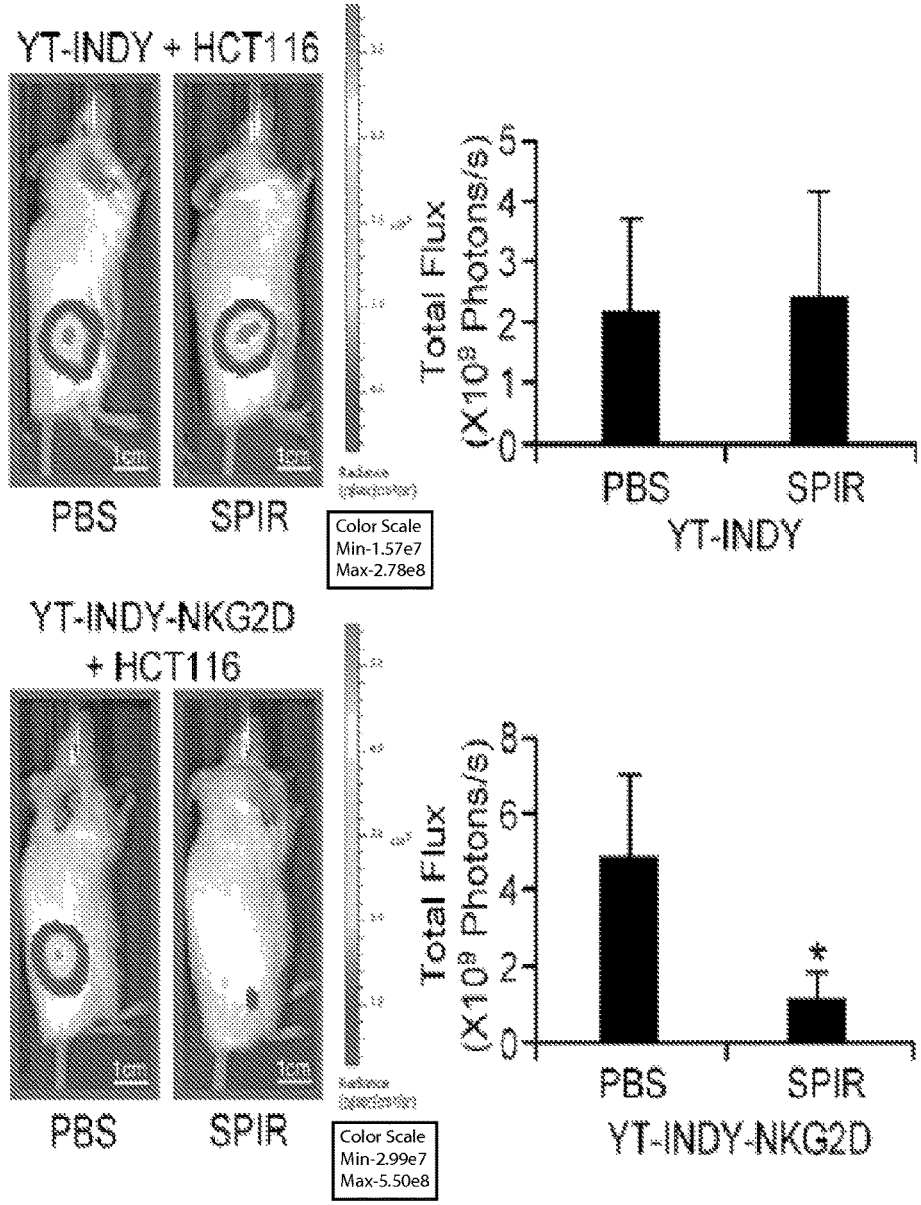
Figure 3:
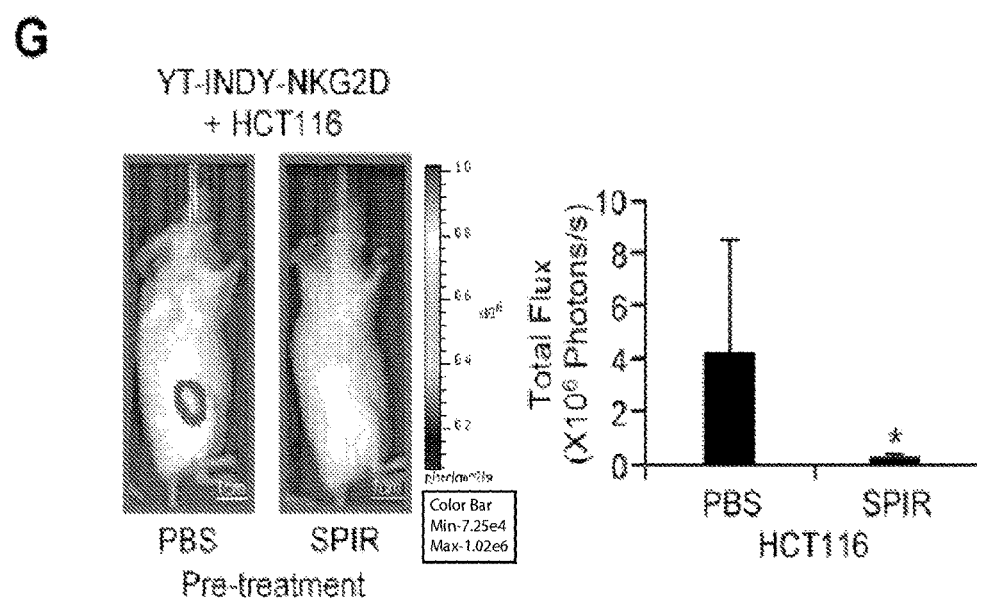
Figure 4:
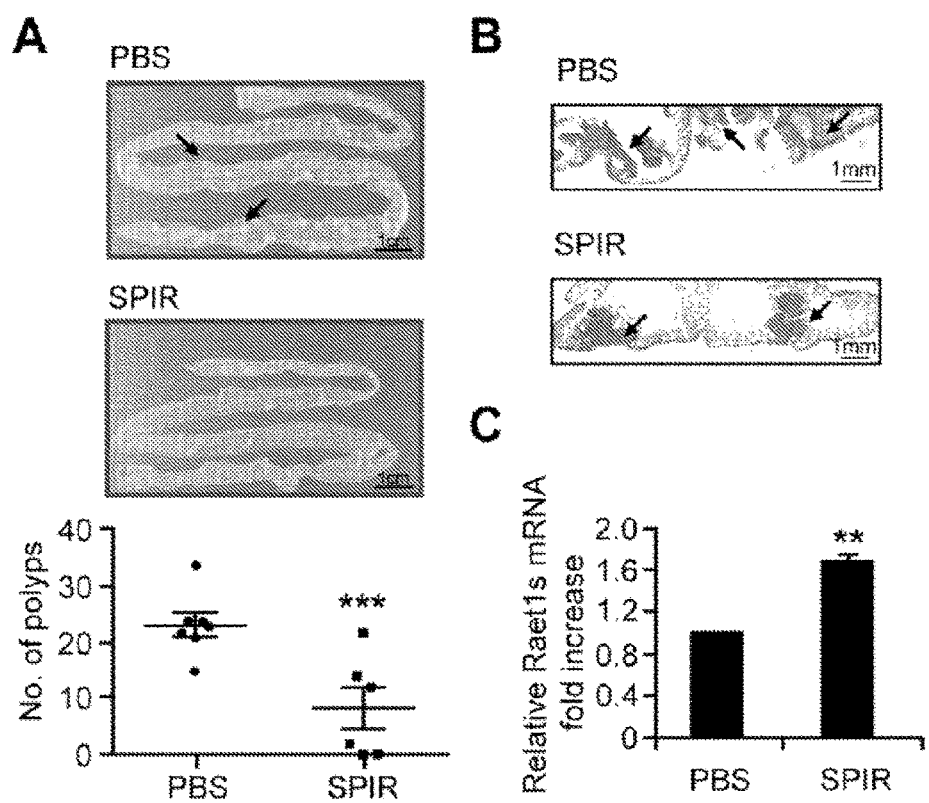
FIG. 4 demonstrates that SPIR treatment acts as both a preventive and a therapeutic in the C57BL/J6J-Apc$^{Min/J}$ Mouse model. (A) 8-week-old C57BL/6J-Apc$^{Min/J}$ mice were given intraperitoneal injections of PBS (n=7) or SPIR (n=6) twice a week for 3 months. The number of spontaneous intestinal polyps (arrows) was counted and compared between the two groups of mice at the end of the 3 month period. (B) The difference in adenoma growth (arrows) between the PBS- and SPIR-treated mouse groups was confirmed in intestine tissue sections. (C) Polyp samples were collected from C57BL/6J-Apc$^{Min/J}$ mice given intraperitoneal injections of PBS or SPIR (n=3 per group) twice a week for two months. Total RNA were collected for cDNA preparation and the expressions of the mouse NKG2D ligands Raet1 family were analyzed by qRT-PCR. (D) Representative appearances of small intestine of 4-month old C57BL/6 (no intestinal polyp) and C57BL/6J-Apc$^{Min/J}$ (displayed obvious polyps—arrows) mice were shown (n=2). (E) Four month-old C57BL/6J-Apc$^{Min/J}$ mice were given intraperitoneal injections of PBS or SPIR (1.25 mg per mouse) (n=5 per group) twice a week for 3 weeks. The number of spontaneous intestinal polyps (arrows) was counted and compared between the two groups of mice. * $P \leq 0.05$,  $P \leq 0.01$, * $P \leq 0.005$.
Figure 4:
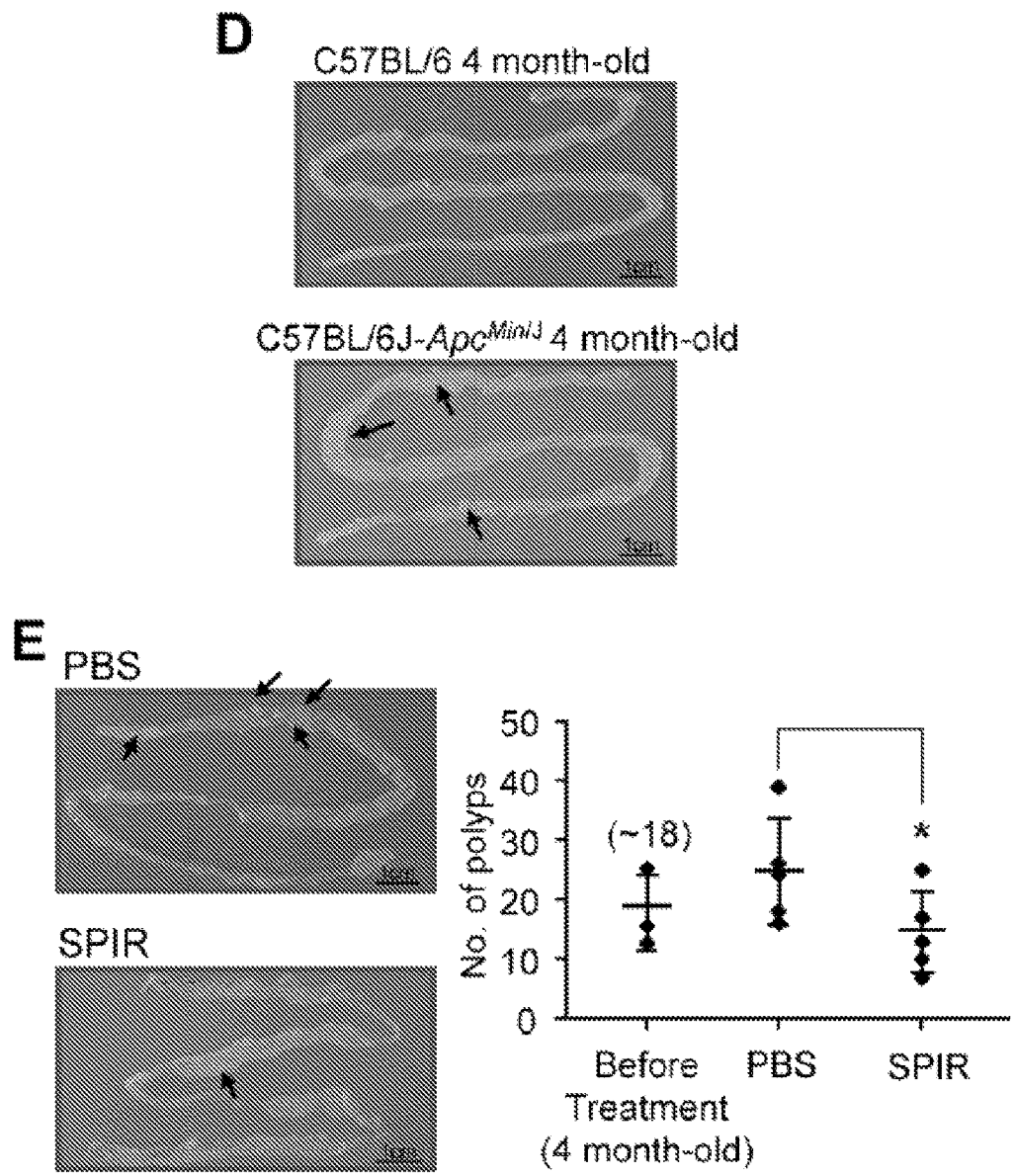

SPIR has been commonly used to treat hypertension and edema and has a good long-term safety record. In the screening phase, it was confirmed that SPIR is safe in mice and observed no detrimental effect on the viability or NKG2DL expression of normal human lymphocytes, suggesting SPIR can act as a safe and effective RXR-gamma-specific modulator in colon cancer therapy. Furthermore, the potential of SPIR in colon cancer prevention in vivo is shown (FIG. 3G and FIG. 4A). Treatment with SPIR for two to twelve weeks successfully achieved a drug level that could prevent colon cancer development in both the NSG and APC mouse model.

Tumor metastasis has been associated with poor prognosis and a low survival rate in colorectal cancer subjects (Cappell, M. S. 2008. Gastroenterol Clin North Am 37:1-24; Murray et al. 1996. Nat Med 2:461-462). This invention demonstrates that administration of SPIR inhibits colon cancer metastasis associated with increased expression of TIMP2 and TIMP3. TIMPs are endogenous protein inhibitors that suppress the activities of MMPs (Brew & Nagase. 2010. Biochim Biophys Acta 1803:55-71) and therefore play a pivotal role in regulating extracellular matrix (ECM) degradation, an essential step in tumor invasion (Visse & Nagase. 2003. Circ Res 92:827-839). The clinical significance of TIMP expression in suppressing metastasis of various types of cancer has been widely reported (Ring et al. 1997. Br J Cancer 76:805-811; Song et al. 2010. J Exp Clin Cancer Res 29:29). Recent studies of gene polymorphisms in TIMP2 and TIMP3 further revealed their associations with tumorigenesis and the cancer survival rate (Malemud, C. J. 2006a. Front Biosci 11:1696-1701; Malemud, C. J. 2006b. Front Biosci 11:1702-1715; Messerli, F. H. 2004. Eur Heart J 25:1475-1476). Increased expression of MMP-1 correlates with poor prognosis and metastasis in colon cancer (Murray et al. 1996. *Nat Med* 2:461-462; Sunami et al. 2000. *Oncologist* 5:108-114). Blockade of its enzyme activity or gene expression inhibits tumor development and metastasis in mouse models (Pulukuri & Rao. 2008. *Int J Oncol* 32:757-765; Vivat-Hannah et al. 2003. Mol Cell Biol. 2003 November 23(21):7678-88.).

In one embodiment, the present invention demonstrates a decrease of MMP-1 activity (FIG. 12) in the culture supernatant from HT29 and CAL27 cells upon SPIR treatment. Without being limited to any theory, decreased MMP-1 activity is postulated to result from the increased expression of TIMP2 and TIMP3.

Materials and Methods

Cell Lines, Mouse Strains, Antibodies, and Reagents.

CAL27, HCT116, HT29, HCT15, SW480, COLO201, LS174T, HepG2, DU145, and RD cell lines were from American Type Culture Collection (ATCC). The NKL cell line is described by Robertson et al., Exp Hematol. 1996 February 24(3):406-15. The YT-INDY cell is described by Kaur et al., Scand J Immunol. 2005 October 62(4):361-70. The anti-ULBP3 (M550) antibody was from Amgen and is described by Cerboni et al., Blood. 2007 Jul. 15 110(2):606-15. NSG and C57BL/6J-Apc$^{Min}$/J mice were from The Jackson Laboratory and are described by Kang et al, Asian Pac J Cancer Prev. 2012 13(4):1115-8. Anti-ULBP1 (AUMO2) and anti-ULBP2 (BUMO1) (as capture antibody for ELISA) antibodies were from BAMOMAB. Allophycocyanin-conjugated anti-ULBP2, anti-MICA, and anti-MICB, blocking antibodies anti-NKG2D (clone 149810)

and anti-NKp30, anti-ULBP2 (IgG2a as detection antibody for ELISA), anti-Chk1 and goat anti-ULBP2 (for Western blot), and human NKG2D-Fc (for flow cytometry) were from R&D Systems. Allophycocyanin-conjugated anti-mouse IgG antibody and HRP-conjugate goat anti-mouse IgG2a were from Jackson ImmunoResearch. Allophycocyanin-conjugated mouse anti-human IgG (Fc) were from Southern Biotech. Anti-MR (N-17) antibody was from Santa Cruz Biotechnology. Anti-ATM, anti-ATR, anti-P-ATR, anti-P-Chk2, and anti-γ-H2A.X antibodies were from Cell Signaling. Anti-tubulin (DM1A+DM1B), anti-H2A.X, anti-Chk2, anti-ATM (Phospho-S 1981) (EP1890Y) antibodies were from Abcam. SPIR, eplerenone, and caffeine were from Sigma. Canrenone, HX531 and KU55933 were from TOCRIS Bioscience. Wortmannin was from Invivogen. VE-821 was from Selleckchem. Human nuclear hormone receptor siRNA library and siRNAs targeting RXR-gamma (siRNA-ID: s200454, s200455, s200456, 251285 and 251287) were from Life Technologies. The control knockdown and prevalidated siRNAs targeting Chk1 and Chk2 were from Cell Signaling. siRNA targeting histone H2A.X was from Qiagen. siRNAs (siGENOME) targeting ATM, ATR, TIMP2, TIMP3, MICA and ULBP3 were from Thermo Scientific. siRNA targeting RXR-alpha was from ThermoScientific (Cat No. D-003443-06; GGGAGAAG-GUCUAUGCGUC [SEQ ID NO: 1]). qRT-PCR primers for mouse Raet1 family (QT01782564: pan-Raet1 primers detecting all members including Raet1a, Raet1b, Raet1c, Raet1d and Raet1e) were from Qiagen.

hauer & Steinle. 2006. Cancer research 66:2520-2526). 100 μl (triplicate) of cultured supernatant was added into a 96-well plate pre-coated with 1 μg/ml of mouse anti-ULBP2 (BUMO1) and incubated at 4° C. overnight. The plate was washed and then incubated with mouse anti-ULBP2 (IgG2a, 100 μl/well at 1 μg/ml) for 1 h followed by incubation with HRP-conjugated goat anti-mouse IgG2a for 1 h at room temperature. TMB substrate was added and the plate was read using Victor$^2$ plate reader (Perkin Elmer).

Cytotoxicity Assay.

Cell lines treated for 5 days with DMSO, SPIR (56 μM), or other agents as indicated were subjected to BATDA release assays (Perkin Elmer) according to the manufacturer's instructions. The results were calculated as follows:

$$\% \text{ specific lysis} = \frac{\text{Experimental release} - \text{Spontaneous release}}{\text{Maximum release} - \text{Spontaneous release}} \times 100.$$

Quantitative Real-Time PCR (qRT-PCR) Assay and Microarray Analysis.

For qRT-PCR, total RNA was extracted from untreated or drug-treated tumor cells by using the RNA Clean & Concentrator (Zymo Research). All cDNA was generated by using the SuperScript VILO cDNA Synthesis kit (Life Technologies) and diluted 10-fold for analysis using the 7900HT Fast Real-time PCR System (Applied Biosystems). The data were calculated as the $C_T$ of target genes normal- Table discloses SEQ ID NOS 2-13, respectively, in order of appearance.

| RXRγ-siRNA | siRNA-ID | Sense sequence (5' to 3') | Anti-sense sequence (5'to 3') |
|---|---|---|---|
| RXRγ-KD1 | s200454 | AAAUGACCCUGUUACCAACtt | GUUGGUAACAGGGUCAUUUgt |
| RXRγ-KD2 | s200455 | GGAUCUCUGGUUAAACACAtt | UGUGUUUAACCAGAGAUCCgg |
| RXRγ-KD3 | s200456 | AGAGGAUUCUAGAAGCUGAtt | UCAGCUUCUAGAAUCCUCUcc |
| RXRγ-KD4 | 251285 | GCAUUAUGCGUGAUUACUGtt | CAGUAAUCACGCAUAAUGCtg |
| RXRγ-KD5 | 251287 | ACUGACGAGUAAACAUGUAtt | UACAUGUUUACUCGUCAGUtc |

RXRγ-siRNAs were obtained from Life technologies.

| TIMPs-siRNA | siRNA-ID | Sense sequence (5' to 3') |
|---|---|---|
| TIMP2-KD | D-011793-17 | GUAAAGAUAAACUGACGAU |
| TIMP3-KD | D-011111-03 | CCGACAUGCUCUCCAAUUU |

TIMP-siRNAs were obtained from ThermoScientific

Flow Cytometry.

Cell lines were stained with allophycocyanin-conjugated anti-MICA, anti-MICB, or anti-ULBP2 antibodies for 20 min at 4° C. For ULBP1 and ULBP3 staining, cells were first incubated with anti-ULBP1 and anti-ULBP3 antibodies and then with allophycocyanin-conjugated goat anti-mouse IgG antibody. To analyze total NKG2DL cell surface expression, cells were first incubated with human NKG2D-Fc for 20 min at 4° C. and then with allophycocyanin-conjugated mouse anti-human IgG (Fc) antibody. Cells were washed and analyzed on a C6 flow cytometer (Accuri). Data were analyzed using FlowJo software (TreeStar).

ULBP2 ELISA.

ULBP2 shed from cell surface to the culture supernatant was detected by ELISA method as described before (Waldized to the $C_T$ of GAPDH of each sample. Primer sequences of the target genes were: MICA-F: 5'-CCTTGGCCAT-GAACGTCAGG-3', (SEQ ID NO: 14) MICA-R: 5'-CCTCTGAGGC-CTCGCTGCG-3', (SEQ ID NO: 15) MICB-F: 5'-ACCTTGGCTATGAACGTCACA-3', (SEQ ID NO: 16) MICB-R:5'-CCCTC-TGAGACCTCGCTGCA-3', (SEQ ID NO: 17), ULBP1-F:5'-ATCAGCGCCTCCTGTC-CAC-3', (SEQ ID NO: 18), ULBP1-R:5'-AAAGACAGT-GTGTGTCGACCCAT-3', (SEQ ID NO: 19), ULBP2-F:5'-AAATGTCACAACGGCCTG-3', (SEQ ID NO: 20), ULBP2-R:5'-TGAGGGGTTCCTTGGG-3', (SEQ ID NO: 21), ULBP3-F:5'-CGATTCTTCCGTACCTGCTA-TTCG-3', (SEQ ID NO: 22), ULBP3-R:AATTCTTCTGATCCAC-CTGGCTCT-3', (SEQ ID NO: 23), TIMP2-F:5'-TCG-GTCTG-AAAGGTGTGGCCTTA-3', (SEQ ID NO: 24), TIMP2-R:AGGTATTTGAGCGGCTTCCTCTGT-3', (SEQ ID NO: 25), TIMP3-F:5'-TCCTGCTACTACCTGCCTGCTTT-3', (SEQ ID NO: 26), TIMP3-R:5'-AGCCAGGGTAACC-GAAATTGGAGA-3' (SEQ ID NO: 27), GAPDH-F: 5'-ATGGGGAAGGTGAAGGTCG3' (SEQ ID NO: 28), GAPDH-R: 5'-G-GGGTCATTGATGGCAACAATA-3' (SEQ ID NO: 29). Microarray analysis was performed using the GeneChip U133 Plus 2.0 expression microarray (Affymetrix) on SPIR (56 µM) treated or untreated (DMSO) HCT116 and CAL27 cells (n=2) (GEO accession no.: GSE50010). Differentially expressed transcripts were analyzed by ANOVA on Spotfire program.

Generation of YT-INDY-NKG2D Cells.

YT-INDY cells were transduced with lentiviral vector MSCV-DAP10-IRES-YFP followed by MSCV-NKG2D-IRES-GFP. GFP and YFP double positive cells were sorted and the surface expression of NKG2D was analyzed by flow cytometry. In vitro validation had confirmed that YT-INDY-NKG2D could kill NKG2DL expressing cells such as K562, Jurkat and HCT116 cells while the parental YT-INDY cells did not.

Generation of HCT116-ΔNKG2DLs cells.

HCT116 cells were transduced with a CMV-driven puromycin-selective lentiviral vector derived from pLL3.7 that contained UL16 sequence (human herpesvirus 5 strain Towne; gene ID: 3077464). Previous reports have shown that UL16 viral proteins interact with various NKG2DLs that interrupt their surface expression (Dunn et al. 2003. J Exp Med 197:1427-1439). Flow cytometry was performed on the puromycin selected cells and it was found that the surface expression of MICB, ULBP1 and ULBP2 was dramatically reduced. Next, the HCT116-UL16 cells were transfected with siRNAs targeting MICA (CCAUGAAC-GUCAGGAAUUU (SEQ ID NO: 30) (ThermoScientific; D-187896-02)) and siRNA targeting ULBP3 (AGGC-UUAGCUCAACCCAAA (SEQ ID NO: 31) (ThermoScientific; D-014353-02)) in order to lower the surface level of MICA and ULBP3 also before injecting the cells into NSG mice for in vivo studies.

In Vivo Xenograft and Metastasis Model.

Luciferase-expressing HCT116 and HT29 cells were generated by lentiviral transduction of the cells with a CMV promoter-driven luciferase expression construct engineered from the pLL3.7 vector. For the HCT116 xenograft model, $1\times10^6$ cells were subcutaneously injected into 8- to 10-week-old NSG mice with or without effector cells (NKL, YT-INDY or YT-INDY-NKG2D cells) followed by the treatment of SPIR as described in figure legends. Bioluminescence imaging was performed in a Xenogen imaging system to monitor tumor growth and the data were analyzed using Living Image software (Caliper LifeSciences). For the lung metastasis model using HT29 cells, lungs were harvested for bioluminescence imaging and then fixed in 10% neutral buffered formalin, paraffin embedded, sectioned, and stained with hematoxylin and eosin. A total of six lung sections at 100-µm intervals were collected for the observation of pulmonary nodules. For the hepatic metastasis model, $0.5\times10^6$ of luciferase-expressing HCT116 cells were intrasplenically implanted into 6-8 week-old NSG mice. Livers were harvested for bioluminescence imaging after SPIR treatment as described in figure legends.

C57BL/6J-Apc$^{Min}$/J Mouse Model.

By examining the intestines collected from different age groups of C57BL/6J-APC$^{Min}$/J mice (n=2-3 per group), it was discovered that none of the 8-week-old mice developed intestinal polyps. The mice started to develop polyps when they were 10 to 12-week-old and there were 15-25 intestinal adenomas established in the intestinal tracts of all the 4-month-old mice. Most of the mice died at 5 to 6 months with 25-30 adenomas in their intestines. SPIR (1.25 mg/mouse) or PBS was intraperitoneally injected into 8-week-old C57BL/6J-Apc$^{Min}$/J mice twice a week for 3 months. The number of intestinal polyps was counted, and the intestine was fixed in 10% neutral buffered formalin, paraffin embedded, sectioned, and stained with hematoxylin and eosin. Intestine sections at 100-µm intervals were collected for the observation of neoplasia without knowledge of treatment assignment.

TIMP2 and TIMP3 ELISA.

Culture supernatant from $2\times10^6$ cells treated 3 days with DMSO or SPIR (56 µM) were collected to determine the protein level of secreted TIMP2 and TIMP3 by ELISA according to the manufacturer's instructions (R&D Systems).

siRNA Transfection.

For the transfection study, $2\times10^5$ cells were transfected with 60 pmol of siRNA molecules using lipofectamine RNAiMAX according to the manufacturer's instructions (Invitrogen).

In Vitro Cell Invasion Assay.

The invasiveness of the tumor cells was determined by using the CytoSelect 96-well Cell Invasion Assay with Basement Membrane (Cell Biolabs) according to the manufacturer instructions.

Wound-Healing Assay.

Confluent cell layers of CAL27 and HT29 cells with a 500 µm±50 µm gap were formed by using Ibidi culture inserts (RPI Corp.). Gap distances were measured at various times using a Nikon Eclipse Ti inverted microscope and NIS-Elements software (Nikon).

RXR-Gamma Reporter Assay.

The Cignal RXR reporter assay system containing an RXR-gamma-responsive luciferase construct, which encodes the firefly luciferase reporter gene under the control of a minimal CMV promoter and tandem repeats of the RXR-gamma transcriptional response element, was purchased from Qiagen. The experiment was performed in HCT116 cells according to the manufacturer's instructions.

Phospho-Chk1 ELISA.

Ser-317 phosphorylation of Chk1 was determined by using the PathScan phosphor-Chk1 (Ser317) Sandwich ELISA kit (Cell Signaling). Data were normalized to the total Chk1 levels obtained from an ELISA with anti-Chk1 (total) used as the detection antibody.

Comet Assay.

HCT116 cells treated with SPIR (56 µM) or etoposide (20 µM) for 24 h or exposed to UV irradiation for 2 h were assayed by using the OxiSelect comet assay kit (Cellbiolabs). Experiments were performed according to the manufacturer's instructions.

Results

SPIR Upregulates NKG2DL Expression in Multiple Colorectal Carcinoma Cell Lines.

In a high-throughput screening of 5600 bioactive compounds, the surface expression of an NKG2DL, ULBP2, was significantly increased in 293T cells in the presence of the aldosterone antagonist SPIR. Therefore, it was further investigated whether SPIR could increase NKG2DL expression on 4 representative colorectal carcinoma cell lines (HCT116, HT29, SW480, and HCT15) covering the most common tumorigenic mutations (Table 1).

TABLE 1

Table 1: Information on the colon cancer cell lines that were used.

| Cell-line | Dukes' Type | Gender | Tumor suppressor genes mutations | | | Oncogene mutations K-Ras |
|---|---|---|---|---|---|---|
| | | | P53 | APC | beta-catenin | |
| HCT116 | n/a | M | − | − | + | + |
| HT29 | n/a | F | + | | | |
| SW480 | B | M | + | + | − | + |
| HCT15 | C | M | + | + | − | + |
| COLO201 | D | M | + | + | + | + |
| LS174T | B | F | + | − | + | + |

Figure 1:
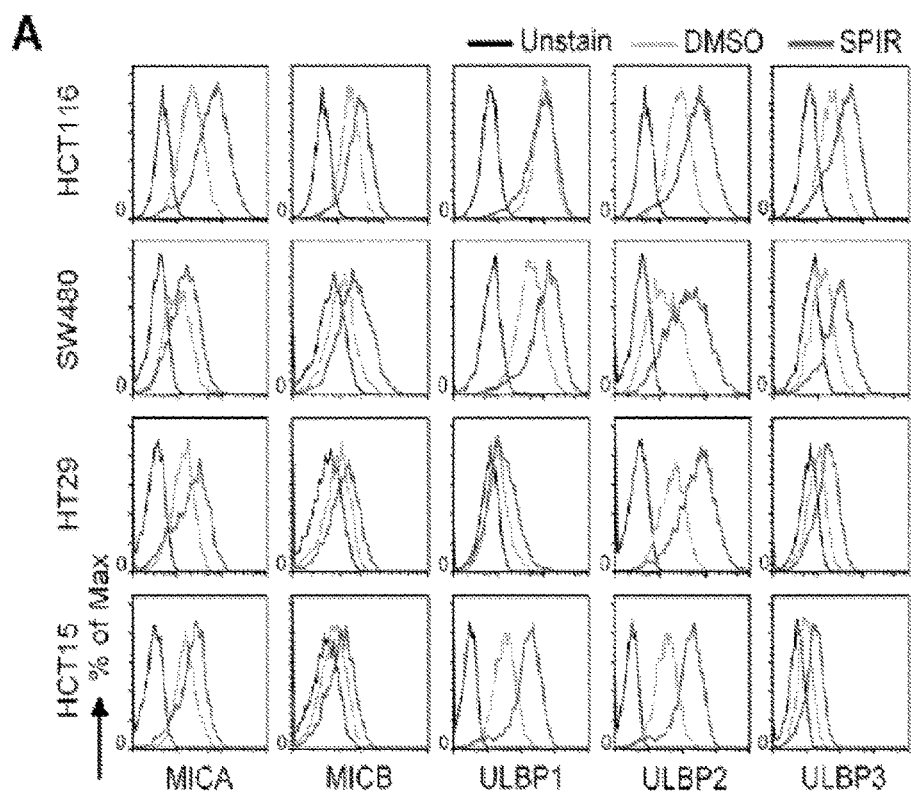
FIG. 1 demonstrates that SPIR upregulates NKG2DL expression. (A) Cell surface expression of MICA-B and ULBP1-3 was analyzed by flow cytometry in multiple colon cancer cell lines treated with DMSO (solvent control) or SPIR (56 µM) for 3 days. Data are representative of five independent experiments. (B) NKG2D-Fc staining was performed to evaluate the change of total NKG2DL expression in the colon cancer cell lines upon SPIR treatment. Controls were stained with APC-conjugated anti-human Fc antibody alone without preincubation with NKG2D-Fc. Data are representative of three independent experiments. (C) DNAM1 ligands (CD112 and CD155), Fas and HLA-ABC surface expressions on HCT116 cells treated with DMSO or SPIR (56 µM) for 3 days were analyzed by flow cytometry. Results are representative of two independent experiments. (D) Shedding of ULBP2 to the culture supernatant from SPIR treated (56 µM for 3 days) or untreated HCT116 cells was detected by ELISA (n=3). (E) NKG2DL mRNA expression in the colon cancer cell lines was analyzed by qRT-PCR analysis. Data are normalized to GAPDH mRNA levels and are presented as fold-change relative to the expression in DMSO-treated cells (n=5). (F) Lentiviral-based luciferase reporter construct containing the putative ULBP2 promoter (−2415 to 0 bp from the transcription start site: 73 bp upstream of ATG) was transduced into the colon cancer cell lines. Positively transduced cells were selected by puromycin treatment (2 µg/ml) for 2 weeks. (G) Luciferase activities of the colon cancer cell lines transfected with the putative ULBP2 promoter construct were determined 3 days after DMSO or SPIR treatment. Data shown are expressed as fold-change relative to the luciferase activity observed in DMSO-treated cells (n=3). * P<0.05, ** P<0.01.
Figure 1:
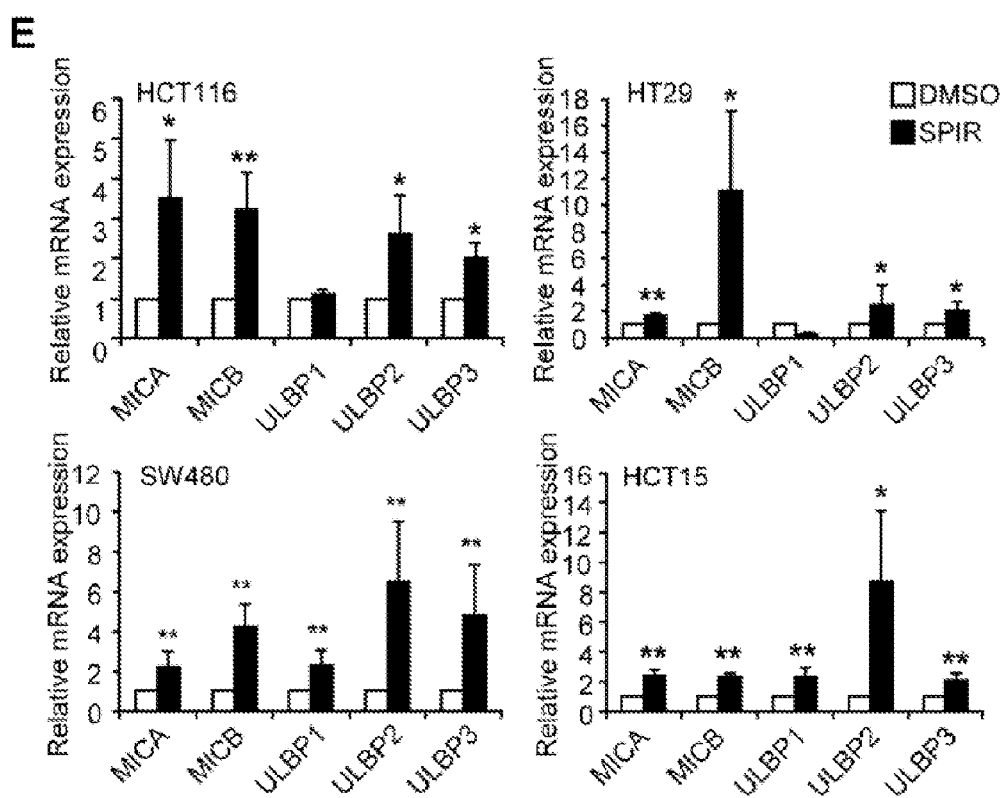

Consistent with the screening results in 293T cells, SPIR treatment significantly increased ULBP2 expression in all cancer cell lines (FIG. 1A) in a dose-dependent manner without affecting the viability of the cells. An enhancement was also observed of MICA/B and ULBP3 expression in all SPIR-treated cells and a selective increase of ULBP1 expression in SW480 and HCT15 cells. Consistent NKG2DL upregulation was also observed by staining the SPIR-treated colon cancer cell lines with soluble NKG2D-Fc molecules (FIG. 1B). However, there was no increase in expression of other NK cell ligands such as DNAM-1 ligands (CD112 and CD155), Fas and HLAs in SPIR-treated HCT116 cells (FIG. 1C), indicating that the upregulation of NKG2DLs by SPIR was specific. A similar increase in NKG2DL expression was observed upon SPIR treatment in 2 other colorectal carcinoma cell lines (COLO201 and LS174T) and in other types of human cancer cells, including head and neck squamous cell carcinoma (CAL27), prostate cancer (DU145), hepatocellular carcinoma (HepG2), and rhabdomyosarcoma (RD), but not in normal cells such as peripheral blood mononuclear cells.

Ligand shedding mediated by metalloproteinases has been observed in various types of cancer (Waldhauer et al. 2008. Cancer research 68:6368-6376; Waldhauer & Steinle. 2006. Cancer research 66:2520-2526). The amount of soluble ULBP2 was compared between the culture supernatant of SPIR-treated or untreated HCT116 cells by ELISA. As shown in FIG. 1D, SPIR treatment did not reduce but rather moderately increased the amount of soluble ULBP2 from HCT116 cells. Quantitative real-time polymerase chain reaction (qRT-PCR) assays showed an increase in mRNA levels (FIG. 1E) corresponding to the enhanced surface expression of NKG2DLs. A significant increase in luciferase activity was also observed (~1.5-fold to 3-fold over the solvent control, DMSO treatment) in all SPIR-treated colon cancer cell lines bearing a luciferase reporter construct driven by a putative ULBP2 promoter (FIG. 1F-G). Taken together, these data show that SPIR upregulates NKG2DL expression by promoting gene transcription and protein production rather than by inhibiting shedding.

SPIR Enhances Tumor Cell Sensitivity to NK Cell-Mediated Cytolysis.

To determine whether the increased expression of NKG2DLs induced by SPIR enhanced tumor cell lysis by NK cells, NK cell cytotoxicity was evaluated in drug-treated or untreated cells by using the NKG2D-expressing NK cell line NKL (FIGS. 2A-B) and interleukin-2-activated primary NK cells (FIG. 2C). Upon SPIR treatment, the susceptibility of all cell lines to NKL lysis was significantly increased. Similarly, treatment of the HT29 and SW480 cells with SPIR markedly enhanced their susceptibility to primary NK cell-mediated lysis.

To verify that the enhancement of tumor cell lysis directly correlated with increased NKG2DL expression, ULBP2 was overexpressed in HCT116 cells by lentiviral transduction (FIG. 2D). As shown in FIG. 2E, increased expression of ULBP2 rendered HCT116 cells more susceptible to NKL-mediated lysis. Additionally, the enhancement of NK cell cytotoxicity against SPIR-treated HCT116 cells was completely abolished in the presence of blocking antibodies against NKG2D but not with those against NKp30 (an activating receptor that induces NK cell cytotoxicity independent of NKG2D/NKG2DL interactions (Andre et al. 2004. Eur J Immunol 34:961-971) (FIG. 2F-G). This result shows the direct involvement of the NKG2D/NKG2DL interaction in NK-mediated lysis of the SPIR-treated cells.

SPIR Exerts Antitumor Activities In Vivo.

To evaluate the in vivo antitumor efficacy of SPIR, a xenograft mouse model was established (luciferase-expressing HCT116 cells in NOD-SCID gamma [NSG] mice) and bioluminescence imaging was performed to monitor tumor growth. HCT116 cells were injected with or without NKL cells subcutaneously into NSG mice. The mice were untreated or treated with SPIR 2 days after the tumor implantation (twice a week for 2 weeks before tumor imaging). As shown in FIG. 3A, the treatment with SPIR alone (group B) or NKL alone (group C) did not affect tumor growth in the mice. However, injecting SPIR into the mice bearing NKL cells (group D) suppressed tumor growth considerably. In line with the in vitro data, SPIR injection significantly enhanced ULBP2 expression in the HCT116 xenografts (FIG. 3B).

To confirm that the in vivo antitumor effect of SPIR depends on the expression of NKG2D in NK cells, another HCT116 xenograft model was established with either NKG2D-negative NK cell line YT-INDY or YT-INDY stably expressing NKG2D (YT-INDY-NKG2D) (FIG. 3C). As shown in FIG. 3D, SPIR treatment did not reduce the HCT116 xenograft growth in YT-INDY-bearing mice. The drug treatment however, strongly suppressed the tumor growth in the presence of YT-INDY-NKG2D. To further confirm that the in vivo antitumor effect of SPIR also requires the increased surface expression of NKG2DLs in tumor cells, NKG2DL-deficient HCT116 cells (HCT116-ΔNKG2DLs) were generated (FIG. 3E). As shown in FIG. 3F, decreased surface expression of NKG2DLs in HCT116 cells significantly reduced tumor susceptibility to NK cell killing triggered by SPIR in vivo. Collectively, these data show that SPIR increases NKG2DL expression in tumor cells in vivo, thereby enhancing NKG2D-dependent tumor control by NK cells. Moreover, pretreating NSG mice with SPIR twice a week for 2 weeks before HCT116 and YT-INDY-NKG2D implantation greatly inhibited tumor development (FIG. 3G), indicating that SPIR also serves as a cancer prevention drug.

To further explore the potential of SPIR in colon cancer prevention and therapy in vivo, the present inventors studied the C57BL/6J-Apc$^{Min}$/J mice, an APC-mutated strain that is highly susceptible to spontaneous intestinal neoplasia formation (Su et al. 1992. *Science* 256:668-670). For cancer prevention, 8-week-old C57BL/6J-Apc$^{Min}$/J mice (in which polyp development has not yet started) were treated with SPIR twice a week for 3 months. Intestines were collected from the mice for polyp counting and immunohistochemistry (FIGS. 4A-B). The number of polyps formed in SPIR-treated mice was significantly less than that in untreated mice. The polyp samples from SPIR-treated or untreated mice were then collected to prepare cDNA for qRT-PCR. As shown in FIG. 4C, SPIR treatment significantly increased the expression of the Raet1 ligand in the polyps (either Raet1d or Raet1e in the B6 mouse background) (Nausch & Cerwenka. 2008. Oncogene 27:5944-5958) showing SPIR-mediated NKG2DL-upregulation similar to that observed in the previous human xenograft models. To further explore the therapeutic potential of SPIR in this model, 4-month-old C57BL/6J-Apc$^{Min}$/J mice that had already developed intestinal polyps (FIG. 4D) were treated with SPIR twice a week for 3 weeks. A significant reduction of the number of polyps was observed in SPIR-treated mice compared with the untreated controls (FIG. 4E). These findings show SPIR is useful for both colon cancer prevention and treatment.

The Upregulation of NKG2DL Expression by SPIR is Independent of the MR Pathway.

SPIR has long been clinically used as an aldosterone antagonist, competing with aldosterone for interaction with the MR Pathway (Struthers et al. 2008. Clin Cardiol 31:153-158). Using MR expression in 293T cells as a relative standard, both mRNA and protein levels of MR were significantly lower in all the colon cancer cell lines and in CAL27 cells (FIGS. 11A-B). Additionally, shRNA knockdown of MR in 293T cells did not affect the upregulation of ULBP2 upon SPIR treatment (FIG. 11C-D). Treating HCT116 cells with two other potent MR antagonists, canrenone and eplerenone, did not reproduce the phenotypes of enhanced expression of NKG2DL upon SPIR treatment (FIG. 5A), confirming that MR is not involved in SPIR's mechanism of action.

SPIR Acts as an RXR-Gamma Agonist for the Upregulation of NKG2DL Expression and Enhancement of Tumor Susceptibility to NK Cytolysis.

Figure 5:
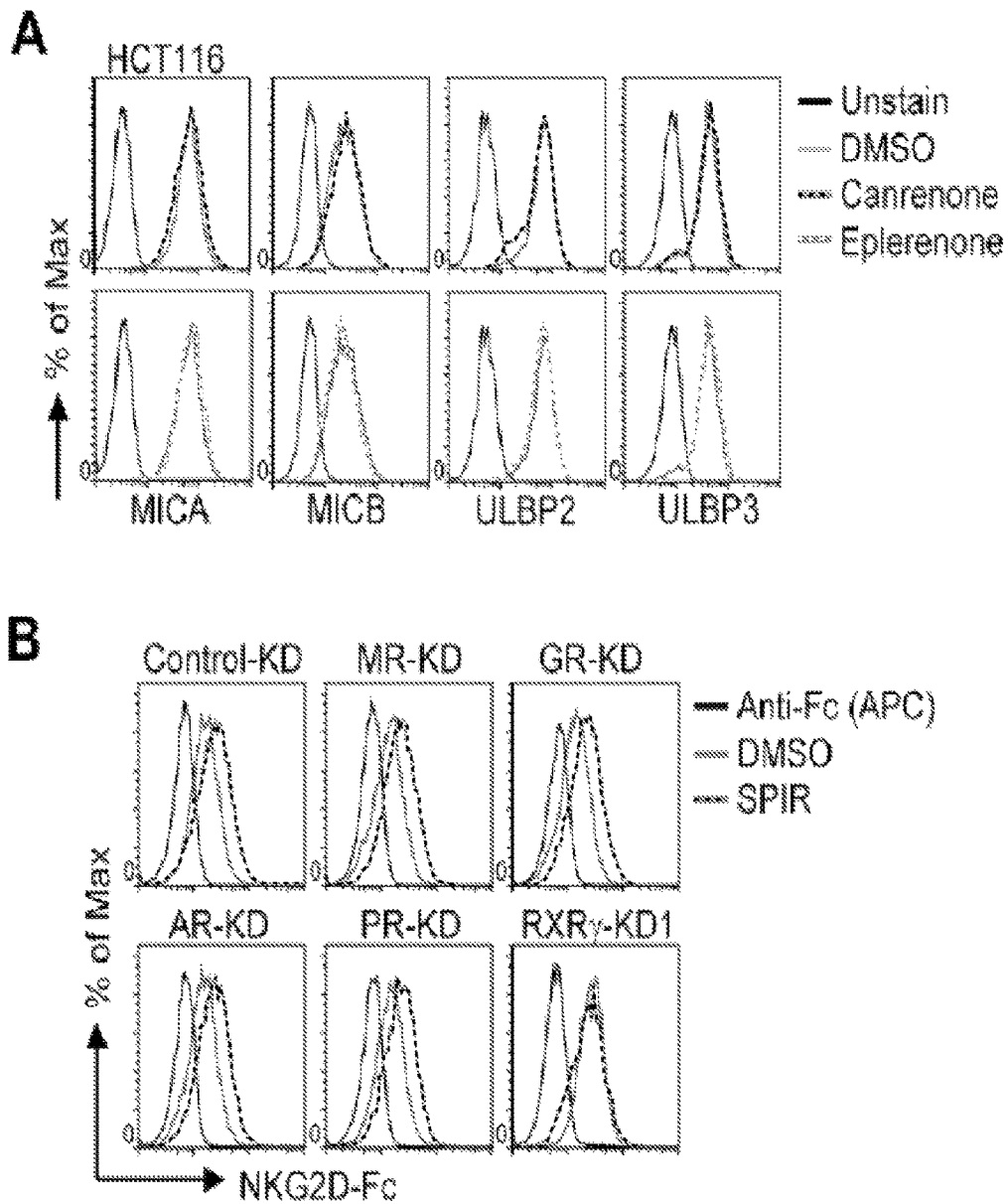
FIG. 5 demonstrates that SPIR exerts its effects on colon cancer through the activation of RXR-gamma but not MR. (A) NKG2DL surface expression was analyzed in HCT116 cells cultured with DMSO, canrenone, or eplerenone for 3 days. Data shown are representative of three independent experiments. (B) NKG2DL expression in control, MR, GR, AR, PR and RXR-gamma knockdown HCT116 cells was compared after DMSO or SPIR treatment (3 days) by NKG2D-Fc staining. Data shown are representative of three independent experiments. (C) The protein level of RXR-gamma was compared between control and RXR-gamma-KD1 HCT116 cells by Western blot analysis. Data shown are representative of two independent experiments. (D) The mRNA expression of RXR-gamma in the carcinoma cell lines was confirmed by using qRT-PCR assays. Data are presented as fold differences relative to the mRNA expression in HCT116 cells (n=2). (E) NKG2DL expression was analyzed in HCT116 cells treated for 3 days with SPIR (56 µM), HX531 (10 µM), or both. Data shown are representative of three independent experiments. (F) Luciferase activity was measured in HCT116 cells transfected with an RXR-gamma-responsive luciferase construct after DMSO or SPIR treatment for 24 h (n=3). (G) The protein expression of RXRγ was compared between DMSO- and SPIR-treated HCT116 cells. Data shown are representative of three independent experiments. (H) HCT116 cells were transfected with control KD or RXR-gamma-KD1 siRNA on day 0. The cells were treated with DMSO or SPIR (56 µM) on day 2. NK cell cytotoxicity on the tumor cells was determined by a BATDA release assay on day 5 using IL-2 (10 U/ml)-primed primary NK cells isolated from healthy donors at various E:T ratios (n=3). (I) Luciferase-expressing HCT116 cells were transfected with either control-KD or RXR-gamma-KD1 siRNA on Day 0. The transfected cells were collected on the next day to inject ($1 \times 10^6$ cells/mouse) subcutaneously into 8- to 10-week-old NSG mice with $1 \times 10^6$ YT-INDY-NKG2D cells (n=8 per group). Two days after the cell injection, SPIR (1.25 mg/mouse) or PBS was intraperitoneally injected into the mice (n=4 per group)
Figure 5:
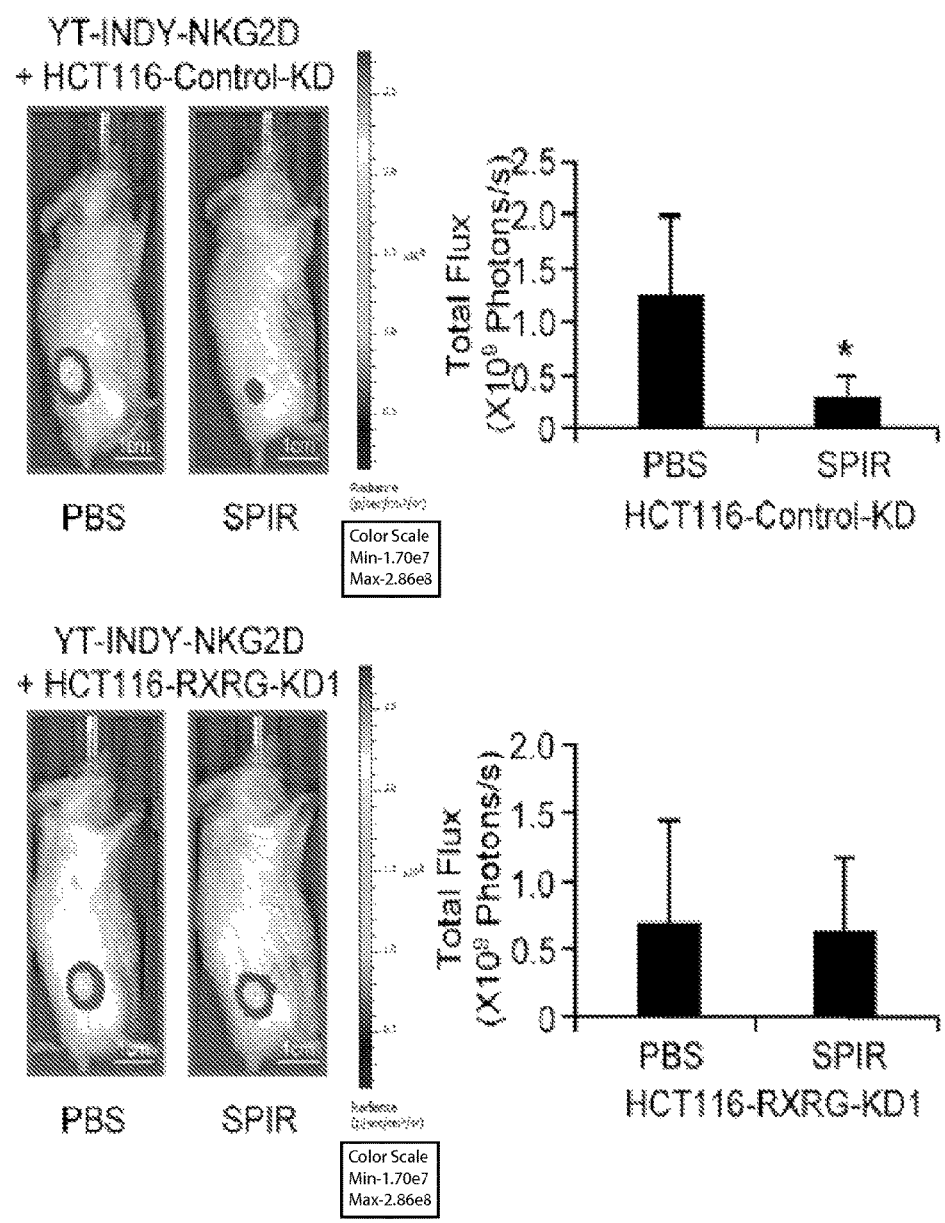

To identify the nuclear hormone receptor (NHR) responsible for the effect of SPIR, an siRNA library (3 specific siRNAs per target gene) was used to target 47 NHRs in HCT116 cells (Table 2). Consistent with previous results (FIG. 11C-D), specific knockdown of MR did not affect NKG2DL upregulation in HCT116 cells by SPIR (FIG. 5B). Although SPIR is also known to interact with glucocorticoid receptor (GR), androgen receptor (AR), and progesterone receptor (PR) (Williams et al. 2006. Endocrinology 147: 2496-2505) none of the siRNAs targeting these NHRs affected the SPIR-mediated NKG2DL upregulation. In contrast, five different siRNAs (3 from the library and 2 added for validation) specifically knocked down the expression of RXR-gamma (Dawson & Xia. 2012. Biochim Biophys Acta 1821:21-56) (FIG. 5C) and significantly reduced SPIR's upregulation of NKG2DLs (FIG. 5B). Consistent with previous reports, RXR-gamma was constitutively expressed in HCT116 cells (FIG. 5C) (Papi et al. 2010. Cancer Lett 297:65-74). Expression of RXR-gamma mRNA was also observed in all other cell lines tested. (FIG. 5D).

To further show that RXR-gamma is directly responsible for SPIR's effect, HCT116 cells were co-treated with SPIR and HX531 which is a specific RXR antagonist (Huang et al. 2011. Nat Neurosci 14:45-53). In line with the siRNA-knockdown results, HX531 treatment significantly reduced SPIR's upregulation of NKG2DLs (FIG. 5E). To further show that RXR-gamma is directly responsible for SPIR's effect, HCT116 cells were transfected with an RXR-gamma-responsive luciferase construct. Upon SPIR treatment, luciferase activity was significantly increased (FIG. 5F), but the RXR-gamma protein level did not change (FIG. 5G). In addition, specific knockdown of RXR-gamma in HCT116 cells significantly reduced the SPIR-mediated enhancement of tumor susceptibility to NK cytolysis both in vitro (FIG. 5H) and in vivo (FIG. 5I). This shows that SPIR functions as an RXR-gamma agonist and confirms the absolute requirement of RXR-gamma for the antitumor effect of SPIR. Surprisingly, by treating HCT116 cells with 9-cis-retinoic acid (9-cis-RA), a high-affinity ligand of RXRs, a decrease was observed (rather than an increase) in NKG2DL expression (FIG. 6A). In fact, from the results of the NHR siRNA library screening, it was found that, although specific knockdown of another RXR family member, RXR-alpha, did not affect the potential of SPIR in upregulating NKG2DL expression in HCT116 cells (FIG. 6B), the gene knockdown by itself without any drug treatment resulted in an increase of NKG2DL expression (FIG. 6C-D). Moreover, with the silencing of RXR-alpha (but not RXR-beta or RXR-gamma), the effect of 9-cis-RA in reducing NKG2DL expression in HCT116 cells was abolished (FIG. 6E). These results show that the activation of RXR-alpha conversely inhibits NKG2DL expression, underscoring the complexity of the RXR family in the regulation of NKG2DLs.

SPIR-Augmented NKG2DL Expression Depends on the ATM-Chk2 Checkpoint Pathway.

It was investigated how SPIR-RXR-gamma signaling regulates the transcription of NKG2DLs. Previous studies have shown that histone deacetylase (HDAC) inhibitors such as sodium valproate can enhance the transcription of MICA/B in various cell lines (Armeanu et al. 2005. Cancer research 65:6321-6329; Diermayr et al. 2008. Blood 111: 1428-1436), and HDAC3 specifically represses ULBP1-3 expression in epithelial tumor cells (Lopez-Soto et al. 2009. Oncogene 28:2370-2382). However SPIR treatment did not inhibit HDAC activities in SW480 or HCT116 cells, and there was no significant change in the mRNA expression of HDAC3 after SPIR treatment, showing that SPIR-RXR-gamma induction of NKG2DL transcription is independent of HDAC.

The DNA-damage checkpoint pathway initiated by ATM/ATR kinases may regulate NKG2DL expression (Gasser et al. 2005. Nature 436:1186-1190; Soriani et al. 2009. Blood 113:3503-3511). In one embodiment, the present invention demonstrates that SPIR treatment induces ATM and ATR phosphorylation (FIG. 7A) in a time-dependent manner that precedes the increase in ULBP2 protein expression (FIG. 7B). To further examine the downstream signaling through ATM/ATR kinases, ELISAs were performed, demonstrating that SPIR-treated HCT116 cells show a time-dependent increase of Ser-317 phosphorylation of Chk1 (P-Chk1) (FIG. 7C) but not the total protein level (FIG. 7D). By Western blot analysis, an increase was also detected in the amount of phosphorylated Chk2 and H2A.X downstream of the ATM/ATR pathway upon SPIR treatment of HCT116 cells (FIG. 7E). Moreover, in the presence of ATM/ATR inhibitors such as caffeine or wortmannin, SPIR's effect on NKG2DL expression was completely abolished in HCT116 (FIG. 7F) and SW480 cells.

To further confirm that ATM and ATR played a role in SPIR-mediated NKG2DL upregulation, HCT116 cells were treated with SPIR together with either an ATM-specific inhibitor, KU55933 or a selective ATR inhibitor, VE-821. Consistent with the ATM/ATR inhibitor treatments described above, KU55933 (10 μM) treatment completely abolished the upregulation of NKG2DLs induced by SPIR. On the contrary, treatment with 10 μM VE-821 only partially reduced the effect of SPIR in NKG2DL expression. Increasing the drug concentration (20 μM) did not further affect NKG2DL expression (FIG. 7F). Furthermore, specific siRNA knockdown of ATM, Chk2 or H2A.X, but not of ATR or Chk1 (FIG. 7G), completely abolishes upregulation of NKG2DL in SPIR-treated HCT116 cells (FIG. 7H). Collectively, this demonstrates that although SPIR activates both ATM and ATR, the ATM-Chk2 but not the ATR-Chk1 pathway is primarily responsible for the upregulation of NKG2DLs.

SPIR Triggers the ATM/ATR Checkpoint Pathway without Causing DNA Damage but Requires the Activation of RXR-Gamma.

Because SPIR has been used widely in the clinic without evidence of inducing DNA breaks or stalled DNA replication, it is unlikely that its induction of ATM/ATR activity is due to a DNA stress response. Despite this, the effect of SPIR on DNA was further investigated. Consistent with the enhanced phosphorylation of multiple signaling molecules in the ATM/ATR checkpoint pathways, an S-phase cell-cycle arrest in was observed in SPIR-treated HCT116 cells (FIG. 8A). However, this cell-cycle arrest was associated with a moderate decrease in DNA breakage rather than an increase, as shown in comet assays (FIG. 8B), indicating that SPIR is not genotoxic. The induction of the ATM/ATR pathways and NKG2DL expression by SPIR requires RXR-gamma activation, as knockdown of RXR-gamma in HCT116 cells diminished the SPIR-induced phosphorylation of ATM, ATR (FIG. 8C), Chk1 (FIG. 8D), Chk2 and H2A.X (FIG. 8E), resulting in less ULBP2 expression.

SPIR Suppresses Motility and Invasiveness of Tumor Cells.

Other genes were identified that are regulated by SPIR in tumor cells. A microarray analysis was performed to compare gene expression between treated and untreated HCT116 and CAL27 cells. Selected gene candidates were then confirmed by qRT-PCR analysis. SPIR significantly upregulated mRNA expression of two metastasis-suppressor genes, TIMP2 and TIMP3 (Albini et al. 1991. J Natl Cancer Inst 83:775-779; Loging & Reisman, 1999. Oncogene 18:7608-7615) in CAL27 and all the colon cancer cell lines (FIG. 9A). ELISAs revealed corresponding increases in TIMP2 and TIMP3 in HCT116 culture supernatant (FIG. 9B). The SPIR-induced expression of TIMPs was independent of the ATM/ATR checkpoint pathways. Gene knockdown of ATM or ATR in HCT116 cells confirmed that the reduction of ATM or ATR expression did not affect the SPIR upregulation of TIMP2 and TIMP3 as determined by qRT-PCR analysis.

The antimetastatic potential of SPIR was examined with HCT116, HT29, and CAL27 cells. SPIR significantly suppressed invasion of the cell lines through extracellular matrix (ECM)-coated membranes in transwell assays (FIG. 9C) and delayed cell migration in wound healing assays (FIG. 9D).

HT29 cells injected subcutaneously into mice are known to metastasize naturally to the lungs (Jojovic and Schumacher, 2000. *Cancer Lett* 152:151-156). In an in vivo metastasis model, bioluminescence imaging (FIG. 9E) and lung tissue sectioning (FIG. 9F) reveals a significant reduction of lung metastasis in NSG mice bearing HT29 xenografts and receiving intraperitoneal injections of SPIR twice a week for 3 weeks.

The Antimetastatic Effect of SPIR is Independent of MR but Requires the Activation of RXR-Gamma.

To test whether the antimetastatic effect of SPIR depended on the MR pathway, the expression of TIMP2 was compared in HCT116 cells treated with SPIR, canrenone, or eplerenone. As shown in FIG. 10A, neither canrenone nor eplerenone upregulated TIMP2 expression. Moreover, treating HCT116 cells with these alternative MR antagonists did not reproduce the suppressive effect of SPIR on cell invasion in ECM-coated transwell assays and cell migration in wound healing assays, showing that SPIR does not modulate tumor metastasis through MR signaling.

In contrast, specific knockdown of RXR-gamma in HCT116 cells not only significantly reduced the effect of SPIR on the upregulation of TIMP2 and TIMP3 (FIG. 10B), but also completely abolished the drug effect on suppressing cell migration in wound healing assays (FIG. 10C) and cell invasion in ECM-coated transwell assays (FIG. 10D). Knockdown of TIMP2 or TIMP3 directly produced effects similar to those of RXR-gamma-KD on cell invasion (FIG. 10D) but had no effects on cell migration (FIG. 10E). These results show that RXR-gamma is essential in both SPIR-mediated suppression of cell invasion and migration and that its role in SPIR-mediated upregulation of TIMP2 and TIMP3 correlated with the inhibition of cell invasion.

In a liver metastasis model (Hamada et al., 2008. Int J Oncol 32:153-159) in which HCT116 cells are implanted into the spleen of 8-week-old NSG mice, SPIR treatment (intraperitoneal injection every other day for 10 days) significantly suppresses tumor metastasis (FIG. 10F). The antimetastatic effect of SPIR is dramatically reduced when RXR-gamma is knocked down in HCT116 cells before intrasplenic injection. These results demonstrate that RXR-gamma is essential for the antimetastatic effect of SPIR.

In summary, described herein is a novel RXR-gamma pathway linking tumor cell-intrinsic NK-cell immunosurveillance and metastasis control. Specifically, the present example demonstrates that SPIR is a potent anticancer agent that favorably regulates NKG2DL and metastasis-suppressor gene expression, enhancing tumor susceptibility to NK cell cytotoxicity and inhibiting metastasis. SPIR's effects are not restricted to colon cancer, being observed also in head and neck, prostate, liver, and smooth muscle cancer cells. This evidence demonstrates that SPIR and other related RXR-gamma agonists are useful to treat and prevent cancer, without causing the side effects of MR inhibition.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

| Lot Number | Plate ID | Sample ID | Plate Name | Location (Row-Col) | Row | Col | RefSeq Accession Number | Gene Symbol | Full Gene Name | Gene ID | siRNA ID | Amount | Exon(s) Targeted | Exon Image | Sense siRNA Sequence | Antisense siRNA Sequence | Matrix 2D Code |
|---|---|---|---|---|---|---|---|---|---|---|---|---|---|---|---|---|---|
| 4397914-AM003 02R-Hm NHR | CPF0 0WB I | AS00E 1FN | Hm NHR siRNA Lib-A1-1 | A1 | A | 1 | NM_0 00475 | NROB 1 | nuclear receptor subfamily 0, group B, member 1 | 190 | s1192 | 0.25 nmole | Not Determined | Not Available | CGAACU UAAUGAG UACCCU Utt | AAGGGU ACUAUU AAGUUC Gat | 00CSI0 7QOI |
| 4397914-AM003 02R-Hm NHR | CPF0 0WB I | AS00E 1FO | Hm NHR siRNA Lib-A1-1 | A2 | A | 2 | NM_0 00044 | AR | androgen receptor | 367 | s1538 | 0.25 nmole | 2, 2 | http:// www. ambion. com/ catalog/ exon_ sirna. php?id= 1538 | GCCCAU UGACUA UUACUU Utt | AAAGUA AUAGUC AAUGGG Caa | 00CSI0 89QF |
| 4397914-AM003 02R-Hm NHR | CPF0 0WB I | AS00E 1FP | Hm NHR siRNA Lib-A1-1 | A3 | A | 3 | NM_0 05234 | NR2F 6 | nuclear receptor subfamily 2, group F, member 6 | 2063 | s4776 | 0.25 nmole | 4 | http:// www. ambion. com/ catalog/ exon_ sirna. php?id= 4776 | UGUGAA AUGUUU GUCUUU Utt | AAAAGA CAAACA UUUCAC Agt | 00CSI0 7SJ8 |
| 4397914-AM003 02R-Hm NHR | CPF0 0WB I | AS00E 1FQ | Hm NHR siRNA Lib-A1-1 | A4 | A | 4 | NM_0 00125 | ESR1 | estrogen receptor 1 | 2099 | s4823 | 0.25 nmole | Not Determined | Not Available | ACAUCA UCUCGG UUGAUG Att | UGCGGA ACCGAG AUGAUG UAg | 00CSI0 7OUL |
| 4397914-AM003 02R-Hm NHR | CPF0 0WB I | AS00E 1FR | Hm NHR siRNA Lib-A1-1 | A5 | A | 5 | NM_0 01040 275 | ESR2 | estrogen receptor 2 (ER beta) | 2100 | s4826 | 0.25 nmole | 4,4,4, | http:// www. ambion. com/ catalog/ exon_ sirna. php?id= 4826 | AGUGUA CAAUCG AUAAAA Att | UUUUUA UCGAUU GUACAC Uga | 00CSI0 7O5V |

-continued

| | | | | | | | | | | | | | | |
|---|---|---|---|---|---|---|---|---|---|---|---|---|---|---|
| 439791 4- AM003 02R-Hm NHR | CPF0 0WB I | AS00E 1FS | Hm NHR siRNA Lib- A1-1 | A6 | A | 6 | NM_0 04451 | ESRR A | estrogen related receptor alpha | 2101 | s4829 | 0.25 nmole | 5 | http:// www. ambion. com/ catalog/ exon_ sirna. php?id= 4829 | UGCUGG UGGUUG AGCCUG Att | UCAGGC UCAACC ACCAGC Aga | 00CSI0 7OGZ |
| 439791 4- AM003 02R-Hm NHR | CPF0 0WB I | AS00E 1FT | Hm NHR siRNA Lib- A1-1 | A7 | A | 7 | NM_0 04452 | ESRR B | estrogen related receptor beta | 2103 | s4832 | 0.25 nmole | Not De- termined | Not Avail- able | UACCUG AGCUUA CAAAUU Utt | AAAUUU GUAAGC UCAGGU Atg | 00CSI0 7061 |
| 439791 4- AM003 02R-Hm NHR | CPF0 0WB I | AS00E 1FU | Hm NHR siRNA Lib- A1-1 | A8 | A | 8 | NM_0 01438 | ESRR G | estrogen related receptor gamma | 2104 | s4838 | 0.25 nmole | 6,8,7 | http:// www. ambion. com/ catalog/ exon_ sirna. php?id= 4835 | GGAUGA ACUUGU CUAUGC Att | UGCAUA GACAAG UUCAUC Ctc | 00CSI0 7064 |
| 439791 4- AM003 02R-Hm NHR | CPF0 0WB I | AS00E 1FV | Hm NHR siRNA Lib- A1-1 | A9 | A | 9 | NM_0 03822 | NR5A 2 | nuclear receptor sub- family 5, group A, member 2 | 2494 | s5380 | 0.25 nmole | 3, 4 | http:// www. ambion. com/ catalog/ exon_ sirna. php?id= 5380 | GUGUUG GAAUGA AGCUAG Att | UCUAGC UUCAUU CCAACAC tt | 00CSI0 7S6W |
| 439791 4- AM003 02R-Hm NHR | CPF0 0WB I | AS00E 1FW | Hm NHR siRNA Lib- A1-1 | A10 | A | 10 | NM_0 04959 | NR5A 1 | nuclear receptor sub- family 5, group A, member 1 | 2516 | s5392 | 0.25 nmole | Not De- termined | Not Avail- able | GCAGGU GCAUGG UCUUCA Att | UUGAAG ACCAUG CACCUG Cgt | 00CSI0 7I67 |

-continued

| | | | | | | | | | | | | | |
|---|---|---|---|---|---|---|---|---|---|---|---|---|---|
| 439791 4-AM003 02R-Hm NHR | CPF0 0WB I | AS00E 1FX | Hm NHR siRNA Lib-A1-1 | AA | A | 11 | NM_0 01489 | NR6A 1 | nuclear receptor sub-family 6, group A, member 1 | 2649 | s5660 | 0.25 nmole | 7,7 | http:// www. ambion. com/ catalog/ exon_ sirna. php?id= 5660 | CCCUCA CCGUUU ACAGCA Att | UUGCUG UAAACG GUGAGG Gaa | 00CSI0 7SAP |
| 439791 4-AM003 02R-Hm NHR | CPF0 0WB I | Empty Well | | A12 | A | 12 | | | | | | | | | | | |
| 439791 4-AM003 02R-Hm NHR | CPF0 0WB I | AS00E 1FY | Hm NHR siRNA Lib-A1-1 | B1 | B | 1 | NM_0 00176 | NR3C 1 | nuclear receptor sub-family 3, group C, member 1 (gluco-corticoid receptor) | 2908 | s6185 | 0.25 nmole | 2,2,2,2, 2,2,2 | http:// www. ambion. com/ catalog/ exon_ sirna. php?id= 6185 | CACUCU CAAUGG GACUGU Att | UACAGU CCCAUU GAGAGU Gaa | 00CSI0 7SLU |
| 439791 4-AM003 02R-Hm NHR | CPF0 0WB I | AS00E 1FX | Hm NHR siRNA Lib-A1-1 | B2 | B | 2 | NM_0 02135 | NR4A 1 | nuclear receptor sub-family 4, group A, member 1 | 3164 | s6678 | 0.25 nmole | 3,2 | http:// www. ambion. com/ catalog/ exon_ sirna. php?id= 6678 | GCACCU UCAUGG ACGGCU Att | UAGCCG UCCAUG AAGGUG Ctg | 00CSI0 7REJ |
| 439791 4-AM003 02R-Hm NHR | CPF0 0WB I | AS00E 1G0 | Hm NHR siRNA Lib-A1-1 | B3 | B | 3 | NM_0 00901 | NR3C 2 | nuclear receptor sub-family 3, group C, member 2 | 4306 | s8838 | 0.25 nmole | Not De-termined | Not Avail-able | CACCAG ACCUAG UCUUUA Att | UUAAAG ACUAGG UCUGGU Gca | 00SCI0 7UF3 |

-continued

| | | | | | | | | | | | | | |
|---|---|---|---|---|---|---|---|---|---|---|---|---|---|
| 439791 4-AM003 02R-Hm NHR | CPF0 0WB I | AS00E 1G1 | Hm NHR siRNA Lib-A1-1 | B4 | B | 4 | NM_1 73172 | NR4A 2 | nuclear receptor sub-family 4, group A, member2 | 4929 | s9785 | 0.25 nmole | Not De-termined | Not Avail-able | CCACGU GACUUU CAACAA Utt | AUUGUU GAAAGU CACGUG Gtc | 00CSI0 7UJJ |
| 439791 4-AM003 02R-Hm NHR | CPF0 0WB I | AS00E 1G2 | Hm NHR siRNA Lib-A1-1 | B5 | B | 5 | NM_0 00926 | PGR | progest-erone receptor | 5241 | s10415 | 0.25 nmole | Not De-termined | Not Avail-able | GGUCCU UGGAGG UCGAAA Att | UUUUCG ACCUCC AAGGAC Cat | 00CSI0 7X00 |
| 439791 4-AM003 02R-Hm NHR | CPF0 0WB I | AS00E 1G3 | Hm NHR siRNA Lib-A1-1 | B6 | B | 6 | NM_0 01001 928 | PPAR A | perox-isome pro-lifer-ator-activated receptor alpha | 5465 | s1088 0 | 0.25 nmole | 7, 8 | http://www.ambion.com/catalog/exon_sirna.php?id=10680 | GAUCAA GUGACA UUGCUA Att | UUAGCA AGUCA CUUGAU Cgt | 00CSI0 7W5D |
| 439791 4-AM003 02R-Hm NHR | CPF0 0WB I | AS00E 1G4 | Hm NHR siRNA Lib-A1-1 | B7 | B | 7 | NM_0 06238 | PPAR D | perox-isome pro-lifer-ator-activated receptor delta | 5467 | s1088 3 | 0.25 nmole | Not De-termined | Not Avail-able | GUGAUA UCAUUG AGCCUA Att | UUAGGC UCAAUG AUAUCA Ctg | 00CSI0 7VJW |
| 439791 4-AM003 02R-Hm NHR | CPF0 0WB I | AS00E 1G5 | Hm NHR siRNA Lib-A1-1 | B8 | B | 8 | NM_0 05037 | PPAR G | perox-isome pro-lifer-ator-activated receptor gamma | 5468 | s1088 6 | 0.25 nmole | 5, 5, 6, 6 | http://www.ambion.com/catalog/exon_sirna.php?id=10886 | GACAAA UCACCA UUCGUU Att | UAACGA AUGGUG AUUUGU Ctg | 00CSI0 7VJZ |
| 439791 4-AM003 02R-Hm NHR | CPF0 0WB I | AS00E 1G6 | Hm NHR siRNA Lib-A1-1 | B9 | B | 9 | NM_0 00964 | RARA | retinoic acid receptor, alpha | 5914 | s11820 | 0.25 nmole | 5, 4 | http://www.ambion.com/catalog/exon_sirna.php?id=11800 | GAACAA CAGCGC AGAACA Att | UUGUUC UGAGCU GUUGUU Cgt | 00CSI0 7VXS |

-continued

| | | | | | | | | | | | | | |
|---|---|---|---|---|---|---|---|---|---|---|---|---|---|
| 439791 4-AM003 02R-Hm NHR | CPF0 0WB I | AS00E 1G7 | Hm NHR siRNA Lib-A1-1 | B10 | B | 10 | NM_0 16152 | RARB | retinoic acid receptor, beta | 5915 | s1180 3 | 0.25 nmole | Not De-termined | Not Avail-able | GAACCG ACAAAA GUAGAU Att | UAUCUA CUUUUG GUAGAU Att | 00CSIO 7VXW |
| 439791 4-AM003 02R-Hm NHR | CPF0 0WB I | AS00E 37F | Hm NHR siRNA Lib-A1-1 | B11 | B | 11 | NM_0 00966 | RARG | retinoic acid receptor, gamma | 5916 | s1180 6 | 0.25 nmole | 6, 4 | http:// www. ambion. com/ catalog/ exon_ sirna. php?id= 11806 | GCUAUG AGCUGA GCCCUC Att | UGAGGG CUCAGC UCAUAG Ctg | 00CSIO 7VXX |
| 439791 4-AM003 02R-Hm NHR | CPF0 0WB I | Empty Well | Hm NHR siRNA Lib-A1-1 | B12 | B | 12 | | | | | | | | | | | |
| 439791 4-AM003 02R-Hm NHR | CPF0 0WB I | AS00E 37G | Hm NHR siRNA Lib-A1-1 | C1 | C | 1 | NM_1 34260 | RORA | RAR-related orphan receptor A | 6095 | s1210 3 | 0.25 nmole | Not De-termined | Not Avail-able | GAAUAU AUCUAA AUCGCA Utt | AUGCGA UUUAGA UAUAUU Ctg | 00CSIO 7X7E |
| 439791 4-AM003 02R-Hm NHR | CPF0 0WB I | AS00E 37H | Hm NHR siRNA Lib-A1-1 | C2 | C | 2 | NM_0 06914 | RORB | RAR-related orphan receptor B | 6096 | s1210 6 | 0.25 nmole | 10 | http:// www. ambion. com/ catalog/ exon_ sirna. php?id= 12106 | CCAUCA CGGCAG UUUGCA Att | UUGCAA ACUGCC GUGAUG Gtt | 00CSIO 7W5X |
| 439791 4-AM003 02R-Hm NHR | CPF0 0WB I | AS00E 37I | Hm NHR siRNA Lib-A1-1 | C3 | C | 3 | NM_0 01001 523 | RORC | RAR-related orphan receptor C | 6097 | s1210 9 | 0.25 nmole | 8, 9 | http:// www. ambion. com/ catalog/ exon_ sirna. php?id= 12109 | CAGCCC UUGUUC UCAUCA Att | UUGAUG AGAACA AGGGCU Gtg | 00CSIO 7X7K |
| 439791 4-AM003 02R-Hm NHR | CPF0 0WB I | AS00E 37J | Hm NHR siRNA Lib-A1-1 | C4 | C | 4 | NM_0 02957 | RXRA | retinoid X receptor alpha | 6256 | s1238 4 | 0.25 nmole | Not De-termined | Not Avail-able | UCGUCC UCUUUA ACCCUG Att | UCAGGG UUAAAG AGGACG Atg | 00CSIO 7X8S |

-continued

| | | | | | | | | | | | | | |
|---|---|---|---|---|---|---|---|---|---|---|---|---|---|
| 439791 4-AM003 02R-Hm NHR | CPF0 0WB I | AS00E 37K | Hm NHR siRNA Lib-A1-1 | C5 | C | 5 | NM_0 21976 | RXRB | retinoid X receptor beta | 6257 | s12387 | 0.25 nmole | 4 | http:// www. ambion. com/ catalog/ exon_sirna. php?id=12387 | CUCUUG CCGGGA CAACAA Att | UUUGUU GUCCCG GCAAGA Gta | 00CSI0 7P8S |
| 439791 4-AM003 02R-Hm NHR | CPF0 0WB I | AS00E 37L | Hm NHR siRNA Lib-A1-1 | C6 | C | 6 | NM_0 05654 | NR2F 1 | nuclear receptor sub-family 2, group F, member 1 | 7025 | s14018 | 0.25 nmole | 2 | http:// www. ambion. com/ catalog/ exon_sirna. php?id=14018 | ACAUUA UGGGCA UCGAGA Att | UUCUCG AUGCCC AUAAUG Utg | 00CSI0 7W65 |
| 439791 4-AM003 02R-Hm NHR | CPF0 0WB I | AS00E 37M | Hm NHR siRNA Lib-A1-1 | C7 | C | 7 | NM_0 21005 | NR2F 2 | nuclear receptor sub-family 2, group F, member 2 | 7026 | s14021 | 0.25 nmole | Not De-termined | Not Avail-able | GCUUUG GAAGAA UACGUU Att | UAACGU AUUCUU CCAAAG Cac | UAACGU AUUCUU CCAAAG Cac |
| 439791 4-AM003 02R-Hm NHR | CPF0 0WB I | AS00E 37N | Hm NHR siRNA Lib-A1-1 | C8 | C | 8 | NM_0 03250 | THRA | thyroid hormone receptor, alpha (erythroblastic leukemia viral (v-erb-a) oncogene homolog, avian) | 7067 | s14116 | 0.25 nmole | 4, 4 | http:// www. ambion. com/ catalog/ exon_sirna. php?id=14116 | CUAGUU ACCUGG ACAAAG Att | UCUUUG UCCAGG UAACUA Ggg | 00CSI0 7W6B |

-continued

| | | | | | | | | | | | | | |
|---|---|---|---|---|---|---|---|---|---|---|---|---|---|
| 439791 4-AM003 02R-Hm NHR | CPF0 0WB I | AS00E 370 | Hm NHR siRNA Lib-A1-1 | C9 | C | 9 | NM_0 00461 | THRB | thyroid hormone receptor, beta (erythroblastic leukemia viral (v-erb-a) oncogene homolog 2, avian) | 7068 | s1411 9 | 0.25 nmole | Not De-termined | Not Avail-able | GCAUGU CUCUGU CUUCUU Utt | AAAGAA GACAGA GACAUG Ccc | 00CSIO 7W6E |
| 439791 4-AM003 02R-Hm NHR | CPF0 0WB I | AS00E 37P | Hm NHR siRNA Lib-A1-1 | C10 | C | 10 | NM_0 03269 | NR2E 1 | nuclear receptor sub-family 2, group E, member 1 | 7101 | s1420 0 | 0.25 nmole | Not De-termined | Not Avail-able | GAAUUU GCCUGU CUAAAA Utt | AUUUUA GACAGG CAAAUU Cag | 00CSIO 7W6H |
| 439791 4-AM003 02R-Hm NHR | CPF0 0WB I | AS00E 37Q | Hm NHR siRNA Lib-A1-1 | C11 | C | 11 | NM_0 01032 287 | NR2C 1 | nuclear receptor sub-family 2n group C, member 1 | 7181 | s1436 7 | 0.25 nmole | Not De-termined | Not Avail-able | CCAUUG AAGUAU CACGAG Att | UCUCGU GAUACU UCAAUG Ggt | 00CSIO 7W6K |
| 439791 4-AM003 02R-Hm NHR | CPF0 0WB I | Empty Well | Hm NHR siRNA Lib-A1-1 | C12 | C | 12 | | | | | | | | | | |
| NHR 439791 4-AM003 02R-Hm NHR | CPF0 0WB I | AS00E 37R | A1-1 Hm NHR siRNA Lib-A1-1 | D1 | D | 1 | NM_0 03298 | NR2C 2 | nuclear receptor sub-family 2, group C, member 2 | 7182 | s1437 0 | 0.25 nmole | 3 | http:// www. ambion. com/ catalog/ exon_ sirna. php?id= 14370 | UGAGUG UUUUCA CAUCUU Utt | AAAGAU GUGAAA ACACUC Aat | 00CSIO 7W6N |

-continued

| | | | | | | | | | | | | |
|---|---|---|---|---|---|---|---|---|---|---|---|---|
| 4397914-AM003-02R-HmNHR | CPF00WBI | AS00E37S | HmNHRsiRNALib-A1-1 | D2 | D | 2 | NM_007121 | NR1H2 | nuclear receptor subfamily 1, group H, member 2 | 7376 | s14684 | 0.25 nmole | 6 | http://www.ambion.com/catalog/exon_sirna.php?id=14684 | GAACAGAUCCGGAAGAAGAtt | UCUUCUUCCGGAUCUGUUCtt | 00CSIO7LYF |
| 4397914-AM003-02R-HmNHR | CPF00WBI | AS00E37T | HmNHRsiRNALib-A1-1 | D3 | D | 3 | NM_000376 | VDR | vitamin D (1,25-dihydroxyvitamin D3) receptor | 7421 | s14777 | 0.25 nmole | 4,5 | http://www.ambion.com/catalog/exon_sirna.php?id=14777 | AGUUCAUUCUGACAGAUGAtt | UCAUCGGUCUGAAUGAAACUcc | 00CSIO7W6P |
| 4397914-AM003-02R-HmNHR | CPF00WBI | AS00E37U | HmNHRsiRNALib-A1-1 | D4 | D | 4 | NM_006981 | NR4A3 | nuclear receptor subfamily 4, group A, member 3 | 8013 | s15541 | 0.25 nmole | 3,3,2 | http://www.ambion.com/catalog/exon_sirna.php?id=15541 | AGAGAACAGUGCAGAAAAAtt | UUUUUCUGCACUGUUCUCUAtg | 00CSIO7W6S |
| 4397914-AM003-02R-HmNHR | CPF00WBI | AS00E37V | HmNHRsiRNALib-A1-1 | D5 | D | 5 | NM_021969 | NR0B2 | nuclear receptor subfamily 0, group B, member 2 | 8431 | s15996 | 0.25 nmole | Not Determined | Not Available | CCCUAUCAUUGGAGAUGUUtt | AACAUCUCCAAUGAUAGGGcg | 00CSIO7W6V |
| 4397914-AM003-02R-HmNHR | CPF00WBI | AS00E37W | HmNHRsiRNALib-A1-1 | D6 | D | 6 | NM_022002 | NR1I2 | nuclear receptor subfamily 1, group I, member 2 | 8856 | s16909 | 0.25 nmole | Not Determined | Not Available | GUCCUACAUUGAAUGCAAUtt | AUUGCAUUCAAUGUAGGACtt | 00CSIO7W6X |

| | | | | | | | | | | | |
|---|---|---|---|---|---|---|---|---|---|---|---|
| 4397914-AMO03 02R-Hm NHR | CPF0 0WB I | AS00E 37X | Hm NHR siRNA Lib-A1-1 | D7 | D | 7 | NM_0 21724 | NR1D 1 | nuclear receptor sub-family 1, group D, member 1 | 9572 | s18386 | 0.25 nmole | 2 | http://www.ambion.com/catalog/exon_sirna.php?id=18386 | CUGAAU CCCUCU AUAGUG Att | UCACUA UAGAGG GAUUCA Ggg | 00CSIO 7RYE |
| 4397914-AMO03 02R-Hm NHR | CPF0 0WB I | AS00E 37Y | Hm NHR siRNA Lib-A1-1 | D8 | D | 8 | NM_0 01077 469 | NR3|3 | nuclear receptor sub-family | 9970 | s19368 | 0.25 nmole | 3,2,3,2, 2,3,2,2, 2,3 | http://www.ambion.com/catalog/exon_sirna.php?id=19368 | GCUGGA AGCUGU GAAGUC Att | UGACUU CACAGC UUCCAG Caa | 00CSIO 7W70 |
| 4397914-AMO03 02R-Hm NHR | CPF0 0WB I | AS00E 37Z | Hm NHR siRNA Lib-A1-1 | D9 | D | 9 | NM_0 05123 | NR1H 4 | nuclear receptor sub-family 1, group t, member 3 | 9971 | s19371 | 0.25 nmole | 9 | http://www.ambion.com/catalog/exon_sirna.php?id=19371 | GGUCUG CGGUUG AAGCUA Utt | AUAGCU UCAACC CCAGAC Cct | 00CSIO 7Q8Q |
| 4397914-AMO03 02R-Hm NHR | CPF0 0WB I | AS00E 380 | Hm NHR siRNA Lib-A1-1 | D10 | D | 10 | XM_0 01130 839 | NR1D 2 | nuclear receptor sub-family 1, group H, member 4 | 9975 | s19380 | 0.25 nmole | Not De-termined | Not Avail-able | GGUUUG GUCGUA UUCCUA Att | UUAGGA AUACGA CCAAACC ga | 00CSIO 7PEY |
| 4397914-AMO03 02R-Hm NHR | CPF0 0WB I | AS00E 381 | Hm NHR siRNA Lib-A1-1 | D11 | D | 11 | NM_0 14249 | NR2E 3 | nuclear receptor sub-family 2, group E, member 3 | 10000 | s19433 | 0.25 nmole | 4,4 | http://www.ambion.com/catalog/exon_sirna.php?id=19433 | GCAUGG AGUCCA ACACUG Att | UCAGUG UUGGAC UCCAUG Ctg | 00CSIO 7W75 |

-continued

| | | | | | | | | | | | |
|---|---|---|---|---|---|---|---|---|---|---|---|
| 439791 4- AM003 02R-Hm NHR | CPF0 0WB I | Empty Well | Hm NHR siRNA Lib- A1-1 | D12 | D | 12 | | | | | | |
| 439791 4- AM003 02R-Hm NHR | CPF0 0WB I | AS00E 382 | Hm NHR siRNA Lib- A1-1 | E1 | E | 1 | NM_0 05693 | NR1H 3 | nuclear receptor sub- family 1, group H, member 3 | 1006 2 | s1956 8 | 0.25 nmole | Not De- termined | Not Avail- able | GGAUGC UAAUGA AACUGG Utt | ACCAGU UUCAUU AGCAUC Cgt | 00CSIO 7W77 |
| 439791 4- AM003 02R-Hm NHR | CPF0 0WB I | AS00E 383 | Hm NHR siRNA Lib- A1-1 | E2 | E | 2 | NM_0 52951 | DNTTI P1 | deoxy- nucleo- trans- ferase, terminal, interact- ing protein 1 | 1160 92 | s4192 2 | 0.25 nmole | 2 | http:// www. ambion. com/ catalog/ exon_ sirna. php?id= 41922 | GGAACA UAAUGA UAAAGC Att | UGCUUU AUCAUU AUGUUC Caa | 00CSIO 7W7A |
| 439791 4- AM003 02R-Hm NHR | CPF0 0WB I | AS00E 380 | Hm NHR siRNA Lib- A1-1 | E3 | E | 3 | NM_0 06917 | RXRG | retinoid X receptor, gamma | 6258 | s2004 54 | 0.25 nmole | 5 | http:// www. ambion. com/ catalog/ exon_ sirna. php?id= 200454 | AAAUGA CCCUGU UACCAA Ctt | GUUGGU AACAGG UACAUU Ugt | 00CSIO 7W7E |
| 439791 4- AM003 02R-Hm NHR | CPF0 0WB I | Empty Well | Hm NHR siRNA Lib- A1-1 | E4 | E | 4 | | | | | | | | | | | |
| 439791 4- AM003 02R-Hm NHR | CPF0 0WB I | Empty Well | Hm NHR siRNA Lib- A1-1 | E5 | E | 5 | | | | | | | | | | | |
| 439791 4- AM003 02R-Hm NHR | CPF0 0WB I | Empty Well | Hm NHR siRNA Lib- A1-1 | E6 | E | 6 | | | | | | | | | | | |

-continued

| | | | | | |
|---|---|---|---|---|---|
| 4397914-AM003 02R-Hm NHR | CPF0 0wB I | Empty Well | Hm NHR siRNA Lib-A1-1 | E7 | E 9 |
| 4397914-AM003 02R-Hm NHR | CPF0 0wB I | Empty Well | Hm NHR siRNA Lib-A1-1 | E8 | E 8 |
| 4397914-AM003 02R-Hm NHR | CPF0 0wB I | Empty Well | Hm NHR siRNA Lib-A1-1 | E9 | E 9 |
| 4397914-AM003 02R-Hm NHR | CPF0 0wB I | Empty Well | Hm NHR siRNA Lib-A1-1 | E10 | E 10 |
| 4397914-AM003 02R-Hm NHR | CPF0 0wB I | Empty Well | Hm NHR siRNA Lib-A1-1 | E11 | E 11 |
| 4397914-AM003 02R-Hm NHR | CPF0 0wB I | Empty Well | Hm NHR siRNA Lib-A1-1 | E12 | E 12 |
| 4397914-AM003 02R-Hm NHR | CPF0 0wB I | Empty Well | Hm NHR siRNA Lib-A1-1 | F1 | F 1 |
| 4397914-AM003 02R-Hm NHR | CPF0 0wB I | Empty Well | Hm NHR siRNA Lib-A1-1 | F2 | F 2 |
| 4397914-AM003 02R-Hm NHR | CPF0 0wB I | Empty Well | Hm NHR siRNA Lib-A1-1 | F3 | F 3 |

| | | | | | |
|---|---|---|---|---|---|
| 439791 4-AMO03 02R-Hm NHR | CPF0 0WB I | Empty Well | Hm NHR siRNA Lib-A1-1 | F4 | F 4 |
| 439791 4-AMO03 02R-Hm NHR | CPF0 0WB I | Empty Well | Hm NHR siRNA Lib-A1-1 | F5 | F 5 |
| 439791 4-AMO03 02R-Hm NHR | CPF0 0WB I | Empty Well | Hm NHR siRNA Lib-A1-1 | F6 | F 6 |
| 439791 4-AMO03 02R-Hm NHR | CPF0 0WB I | Empty Well | Hm NHR siRNA Lib-A1-1 | F7 | F 7 |
| 439791 4-AMO03 02R-Hm NHR | CPF0 0WB I | Empty Well | Hm NHR siRNA Lib-A1-1 | F8 | F 8 |
| 439791 4-AMO03 02R-Hm NHR | CPF0 0WB I | Empty Well | Hm NHR siRNA Lib-A1-1 | F9 | F 9 |
| 439791 4-AMO03 02R-Hm NHR | CPF0 0WB I | Empty Well | Hm NHR siRNA Lib-A1-1 | F10 | F 10 |
| 439791 4-AMO03 02R-Hm NHR | CPF0 0WB I | Empty Well | Hm NHR siRNA Lib-A1-1 | F11 | F 11 |
| 439791 4-AMO03 02R-Hm NHR | CPF0 0WB I | Empty Well | Hm NHR siRNA Lib-A1-1 | F12 | F 12 |

-continued

| | | | | | |
|---|---|---|---|---|---|
| 439791-4-AM003 02R-Hm NHR | CPF0 0WB I | Empty Well | Hm NHR siRNA Lib-A1-1 | G1 | G 1 |
| 439791-4-AM003 02R-Hm NHR | CPF0 0WB I | Empty Well | Hm NHR siRNA Lib-A1-1 | G2 | G 2 |
| 439791-4-AM003 02R-Hm NHR | CPF0 0WB I | Empty Well | Hm NHR siRNA Lib-A1-1 | G3 | G 3 |
| 439791-4-AM003 02R-Hm NHR | CPF0 0WB I | Empty Well | Hm NHR siRNA Lib-A1-1 | G4 | G 4 |
| 439791-4-AM003 02R-Hm NHR | CPF0 0WB I | Empty Well | Hm NHR siRNA Lib-A1-1 | G5 | G 5 |
| 439791-4-AM003 02R-Hm NHR | CPF0 0WB I | Empty Well | Hm NHR siRNA Lib-A1-1 | G6 | G 6 |
| 439791-4-AM003 02R-Hm NHR | CPF0 0WB I | Empty Well | Hm NHR siRNA Lib-A1-1 | G7 | G 7 |
| 439791-4-AM003 02R-Hm NHR | CPF0 0WB I | Empty Well | Hm NHR siRNA Lib-A1-1 | G8 | G 8 |
| 439791-4-AM003 02R-Hm NHR | CPF0 0WB I | Empty Well | Hm NHR siRNA Lib-A1-1 | G9 | G 9 |

-continued

| | | | | | |
|---|---|---|---|---|---|
| 4397914-AM003 02R-Hm NHR | CPF0 0WB I | Empty Well | Hm NHR siRNA Lib-A1-1 | G10 | G | 10 |
| 4397914-AM003 02R-Hm NHR | CPF0 0WB I | Empty Well | Hm NHR siRNA Lib-A1-1 | G11 | G | 11 |
| 4397914-AM003 02R-Hm NHR | CPF0 0WB I | Empty Well | Hm NHR siRNA Lib-A1-1 | G12 | G | 12 |
| 4397914-AM003 02R-Hm NHR | CPF0 0WB I | Empty Well | Hm NHR siRNA Lib-A1-1 | H1 | G | 1 |
| 4397914-AM003 02R-Hm NHR | CPF0 0WB I | Empty Well | Hm NHR siRNA Lib-A1-1 | H1 | H | 1 |
| 4397914-AM003 02R-Hm NHR | CPF0 0WB I | Empty Well | Hm NHR siRNA Lib-A1-1 | H2 | H | 2 |
| 4397914-AM003 02R-Hm NHR | CPF0 0WB I | Empty Well | Hm NHR siRNA Lib-A1-1 | H3 | H | 3 |
| 4397914-AM003 02R-Hm NHR | CPF0 0WB I | Empty Well | Hm NHR siRNA Lib-A1-1 | H4 | H | 4 |
| 4397914-AM003 02R-Hm NHR | CPF0 0WB I | Empty Well | Hm NHR siRNA Lib-A1-1 | H5 | H | 5 |

-continued

| | | | | | | | | | | | | |
|---|---|---|---|---|---|---|---|---|---|---|---|---|
| 4397914-AMO034-Hm02R-HmNHR | CPF00WBI | Empty Well | Hm NHR siRNA Lib-A1-1 | H6 | H | 6 | | | | | | |
| 4397914-AMO034-Hm02R-HmNHR | CPF00WBI | Empty Well | Hm NHR siRNA Lib-A1-1 | H7 | H | 7 | | | | | | |
| 4397914-AMO034-Hm02R-HmNHR | CPF00WBI | Empty Well | Hm NHR siRNA Lib-A1-1 | H8 | H | 8 | | | | | | |
| 4397914-AMO034-Hm02R-HmNHR | CPF00WBI | Empty Well | Hm NHR siRNA Lib-A1-1 | H9 | H | 9 | | | | | | |
| 4397914-AMO034-Hm02R-HmNHR | CPF00WBI | Empty Well | Hm NHR siRNA Lib-A1-1 | H10 | H | 10 | | | | | | |
| 4397914-AMO034-Hm02R-HmNHR | CPF00WBI | Empty Well | Hm NHR siRNA Lib-A1-1 | H11 | H | 11 | | | | | | |
| 4397914-AMO034-Hm02R-HmNHR | CPF00WBI | Empty Well | Hm NHR siRNA Lib-A1-1 | H12 | H | 12 | | | | | | |
| 4397914-AMO034-Hm02R-HmNHR | CPF00WBJ | AS00E38P | Hm NHR siRNA Lib-B1-1 | A | A | 1 | NM_000475 | NR0B1 | nuclear receptor subfamily 0, group B, member 1 | 190 | s1193 | 0.25 nmole | Not Determined | Not Available | ACAGAUUCAUCGAACUUAAtt | UUAAGUUCGAUGAAUCUGUca | 00CSI07NHN |

| | | | | | | | | | | | | | |
|---|---|---|---|---|---|---|---|---|---|---|---|---|---|
| 439791 4- AM003 02R-Hm NHR | CPF0 0WB J | AS00E 38Q | Hm NHR siRNA Lib- B1-1 | A2 | A | 2 | NM_0 00044 | AR | androgen receptor | 367 | s1539 | 0.25 nmole | 7,7 | http:// www. ambion. com/ catalog/ exon_ sirna. php?id= 1539 | GGAACU CGAUCG UAUCAU Utt | AAUGAU ACGAUC GAGUUC Ctt | 00CSI0 7OMA |
| 439791 4- AM003 02R-Hm NHR | CPF0 0WB J | AS00E 38R | Hm NHR siRNA Lib- B1-1 | A3 | A | 3 | NM_0 05234 | NR2F 6 | nuclear receptor sub- family 2, group F, member 6 | 2063 | s4777 | 0.25 nmole | 4 | http:// www. ambion. com/ catalog/ exon_ sirna. php?id= 4777 | CCUCUG GACACG UAACCU Att | UAGGUU ACGUGU CCAGAG Gat | 00CSI0 7SJ7 |
| 439791 4- AM003 02R-Hm NHR | CPF0 0WB J | AS00E 38S | Hm NHR siRNA Lib- B1-1 | A4 | A | 4 | NM_0 00125 | ESR1 | estrogen receptor 1 | 2099 | s4824 | 0.25 nmole | Not De- termined | Not Avail- able | CAGGCA CAUGAG UAACAA Att | UUUGUU ACUCAU GUGCCU Gat | 00CSI0 7O5T |
| 439791 4- AM003 02R-Hm NHR | CPF0 0WB J | AS00E 38T | Hm NHR siRNA Lib- B1-1 | A5 | A | 5 | NM_0 01040 275 | ESR2 | estrogen receptor 2 (ER beta) | 2100 | s4827 | 0.25 nmole | 2,2,2 | http:// www. ambion. com/ catalog/ exon_ sirna. php?id= 4827 | CCUUAC CUGUAA ACAGAG Att | UCUCUG UUUACA GGUAAG Gtg | 00CSI0 7NUP |
| 439791 4- AM003 02R-Hm NHR | CPF0 0WB J | AS00E 38U | Hm NHR siRNA Lib- B1-1 | A6 | A | 6 | NM_0 04451 | ESRR A | estrogen related receptor alpha | 2101 | s4830 | 0.25 nmole | 6 | http:// www. ambion. com/ catalog/ exon_ sirna. php?id= 4830 | AGGAGU AUGUUC UACUAA Att | UUUAGU AGAACA UACUCC Uct | 00CSI0 7O5X |
| 439791 4- AM003 02R-Hm NHR | CPF0 0WB J | AS00E 38V | Hm NHR siRNA Lib- B1-1 | A7 | A | 7 | NM_0 4452 | ESRR B | estrogen related receptor alpha | 2103 | s4833 | 0.25 nmole | Not De- termined | Not Avail- able | CCAUAC CUGAGC UUACAA Att | UUUGUA AGCUCA GGUAUG Ggc | 00CSI0 7O5Z |

| | | | | | | | | | | | | |
|---|---|---|---|---|---|---|---|---|---|---|---|---|
| 4397914-AM003 02R-Hm NHR | CPF00WBJ | AS00E 38W | Hm NHR siRNA Lib-B1-1 | A8 | A | 8 | NM_0 01438 | ESRR G | estrogen related receptor gamma | 2104 | s4836 | 0.25 nmole | 6, 8, 7 | http:// www. ambion. com/ catalog/ exon_ sirna. php?id= 4836 | CCCUCA AAGCUA UAGCUC Utt | AGAGCU AUAGCU UUGAGG Gtg | 00CSIO 70H8 |
| 4397914-AM003 02R-Hm NHR | CPF00WBJ | AS00E 38X | Hm NHR siRNA Lib-B1-1 | A9 | A | 9 | NM_0 03822 | NR5A 2 | nuclear receptor sub- family 5, group A, member 2 | 2494 | s5381 | 0.25 nmole | 5, 6 | http:// www. ambion. com/ catalog/ exon_ sirna. php?id= 5381 | CGACCA CAUUUA CCGACA Att | UUGUCG GUAAAU GUGGUC Gag | 00CSIO 7S6X |
| 4397914-AM003 02R-Hm NHR | CPF00WBJ | AS00E 38Y | Hm NHR siRNA Lib-B1-1 | A10 | A | 10 | NM_0 04959 | NR5A 1 | nuclear receptor sub- family 5, group A, member 1 | 2516 | s5393 | 0.25 nmole | Not De- termined | Not Avail- able | UGAAGU UCCUGA AUAACC Att | UGGUUA UUCAGG AACUUC Aaa | 00CSIO 7I68 |
| 4397914-AM003 02R-Hm NHR | CPF00WBJ | AS00E 38Z | Hm NHR siRNA Lib-B1-1 | A11 | A | 11 | NM_0 01489 | NR6A 1 | nuclear receptor sub- family 6, group A, member 1 | 2649 | s5661 | 0.25 nmole | 3, 3 | http:// www. ambion. com/ catalog/ exon_ sirna. php?id= 5661 | GCGGAG CAUUUG CAACAA Att | UUUGUU GCAAAU GCUCCG Ctt | 00CSIO 7SAQ |
| 4397914-AM003 02R-Hm NHR | CPF00WBJ | Empty Well | Hm NHR siRNA Lib-B1-1 | A12 | A | 12 | | | | | | | | | | | |

-continued

| | | | | | | | | | | | | |
|---|---|---|---|---|---|---|---|---|---|---|---|---|
| 4397914-AM003 02R-Hm NHR | CPF0 0WB J | AS00E 390 | Hm NHR siRNA Lib-B1-1 | B1 | B | 1 | NM_000176 | NR3C1 | nuclear receptor sub-family 3, group C, member 1 (gluco-corticoid receptor) | 2908 | s6186 | 0.25 nmole | 2,2,2,2, 2,2,2 | http://www.ambion.com/catalog/exon_sirna.php?id=6186 | GCAGGA UCAGAA GCCUAU Utt | AAUAGG CUUCUG AUCCUG Ctg | 00CSIO 7SLT |
| 4397914-AM003 02R-Hm NHR | CPF0 0WB J | AS00E 391 | Hm NHR siRNA Lib-B1-1 | B2 | B | 2 | NM_002135 | NR4A1 | nuclear receptor sub-family 4, group A, member 1 | 3164 | s6679 | 0.25 nmole | 3,2 | http://www.ambion.com/catalog/exon_sirna.php?id=6679 | CCACUU CUCCAC ACCUUG Att | UCAAGG UGUGGA GAAGUG Ggt | 00CSIO 7REK |
| 4397914-AM003 02R-Hm NHR | CPF0 0WB J | AS00E 392 | Hm NHR siRNA Lib-B1-1 | B3 | B | 3 | NM_000901 | NR3C2 | nuclear receptor sub-family 3, group C, member 2 | 4306 | s8839 | 0.25 nmole | Not De-termined | Not Avail-able | CAGCUA AGAUUU AUCAGA Att | UUCUGA UAAAUC UUAGCU Gga | 00CSIO 7V84 |
| 4397914-AM003 02R-Hm NHR | CPF0 0WB J | AS00E 393 | Hm NHR siRNA Lib-B1-1 | B4 | B | 4 | NM_173172 | NR4A2 | nuclear receptor sub-family 4, group A, member 2 | 4929 | s9786 | 0.25 nmole | Not De-termined | Not Avail-able | GCAGUC CUCCAU UAAGGU Att | UACCUU AAUGGA GGACUG Ctg | 00CSIO 7UJK |
| 4397914-AM003 02R-Hm NHR | CPF0 0WB J | AS00E 394 | Hm NHR siRNA Lib-B1-1 | B5 | B | 5 | NM_000926 | PGR | progest-erone receptor | 5241 | si10416 | 0.25 nmole | Not De-termined | Not Avail-able | GGUUUU CGAAAC UUACAU Att | UAUGUA AGUUUC GAAAAC Ctg | 00CSIO 7W5B |

| | | | | | | | | | | | | |
|---|---|---|---|---|---|---|---|---|---|---|---|---|
| 4397914-AM00302R-HmNHR | CPF00WBJ | AS00E395 | Hm NHR siRNA Lib-B1-1 | B6 | B | 6 | NM_001001928 | PPARA | peroxisome proliferator-activated receptor alpha | 5465 | s10881 | 0.25 nmole | 7, 8 | http://www.ambion.com/catalog/exon_sirna.php?id=10881 | GUAUGG AAAUGG GUUUAU Att | UAUAAA CCCAUU UCCAUA Cgc | 00CSIO7VJU |
| 4397914-AM00302R-HmNHR | CPF00WBJ | AS00E396 | Hm NHR siRNA Lib-B1-1 | B7 | B | 7 | NM_006238 | PPARD | peroxisome proliferator-activated receptor delta | 5467 | s10884 | 0.25 nmole | Not Determined | Not Available | ACUUCA ACAUGA CCAAAA Att | UUUUUG GUCAUG UUGAAG Utt | 00CSIO7VJX |
| 4397914-AM00302R-HmNHR | CPF00WBJ | AS00E397 | Hm NHR siRNA Lib-B1-1 | B8 | B | 8 | NM_005037 | PPARG | peroxisome proliferator-activated receptor gamma | 5468 | s10887 | 0.25 nmole | 5, 5, 6, 6 | http://www.ambion.com/catalog/exon_sirna.php?id=10887 | GGGCGA UCUUGA CAGGAA Att | UUUCCU GUCAAG AUCGCC Ctc | 00CSIO7VK0 |
| 4397914-AM00302R-HmNHR | CPF00WBJ | AS00E398 | Hm NHR siRNA Lib-B1-1 | B9 | B | 9 | NM_000964 | RARA | retinoic acid receptor, alpha | 5914 | s11801 | 0.25 nmole | 8, 7 | http://www.ambion.com/catalog/exon_sirna.php?id=11801 | GAAGAU UACUGA CCUGCG Att | UCGCAG GUCAGU AAUCUU Cat | 00CSIO7VXT |
| 4397914-AM00302R-HmNHR | CPF00WBJ | AS00E399 | Hm NHR siRNA Lib-B1-1 | B10 | B | 10 | NM_016152 | RARB | retinoic acid receptor, beta | 5915 | s11804 | 0.25 nmole | Not Determined | Not Available | GAAUCU GUCAGG AAUGAC Att | UGUCAU UCCUGA CAGAUU Ctt | 00CSIO7W5P |

| | | | | | | | | | | | | |
|---|---|---|---|---|---|---|---|---|---|---|---|---|
| 4397914-AM00302R-HmNHR | CPF00WBJ | AS00E39A | Hm NHR siRNA Lib-B1-1 | B11 | B | 11 | NM_000966 | RARG | retinoic acid receptor, gamma | 5916 | s11807 | 0.25 nmole | 5, 3 | http://www.ambion.com/catalog/exon_sirna.php?id=11807 | AGGAAGCUGUGCGAAAUGAtt | UCAUUUCGCACAGCUUCCUtg | 00CSI07VXY |
| 4397914-AM00302R-HmNHR | CPF00WBJ | Empty Well | Hm NHR siRNA Lib-B1-1 | B12 | B | 12 | | | | | | | | | | |
| 4397914-AM00302R-HmNHR | CPF00WBJ | AS00E39B | Hm NHR siRNA Lib-B1-1 | C1 | C | 1 | NM_134260 | RORA | RAR-related orphan receptor A | 6095 | s12104 | 0.25 nmole | Not De-termined | Not Avail-able | GGAGACAAAUCAUCAGGAtt | UUCCUGAUGAUGUCUCCac | 00CSI07W5V |
| 4397914-AM00302R-HmNHR | CPF00WBJ | AS00E39C | Hm NHR siRNA Lib-B1-1 | C2 | C | 2 | NM_006914 | RORB | RAR-related orphan receptor B | 6096 | s12107 | 0.25 nmole | 4 | http://www.ambion.com/catalog/exon_sirna.php?id=12107 | GGACUUGACUAGACUGGAtt | UUCCAGUCAUGUCAAGUCtg | 00CSI07WSY |
| 4397914-AM00302R-HmNHR | CPF00WBJ | AS00E39D | Hm NHR siRNA Lib-B1-1 | C3 | C | 3 | NM_001001523 | RORC | RAR-related orphan receptor C | 6097 | s12110 | 0.25 nmole | 10, 11 | http://www.ambion.com/catalog/exon_sirna.php?id=12110 | CAAUCUCUCUUAUCCUUGAtt | UCAAGGAUAAGAGAGAUUGtg | 00CSI07VM7 |
| 4397914-AM00302R-HmNHR | CPF00WBJ | AS00E39E | Hm NHR siRNA Lib-B1-1 | C4 | C | 4 | NM_002957 | RXRA | retinoid X receptor, alpha | 6256 | s12385 | 0.25 nmole | Not De-termined | Not Avail-able | GCAAGGACCGGAACGAGAtt | UUCUCGUUCCGGUCCUUGCca | 00CSI07W64 |

| | | | | | | | | | | | | |
|---|---|---|---|---|---|---|---|---|---|---|---|---|
| 439791 4- AM003 02R-Hm NHR | CPF0 0WB J | AS00E 39F | Hm NHR siRNA Lib- B1-1 | C5 | 5 | C | NM_0 21976 | RXRB | retinoid X receptor, beta | 6257 | s1238 8 | 0.25 nmole | 7 | http:// www. ambion. com/ catalog/ exon_ sirna. php?id= 12388 | GAUCCA UUGAUG UUCGAG Att | UCUCGA ACAUCA AUGGAU Cgg | 00CSIO 7PHK |
| 439791 4- AM003 02R-Hm NHR | CPF0 0WB J | AS00E 39G | Hm NHR siRNA Lib- B1-1 | C6 | 6 | C | NM_0 05654 | NR2F 1 | nuclear receptor sub- family 2, group F, member 1 | 7025 | s1401 9 | 0.25 nmole | 2 | http:// www. ambion. com/ catalog/ exon_ sirna. php?id= 14019 | ACAACA UUAUGG GCAUCG Att | UCGAUG CCCAUA AUGUUG Utg | 00CSIO 7W66 |
| 439791 4- AM003 02R-Hm NHR | CPF0 0WB J | AS00E 39H | Hm NHR siRNA Lib- B1-1 | C7 | 7 | C | NM_0 21005 | NR2F 2 | nuclear receptor sub- family 2, group F, member 2 | 7026 | s1402 2 | 0.25 nmole | Not De- termined | Not Avail- able | CGCCUU UAUGGA CCACAU Att | UAUGUG GUCCAU AAAGGC Gac | 00CSIO 7W69 |
| 439791 4- AM003 02R-Hm NHR | CPF0 0WB J | AS00E 39I | Hm NHR siRNA Lib- B1-1 | C8 | 8 | C | NM_0 03250 | THRA | thyroid hormone receptor, alpha (erythrob lastic leukemia viral (v- erb-a) oncogene homolog, avian) | 7067 | s1411 7 | 0.25 nmole | 6, 6 | http:// www. ambion. com/ catalog/ exon_ sirna. php?id= 14117 | AGCGUA AGCUGA UUGAGC Att | UGCUCA AUCAGC UUACGC Utg | 00CSIO 7W6C |

-continued

| | | | | | | | | | | | | |
|---|---|---|---|---|---|---|---|---|---|---|---|---|
| 4397914-AM003 02R-Hm NHR | CPF00WBJ | AS00E 39J | Hm NHR siRNA Lib-B1-1 | C9 | C | 9 | NM_000461 | THRB | thyroid hormone receptor, beta (erythroblastic leukemia viral (v-erb-a) oncogene homolog 2, avian) | 7068 | s14120 | 0.25 nmole | Not De-termined | Not Available | CACUUG GACUAG GUCAAU Att | UAUUGA GCUAGU CCAAGU Ggt | 00CSIO 7W6F |
| 4397914-AM003 02R-Hm NHR | CPF00WBJ | AS00E 32K | Hm NHR siRNA Lib-B1-1 | C10 | C | 10 | NM_003269 | NR2F1 | nuclear receptor sub-family 2, group E, member 1 | 7101 | s14201 | 0.25 nmole | Not De-termined | Not Available | GCUACA UCCAUA CCAGAU Att | UAUCUG GUAUGG AUGUAG Ctg | 00CSIO 7W6I |
| 4397914-AM003 02R-Hm NHR | CPF00WBJ | AS00E 32L | Hm NHR siRNA Lib-B1-1 | C11 | C | 11 | NM_01032 287 | NR2C1 | nuclear receptor sub-family 2, group C, member 1 | 7181 | s14368 | 0.25 nmole | Not De-termined | Not Available | GGUUUU UGAUCU UUGCGU Att | UACGCA AAGAUC AAAAAC Ctt | 00CSIO 7W6L |
| 4397914-AM003 02R-Hm NHR | CPF00WBJ | Empty Well | Hm NHR siRNA Lib-B1-1 | C12 | C | 12 | | | | | | | | | | |
| 4397914-AM003 02R-Hm NHR | CPF00WBJ | AS00E 32M | Hm NHR siRNA Lib-B1-1 | D1 | D | 1 | NM_003298 | NR2C2 | nuclear receptor sub-family 2, group C, member 2 | 7182 | s14371 | 0.25 nmole | 7 | http://www.ambion.com/catalog/exon_sirna.php?id=14371 | GAGAAA AUCUAU AUCCGG Att | UCCGGA UAUAGA UUUUCU Cag | 00CSIO 715C |

-continued

| | | | | | | | | | | | | |
|---|---|---|---|---|---|---|---|---|---|---|---|---|
| 4397914-AM003 02R-HmNHR | CPF00WBJ | AS00E32N | HmNHRsiRNALib-B1-1 | D2 | 2 | NM_071721 | NR1H2 | nuclear receptor subfamily 1, group H, member 2 | 7376 | s14685 | 0.25 nmole | 6 | http://www.ambion.com/catalog/exon_sirna.php?id=14685 | AGCUAACAGCGGCUCAAGAtt | UCUUGAGCCGCGGUUAGCUgg | 00CSIO7W6O |
| 4397914-AM003 02R-HmNHR | CPF00WBJ | AS00E32O | HmNHRsiRNALib-B1-1 | D3 | 3 | NM_000376 | VDR | vitamin D (1,25-dihydroxyvitamin D3) receptor | 7421 | s14778 | 0.25 nmole | 3,4 | http://www.ambion.com/catalog/exon_sirna.php?id=14778 | GGCGAAGCAUGAAGCGGAAtt | UUCCGCUUCAUGCUUCGCCtg | 00CSIO7W6Q |
| 4397914-AM003 02R-HmNHR | CPF00WBJ | AS00E32P | HmNHRsiRNALib-B1-1 | D4 | 4 | NM_006981 | NR4A3 | nuclear receptor subfamily 4, group A, member 3 | 8013 | s15542 | 0.25 nmole | 3,3,2 | http://www.ambion.com/catalog/exon_sirna.php?id=15542 | CCUUCCUGCCUGUACCAAtt | UUUGGUACACGCAGGAAGGct | 00CSIO7W6T |
| 4397914-AM003 02R-HmNHR | CPF00WBJ | AS00E32Q | HmNHRsiRNALib-B1-1 | D5 | 5 | NM_021969 | NR0B2 | nuclear receptor subfamily 0, group B, member 2 | 8431 | s15997 | 0.25 nmole | Not Determined | Not Available | GGAAUAUGCCUGCCUGAAtt | UUUCAGGCAGGCAUAUUCctt | 00CSIO7Q97 |
| 4397914-AM003 02R-HmNHR | CPF00WBJ | AS00E32R | HmNHRsiRNALib-B1-1 | D6 | 6 | NM_022002 | NR1I2 | nuclear receptor subfamily 1, group I, member 2 | 8856 | s16910 | 0.25 nmole | Not Determined | Not Available | GACACUACCUUCUCCCAUUtt | AAUGGGAGAAGGUAGUGUCaa | 00CSIO7W6y |

-continued

| | | | | | | | | | | | | | |
|---|---|---|---|---|---|---|---|---|---|---|---|---|---|
| 4397914-AM003 02R-HmNHR | CPF00WBJ | AS00E32S | Hm NHR siRNA Lib-B1-1 | D7 | D | 7 | NM_021724 | NR1D1 | nuclear receptor subfamily 1, group D, member 1 | 9572 | s18387 | 0.25 nmole | 5 | http://www.ambion.com/catalog/exon_sirna.php?id=18387 | GCAGGGCAACUCAAAGAAUtt | AUUCUUUGAGUUGCCCUGCcg | 00CSIO7RYD |
| 4397914-AM003 02R-HmNHR | CPF00WBJ | AS00E32T | Hm NHR siRNA Lib-B1-1 | D8 | D | 8 | NM_001077469 | NR1I3 | nuclear receptor subfamily 1, group I, member 3 | 9970 | s19369 | 0.25 nmole | 6,5,6,5,5,6,5,5,5,6 | http://www.ambion.com/catalog/exon_sirna.php?id=19369 | GGAAAUCUGUCACAUCGUAtt | UACGAUGUGACAGAUUUCCac | 00CSIO7W71 |
| 4397914-AM003 02R-HmNHR | CPF00WBJ | AS00E32U | Hm NHR siRNA Lib-B1-1 | D9 | D | 9 | NM_005123 | NR1H4 | nuclear receptor subfamily 1, group H, member 4 | 991 | s19372 | 0.25 nmole | 4 | http://www.ambion.com/catalog/exon_sirna.php?id=19372 | CCAUACUCGCAAUACAGCAtt | UGCUGUAUUGCGAGUAUGGtt | 00CSIO7W73 |
| 4397914-AM003 02R-HmNHR | CPF00WBJ | AS00E32V | Hm NHR siRNA Lib-B1-1 | D10 | D | 10 | XM_001130839 | NR1D2 | nuclear receptor subfamily 1, group D, member 2 | 9975 | s19381 | 0.25 nmole | Not Determined | Not Available | CGAAUAGAUUGUUCUAUGAtt | UCAUAGAACAAUCUAUUCGat | 00CSIO7PVN |
| 4397914-AM003 02R-HmNHR | CPF00WBJ | AS00E32W | Hm NHR siRNA Lib-B1-1 | D11 | D | 11 | NM_014249 | NR2E3 | nuclear receptor subfamily 2, group E, member 3 | 10002 | s19434 | 0.25 nmole | 7,7 | http://www.ambion.com/catalog/exon_sirna.php?id=19434 | GAAGGAUCCUGAGCACGUAtt | UACGUGCUCAGGAUCCUUCag | 00CSIO7W76 |

-continued

| | | | | | | | | | | | |
|---|---|---|---|---|---|---|---|---|---|---|---|
| 4397914-AM003 02R-HmNHR | CPF00WB0J | Empty Well | Hm NHR siRNA Lib-B1-1 | D12 | D | 12 | | | | | |
| 4397914-AM003 02R-HmNHR | CPF00WB0J | AS00E32X | Hm NHR siRNA Lib-B1-1 | E1 | E | 1 | NM_005693 | NR1H3 | nuclear receptor subfamily 1, group H, member 3 | 10062 | s19569 | 0.25 nmole | Not De-termined | Not Available | CGACUG AUGUUC CCACGG Att | UCCGUG GGAACA UCAGUC Ggt | 00CSI0 7W788 |
| 4397914-AM003 02R-HmNHR | CPF00WB0J | AS00E32Y | Hm NHR siRNA Lib-B1-1 | E2 | E | 2 | NM_052951 | DNTTIP1 | deoxy-nucleo-tidyl trans-ferase, terminal, Interacting protein 1 | 116092 | s41923 | 0.25 nmole | 10 | http://www.ambion.com/catalog/exon_sirna.php?id=41923 | CCCACAC CUCUUU AAGUAU tt | AUACUU AAAGAG GUGUGG Gtg | 00CSI0 7W78 |
| 4397914-AM003 02R-HmNHR | CPF00WB0J | AS00E32Z | Hm NHR siRNA Lib-B1-1 | E3 | E | 3 | NM_006917 | RXRG | retinoid X receptor, gamma | 6258 | s200455 | 0.25 nmole | 3 | http://www.ambion.com/catalog/exon_sirna.php?id=200455 | GGAUCU CUGGUU AAACAC Att | UGUGUU UAACCA GAGAUC Cgg | 00CSI0 7X8U |
| 4397914-AM003 02R-HmNHR | CPF00WB0J | Empty Well | Hm NHR siRNA Lib-B1-1 | E4 | E | 4 | | | | | | | | | | |
| 4397914-AM003 02R-HmNHR | CPF00WB0J | Empty Well | Hm NHR siRNA Lib-B1-1 | E5 | E | 5 | | | | | | | | | | |
| 4397914-AM003 02R-HmNHR | CPF00WB0J | Empty Well | Hm NHR siRNA Lib-B1-1 | E6 | E | 6 | | | | | | | | | | |

-continued

| | | | | | |
|---|---|---|---|---|---|
| 4397914-AMO03 02R-Hm NHR | CPF0 0WB J | Empty Well | Hm NHR siRNA Lib-B1-1 | E7 | E 7 |
| 4397914-AMO03 02R-Hm NHR | CPF0 0WB J | Empty Well | Hm NHR siRNA Lib-B1-1 | E8 | E 8 |
| 4397914-AMO03 02R-Hm NHR | CPF0 0WB J | Empty Well | Hm NHR siRNA Lib-B1-1 | E9 | E 9 |
| 4397914-AMO03 02R-Hm NHR | CPF0 0WB J | Empty Well | Hm NHR siRNA Lib-B1-1 | E10 | E 10 |
| 4397914-AMO03 02R-Hm NHR | CPF0 0WB J | Empty Well | Hm NHR siRNA Lib-B1-1 | E11 | E 11 |
| 4397914-AMO03 02R-Hm NHR | CPF0 0WB J | Empty Well | Hm NHR siRNA Lib-B1-1 | E12 | E 12 |
| 4397914-AMO03 02R-Hm NHR | CPF0 0WB J | Empty Well | Hm NHR siRNA Lib-B1-1 | F1 | F 1 |
| 4397914-AMO03 02R-Hm NHR | CPF0 0WB J | Empty Well | Hm NHR siRNA Lib-B1-1 | F2 | F 2 |
| 4397914-AMO03 02R-Hm NHR | CPF0 0WB J | Empty Well | Hm NHR siRNA Lib-B1-1 | F3 | F 3 |

-continued

| | | | | | |
|---|---|---|---|---|---|
| 439791-4-AM003 02R-Hm NHR | CPF0 0WB J | Empty Well | Hm NHR siRNA Lib-B1-1 | F4 | F | 4 |
| 439791-4-AM003 02R-Hm NHR | CPF0 0WB J | Empty Well | Hm NHR siRNA Lib-B1-1 | F5 | F | 5 |
| 439791-4-AM003 02R-Hm NHR | CPF0 0WB J | Empty Well | Hm NHR siRNA Lib-B1-1 | F6 | F | 6 |
| 439791-4-AM003 02R-Hm NHR | CPF0 0WB J | Empty Well | Hm NHR siRNA Lib-B1-1 | F7 | F | 7 |
| 439791-4-AM003 02R-Hm NHR | CPF0 0WB J | Empty Well | Hm NHR siRNA Lib-B1-1 | F8 | F | 8 |
| 439791-4-AM003 02R-Hm NHR | CPF0 0WB J | Empty Well | Hm NHR siRNA Lib-B1-1 | F9 | F | 9 |
| 439791-4-AM003 02R-Hm NHR | CPF0 0WB J | Empty Well | Hm NHR siRNA Lib-B1-1 | F10 | F | 10 |
| 439791-4-AM003 02R-Hm NHR | CPF0 0WB J | Empty Well | Hm NHR siRNA Lib-B1-1 | F11 | F | 11 |
| 439791-4-AM003 02R-Hm NHR | CPF0 0WB J | Empty Well | Hm NHR siRNA Lib-B1-1 | F12 | F | 12 |

-continued

| | | | | |
|---|---|---|---|---|
| 4397914-AM003-02R-HmNHR | CPF0OWBJ | Empty Well | Hm NHR siRNA Lib-B1-1 | G1 | G | 1 |
| 4397914-AM003-02R-HmNHR | CPF0OWBJ | Empty Well | Hm NHR siRNA Lib-B1-1 | G2 | G | 2 |
| 4397914-AM003-02R-HmNHR | CPF0OWBJ | Empty Well | Hm NHR siRNA Lib-B1-1 | G3 | G | 3 |
| 4397914-AM003-02R-HmNHR | CPF0OWBJ | Empty Well | Hm NHR siRNA Lib-B1-1 | G4 | G | 4 |
| 4397914-AM003-02R-HmNHR | CPF0OWBJ | Empty Well | Hm NHR siRNA Lib-B1-1 | G5 | G | 5 |
| 4397914-AM003-02R-HmNHR | CPF0OWBJ | Empty Well | Hm NHR siRNA Lib-B1-1 | G6 | G | 6 |
| 4397914-AM003-02R-HmNHR | CPF0OWBJ | Empty Well | Hm NHR siRNA Lib-B1-1 | G7 | G | 7 |
| 4397914-AM003-02R-HmNHR | CPF0OWBJ | Empty Well | Hm NHR siRNA Lib-B1-1 | G8 | G | 8 |
| 4397914-AM003-02R-HmNHR | CPF0OWBJ | Empty Well | Hm NHR siRNA Lib-B1-1 | G9 | G | 9 |

-continued

| | | | | | |
|---|---|---|---|---|---|
| 439791 4- AM003 02R-Hm NHR | CPF0 0WB J | Empty Well | Hm NHR siRNA Lib- B1-1 | G10 | G | 10 |
| 439791 4- AM003 02R-Hm NHR | CPF0 0WB J | Empty Well | Hm NHR siRNA Lib- B1-1 | G11 | G | 11 |
| 439791 4- AM003 02R-Hm NHR | CPF0 0WB J | Empty Well | Hm NHR siRNA Lib- B1-1 | G12 | G | 12 |
| 439791 4- AM003 02R-Hm NHR | CPF0 0WB J | Empty Well | Hm NHR siRNA Lib- B1-1 | H1 | H | 1 |
| 439791 4- AM003 02R-Hm NHR | CPF0 0WB J | Empty Well | Hm NHR siRNA Lib- B1-1 | H2 | H | 2 |
| 439791 4- AM003 02R-Hm NHR | CPF0 0WB J | Empty Well | Hm NHR siRNA Lib- B1-1 | H3 | H | 3 |
| 439791 4- AM003 02R-Hm NHR | CPF0 0WB J | Empty Well | Hm NHR siRNA Lib- B1-1 | H4 | H | 4 |
| 439791 4- AM003 02R-Hm NHR | CPF0 0WB J | Empty Well | Hm NHR siRNA Lib- B1-1 | H5 | H | 5 |
| 439791 4- AM003 02R-Hm NHR | CPF0 0WB J | Empty Well | Hm NHR siRNA Lib- B1-1 | H6 | H | 6 |

-continued

| | | | | | | | | | | | | |
|---|---|---|---|---|---|---|---|---|---|---|---|---|
| 4397914-AM003 02R-Hm NHR | CPF00WB J | Empty Well | Hm NHR siRNA Lib-B1-1 | H7 | H | 7 | | | | | | |
| 4397914-AM003 02R-Hm NHR | CPF00WB J | Empty Well | Hm NHR siRNA Lib-B1-1 | H8 | H | 8 | | | | | | |
| 4397914-AM003 02R-Hm NHR | CPF00WB J | Empty Well | Hm NHR siRNA Lib-B1-1 | H9 | H | 9 | | | | | | |
| 4397914-AM003 02R-Hm NHR | CPF00WB J | Empty Well | Hm NHR siRNA Lib-B1-1 | H10 | H | 10 | | | | | | |
| 4397914-AM003 02R-Hm NHR | CPF00WB J | Empty Well | Hm NHR siRNA Lib-B1-1 | H11 | H | 11 | | | | | | |
| 4397914-AM003 02R-Hm NHR | CPF00WB J | Empty Well | Hm NHR siRNA Lib-B1-1 | H12 | H | 12 | | | | | | |
| 4397914-AM003 02R-Hm NHR | CPF00WB K | AS00E 330 | Hm NHR siRNA Lib-C1-1 | A1 | A | 1 | NM_0 00475 | NR0B 1 | nuclear receptor sub-family 0, group B, member 1 | 190 | sI194 | 0.25 nmole | Not De-termined | Not Avail-able | CGAGCG CAAAGC AAACGU Att | UACGUU UGCUUU GCGCUC Gtc | 00CSIO 7NHO |

-continued

| | | | | | | | | | | | | | |
|---|---|---|---|---|---|---|---|---|---|---|---|---|---|
| 439791 4-AM003 02R-Hm NHR | CPF0 0WB K | AS00E 331 | Hm NHR siRNA Lib-C1-1 | A2 | A | 2 | NM_0 00044 | AR | androgen receptor | 367 | s1540 | 0.25 nmole | 2,2 | http://www.ambion.com/catalog/exon_sirna.php?id=1540 | CCUGAU CUGUGG AGAUGA Att | UUCAUC UCCACA GAUCAG Gca | 00CSIO 7NQG |
| 439791 4-AM003 02R-Hm NHR | CPF0 0WB K | AS00E 332 | Hm NHR siRNA Lib-C1-1 | A3 | A | 3 | NM_0 05234 | NR2F 6 | nuclear receptor sub-family 2, group F, member 6 | 2063 | s1943 99 | 0.25 nmole | 4 | http://www.ambion.com/catalog/exon_sirna.php?id=194399 | AAAAGA GACUGA UCAUCC Att | UGGAUG AUCUGA CUCUUU Utg | 000CSIO 7OFI |
| 439791 4-AM003 02R-Hm NHR | CPF0 0WB K | AS00E 333 | Hm NHR siRNA Lib-C1-1 | A4 | A | 4 | NM_0 00125 | ESR1 | estrogen receptor 1 | 2099 | s4825 | 0.25 nmole | Not De-termined | Not Avail-able | CGAGUA UGAUCC UACCAG Att | UCUGGU AGGAUC AUACUC Gga | 00CSIO 86MC |
| 439791 4-AM003 02R-Hm NHR | CPF0 0WB K | AS00E 39K | Hm NHR siRNA Lib-C1-1 | A5 | A | 5 | NM_0 01040 275 | ESR2 | estrogen receptor 2 (ER beta) | 2100 | s4828 | 0.25 nmole | 4,4,4 | http://www.ambion.com/catalog/exon_sirna.php?id=4828 | GAUUAU AUUUGU CCAGCU Att | UAGCUG GACAAA UAUAAU Cat | 000CSIO 7O5U |
| 439791 4-AM003 02R-Hm NHR | CPF0 0WB K | AS00E 39L | Hm NHR siRNA Lib-C1-1 | A6 | A | 6 | NM_0 04451 | ESRR A | estrogen related receptor alpha | 2101 | s4831 | 0.25 nmole | 6 | http://www.ambion.com/catalog/exon_sirna.php?id=4831 | CUGUCG CUGUCU GACCAG Att | UCUGGU CAGACA GCGACA Gcg | 00CSIO 7O57 |
| 439791 4-AM003 02R-Hm NHR | CPF0 0WB K | AS00E 39M | Hm NHR siRNA Lib- | A7 | A | 7 | NM_0 04452 | ESRR B | estrogen related receptor beta | 2103 | s4834 | 0.25 nmole | Not De-termined | Not Avail-able | GCAUGU GCAUUU CCUAAC Utt | AGUUAG GAAAUG CACAUG Ctg | 000CSIO 7O60 |

-continued

| | | | | | | | | | | | | |
|---|---|---|---|---|---|---|---|---|---|---|---|---|
| 439791 4- AM003 02R-Hm NHR | CPF0 0WB K | AS00E 39N | Hm NHR siRNA Lib- C1-1 | A8 | A | 8 | NM_0 01438 | ESRR G | estrogen related receptor gamma | 2104 | s4837 | 0.25 nmole | 5,7,6 | http:// www. ambion. com/ catalog/ exon_ sirna. php?id= 4837 | GACCGA GAGUUG GUGGUU Att | UAACCA CCAACU CUCGGU Cgg | 00CSIO 7O63 |
| 439791 4- AM003 02R-Hm NHR | CPF0 0WB K | AS00E 39O | Hm NHR siRNA Lib- C1-1 | A9 | A | 9 | NM_0 03822 | NR5A 2 | nuclear receptor sub- family 5, groug A, member 2 | 2494 | s5382 | 0.25 nmole | 1,1 | http:// www. ambion. com/ catalog/ exon_ sirna. php?id= 5832 | GCACGG ACUUAC ACCUAU Utt | AAUAGG UGUAAG UCCGUG Ctt | 00CSIO 7S6V |
| 439791 4- AM003 02R-Hm NHR | CPF0 0WB K | AS00E 39P | Hm NHR siRNA Lib- C1-1 | A10 | a | 10 | NM_0 04959 | NR5A 1 | nuclear receptor sub- family 5, groug A, member 1 | 2516 | s5394 | 0.25 nmole | Not De- termined | Not Avail- able | GCACGG UGCAGA ACAACA Att | UUGUUG UUCUGC ACCGUG Cgc | 00CSIO 7S71 |
| 439791 4- AM003 02R-Hm NHR | CPF0 0WB K | AS00E 39Q | Hm NHR siRNA Lib- C1-1 | A11 | A | 11 | NM_0 01489 | NR6A 1 | nuclear receptor sub- family 6, groug A, member 1 | 2649 | s5662 | 0.25 nmole | 8,8 | http:// www. ambion. com/ catalog/ exon_ sirna. php?id= 5662 | GGAGUA UGCUUG CAUGAA Att | UUUCAU GCAAGC AUACUC Ctc | 00CSIO 7SAR |
| 439791 4- AM003 02R-Hm NHR | CPF0 0WB K | Empty Well | Hm NHR siRNA Lib- C1-1 | A12 | A | 12 | | | | | | | | | | | |

-continued

| | | | | | | | | | | | | | |
|---|---|---|---|---|---|---|---|---|---|---|---|---|---|
| 4397914-AM0302R-HmNHR | CPF00WBK | AS00E39R | Hm NHR siRNA Lib-C1-1 | B1 | B | 1 | NM_000176 | NR3C1 | nuclear receptor subfamily 3, group C, member 1 (glucocorticoid receptor) | 2908 | s6187 | 0.25 nmole | 7,7,7,7,7,7 | http://www.ambion.com/catalog/exon_sirna.php?id=6187 | GCAUGU ACGACC AAUGUA Att | UUACAU UGGUCG UACAUG Cag | 00CSIO 7SLS |
| 4397914-AM0302R-HmNHR | CPF00WBK | AS00E39S | Hm NHR siRNA Lib-C1-1 | B2 | B | 2 | NM_002135 | NR4A1 | nuclear receptor subfamily 4, group A, member 1 | 3164 | s6680 | 0.25 nmole | 3,2 | http://www.ambion.com/catalog/exon_sirna.php?id=6680 | GCAUUA UGGUGU CCGCAC Att | UGUGCG GACACC AUAAUG Ctg | 00CSIO 7REL |
| 4397914-AM0302R-HmNHR | CPF00WBK | AS00E39T | Hm NHR siRNA Lib-C1-1 | B3 | B | 3 | NM_000901 | NR3C1 | nuclear receptor subfamily 3, group C, member 1 | 4306 | s8840 | 0.25 nmole | Not Determined | Not Available | GGAGCA CGAAAG UCAAAG Att | UCUUUG ACUUUC GUGCUC Cta | 00CSIO 7UF2 |
| 4397914-AM0302R-HmNHR | CPF00WBK | AS00E39U | Hm NHR siRNA Lib-C1-1 | B4 | B | 4 | NM_173172 | NR4A2 | nuclear receptor subfamily 4, group A, member 2 | 4929 | s9787 | 0.25 nmole | Not Determined | Not Available | GGCGAA CCCUGA CUAUCA Att | UUGAUA GUCAGG GUUCGC Ctg | 00CSIO 7UJI |
| 4397914-AM0302R-HmNHR | CPF00WBK | AS00E39V | Hm NHR siRNA Lib-C1-1 | B5 | B | 5 | NM_000926 | PGR | progesterone receptor | 5241 | s10417 | 0.25 nmole | Not Determined | Not Available | GACAAG UCUUAA UCAACU Att | UAGUUG AUUAAG ACUGU Cag | 00CSIO 7W5C |

| | | | | | | | | | | | | |
|---|---|---|---|---|---|---|---|---|---|---|---|---|
| 4397914-AM003 02R-HmNHR | CPF00WBK | AS00E39W | HmNHRsiRNALib-C1-1 | B6 | B | 6 | NM_001001928 | PPARA | peroxisome proliferator activated receptor alpha | 5465 | s10882 | 0.25 nmole | 8, 9 | http://www.ambion.com/catalog/exon_sirna.php?id=10882 | CCACCCGGACGAUAUCUUtt | AAAGAUAUCGUCCGGUGGtt | 00CSIO7VJV |
| 4397914-AM003 02R-HmNHR | CPF00WBK | AS00E39X | HmNHRsiRNALib-C1-1 | B7 | B | 7 | NM_006238 | PPARD | peroxisome proliferator activated receptor delta | 5467 | s10885 | 0.25 nmole | Not Determined | Not Available | CCACUACGGUGUUCAUGCAtt | UGCAUGAACACCGUAGUGGaa | 00CSI7VJY |
| 4397914-AM003 02R-HmNHR | CPF00WBK | AS00E39Y | HmNHRsiRNALib-C1-1 | B8 | B | 8 | NM_005037 | PPARG | peroxisome proliferator activated receptor gamma | 5468 | s10888 | 0.25 nmole | 2, 2, 3, 3 | http://www.ambion.com/catalog/exon_sirna.php?id=10888 | GUACCAAAGUGCAAUCAAAtt | UUUGAUUGCACUUUGGUACtc | 00CSIO7VK1 |
| 4397914-AM003 02R-HmNHR | CPF00WBK | AS00E39Z | HmNHRsiRNALib-C1-1 | B9 | B | 9 | NM_000964 | RARA | retinoic acid receptor, alpha | 5914 | s11802 | 0.25 nmole | 9, 8 | http://www.ambion.com/catalog/exon_sirna.php?id=11802 | GGAAAUGUUGGAGAACUCAtt | UGAGUUCUCCAACAUUUCCtg | 00CSIO7VXR |
| 4397914-AM003 02R-HmNHR | CPF00WBK | AS00E3A0 | HmNHRsiRNALib-C1-1 | B10 | B | 10 | NM_016152 | RARB | retinoic acid receptor, beta | 5915 | s11805 | 0.25 nmole | Not Determined | Not Available | GGCCUUACCCUAAAUCGAAtt | UUCGAUUUAGGGUAAGGCCgt | 00CSIO7WSQ |

| | | | | | | | | | | | | | |
|---|---|---|---|---|---|---|---|---|---|---|---|---|---|
| 439791 4- AM003 02R-Hm NHR | CPF0 0WB K | AS00E 3A1 | Hm NHR siRNA Lib- C1-1 | B11 | B | 11 | NM_0 00966 | RARG | retinoic acid receptor, gamma | 5916 | s1180 8 | 0.25 nmole | 5, 3 | http:// www. ambion. com/ catalog/ exon_ sirna. php?id= 11808 | CGUGUC ACCGCG ACAAAA Att | UUUUUG UCGCGG UGACAC Gtg | 00CSI0 7W5T |
| 439791 4- AM003 02R-Hm NHR | CPF0 0WB K | Empty Wells | Hm NHR siRNA Lib- C1-1 | B12 | B | 12 | | | | | | | | | | | |
| 439791 4- AM003 02R-Hm NHR | CPF0 0WB K | AS00E 3A2 | Hm NHR siRNA Lib- C1-1 | C1 | C | 1 | NM_1 34260 | RORA | RAR- related orphan receptor A | 6095 | s1210 5 | 0.25 nmole | Not De- termined | Not Avail- able | CCAUUA UGGUGU CAUUAC Att | UGUAAU GACACC AUAAUG Gat | 00CSI0 7W5W |
| 439791 4- AM003 02R-Hm NHR | CPF0 0WB K | AS00E 3A3 | Hm NHR siRNA Lib- C1-1 | C2 | C | 2 | NM_0 06914 | RORB | RAR- related orphan receptor B | 6096 | s1210 8 | 0.25 nmole | 4 | http:// www. ambion. com/ catalog/ exon_ sirna. php?id= 12108 | CUAUAG CUCUUU CAACAA Utt | AUUGUU GAAAGA GCUAUA Ggt | 00CSI0 7X7J |
| 439791 4- AM003 02R-Hm NHR | CPF0 0WB K | AS00E 3A4 | Hm NHR siRNA Lib- C1-1 | C3 | C | 3 | NM_0 01001 523 | RORC | RAR- related orphan receptor C | 6097 | s1210 8 | 0.25 nmole | 4 | http:// www. ambion. com/ catalog/ exon_ sirna. php?id= 12111 | CUAUAG CUCUUU CAACAA Utt | AUUGUU GAAAGA GCUAUA Ggt | 00CSI0 7VM8 |
| 439791 4- AM003 02R-Hm NHR | CPF0 0WB K | AS00E 3A5 | Hm NHR siRNA Lib- C1-1 | C4 | C | 4 | NM_0 02957 | RXRA | retinoid X receptor, alpha | 6256 | s1238 6 | 0.25 nmole | Not De- termined | Not Avail- able | AGGACU GCCUGA UUGACA Att | UUGUCA AUCAGG CAGUCC Utg | 00CSI0 7IK2 |

| | | | | | | | | | | | |
|---|---|---|---|---|---|---|---|---|---|---|---|
| 439791 4- AM003 02R-Hm NHR | CPF0 0WB K | AS00E 3A6 | Hm NHR siRNA Lib- C1-1 | C5 | C | 5 | NM_0 21976 | RXRB | retinoid X receptor, beta | 6257 | s1238 9 | 0.25 nmole | 8 | http:// www. ambion. com/ catalog/ exon_ sirna. php?id= 1389 | ACAGAG CUAGUG UCCAAA Att | UUUUGG ACACUA GCUCUG Uca | 00CSIO 7P92 |
| 439791 4- AM003 02R-Hm NHR | CPF0 0WB K | AS00E 3A7 | Hm NHR siRNA Lib- C1-1 | C6 | C | 6 | NM_0 05654 | NR2F 1 | nuclear receptor sub- family 2, group F, member 1 | 7025 | s1402 0 | 0.25 nmole | 3 | http:// www. ambion. com/ catalog/ exon_ sirna. php?id= 14020 | UCUCAU CCGCGA UAUGUU Att | UAACAU ACUGCG GAUGAG Agt | 00CSIO 7W67 |
| 439791 4- AM003 02R-Hm NHR | CPF0 0WB K | AS00E 3A8 | Hm NHR siRNA Lib- C1-1 | C7 | C | 7 | NM_0 21005 | NR2F2 | nuclear receptor sub- family 2, group F, member 2 | 7026 | s1402 3 | 0.25 nmole | Not De- termined | Not Avail- able | CCUCCU CAGUCA UAGAGC Att | UGCUCU AUGACU GAGGAG Gag | 00CSIO 7W6A |
| 439791 4- AM003 02R-Hm NHR | CPF0 0WB K | AS00E 3A9 | Hm NHR siRNA Lib- C1-1 | C8 | C | 8 | NM_0 03250 | THRA | thyroid hormone receptor, alpha (erythrob lastic leukemia viral (v-erb- a) oncogene homolog, avian | 7067 | s1411 8 | 0.25 nmole | 3, 3 | http:// www. ambion. com/ catalog/ exon_ sirna. php?id= 14118 | GAUGGA AAGCGA AAAAGA Att | UUCUUU UUCGCU UUCCAU Ctg | 00CSO0 7W6D |

-continued

| | | | | | | | | | | | | | | |
|---|---|---|---|---|---|---|---|---|---|---|---|---|---|---|
| 4397914-AM003 02R-Hm NHR | CPF00WBK | AS00E3AA | Hm NHR siRNA Lib-C1-1 | C9 | C | 9 | NM_000461 | THRB | thyroid hormone receptor, alpha (erythroblastic leukemia viral (v-erb-a) oncogene homolog 2, avian | 7068 | s14121 | 0.25 nmole | Not Determined | Not Available | CACUAU AUCAAU UACCGA Att | UUCGGU AAUUGA UAUAGU Gtt | 00CSIO 7W6G |
| 4397914-AM003 02R-Hm NHR | CPF00WBK | AS00E3AB | Hm NHR siRNA Lib-C1-1 | C10 | C | 10 | NM_003269 | NR2E1 | nuclear receptor subfamily 2, group E, member 1 | 7101 | s14202 | 0.25 nmole | Not Determined | Not Available | CACUCA ACCCUG UCGCUU Utt | AAAGCG ACAGGG UUGAGU Ggg | 00CSIO 7W6J |
| 4397914-AM003 02R-Hm NHR | CPF00WBK | AS00E3AC | Hm NHR siRNA Lib-C1-1 | C11 | C | 11 | NM_001032287 | NR2C1 | nuclear receptor subfamily 2, group C, member 1 | 7181 | s14369 | 0.25 nmole | Not Determined | Not Available | GCGAUU CACAUG UAGCUU Utt | AAAGCU ACAUGU GAAUCG Ctg | 00CSIO 7W6M |
| 4397914-AM003 02R-Hm NHR | CPF00WBK | Empty Well | Hm NHR siRNA Lib-C1-1 | C12 | C | 12 | | | | | | | | | | |
| 4397914-AM003 02R-Hm NHR | CPF00WBK | AS00E3AD | Hm NHR siRNA Lib-C1-1 | D1 | D | 1 | NM_003298 | NR2C1 | nuclear receptor subfamily 2, group C, member 2 | 7182 | s14372 | 0.25 nmole | 15 | http://www.ambion.com/catalog/exon_sirna.php?id=14372 | GCUUCA ACAUAA CAGAAG Att | UCUUCU GUUAUG UUGGAG Ctc | 00CSIO 7I5D |

-continued

| | | | | | | | | | | | | | |
|---|---|---|---|---|---|---|---|---|---|---|---|---|---|
| 439791 4- AM003 02R-Hm NHR | CPF0 0WB K | AS00E 3AE | Hm NHR siRNA Lib- C1-1 | D2 | D | 2 | NM_0 07121 | NR1H 2 | nuclear receptor sub- family 1, group H, member 2 | 7376 | s1468 6 | 0.25 nmole | 7 | http:// www. ambion. com/ catalog/ exon_ sirna. php?=id= 14686 | AGAUCG UGGACU UCGCUA Att | UUAGCG AAGUCC ACGAUC Ucc | 00CSI0 7LYG |
| 439791 4- AM003 02R-Hm NHR | CPF0 0WB K | AS00E 3AF | Hm NHR siRNA Lib- C1-1 | D3 | D | 3 | NM_0 00376 | VDR | vitamin D (1, 25- dihy- droxy vitamin D3) receptor | 7421 | S1477 9 | 0.25 nmole | 6,7 | http:// www. ambion. com/ catalog/ exon_ sirna. php?=id= 14779 | AGAUCA CUGUAU CACCUC Utt | AGAGGU GAUACA GUGAUC Uga | 00CSI0 7W6R |
| 439791 4- AM003 02R-Hm NHR | CPF0 0WB K | AS00E 3AG | Hm NHR siRNA Lib- C1-1 | D4 | D | 4 | NM_0 06981 | NR4A 3 | nuclear receptor sub- family 4, group A, member 3 | 8013 | s1554 3 | 0.25 nmole | 5,5,4 | http:// www. ambion. com/ catalog/ exon_ sirna. php?=id= 15543 | AGAUCU UGAUUA UUCCAG Att | UCUGGA AUAAUC AAGAUC Uct | 00CSI0 7W6U |
| 439791 4- AM003 02R-Hm NHR | CPF0 0WB K | AS00E 3AH | Hm NHR siRNA Lib- C1-1 | D5 | D | 5 | NM_0 21960 | NR0B 2 | nuclear receptor sub- family 0, group B, member 2 | 8431 | s1599 8 | 0.25 nmole | Not De- termined | Not Avail- able | CGGUGC CCAGCA UACUCA Att | UUGAGU AUGCUG GGCACC Ggg | 00CSI0 7W6W |
| 439791 4- AM003 02R-Hm NHR | CPF0 0WB K | AS00E 3AI | Hm NHR siRNA Lib- C1-1 | D6 | D | 6 | NM_0 22002 | NR1|2 | nuclear receptor sub- family 1, group I, member 2 | 8856 | s1691 1 | 0.25 nmole | Not De- termined | Not Avail- able | GGCUAU CACUUC AAUGUC Att | UGACAU UGAAGU GAUAGC Cag | 00CSI0 7W6Z |

-continued

| | | | | | | | | | | | | | | |
|---|---|---|---|---|---|---|---|---|---|---|---|---|---|---|
| 439791 4- AM003 02R-Hm NHR | CPF0 0WB K | AS00E 3AJ | Hm NHR siRNA Lib-C1-1 | D7 | D | 7 | NM_0 21724 | NR1D 1 | nuclear receptor sub-family 1, group D, member 1 | 9572 | s1838 8 | 0.25 nmole | 7 | http:// www. ambion. com/ catalog/ exon_ sirna. php?=id= 18388 | CGCUUU GCUUCG UUGUUC Att | UGAACA ACGAAG CAAAGC Gca | 00CSI0 7RYC |
| 439791 4- AM003 02R-Hm NHR | CPF0 0WB K | AS00E 3AK | Hm NHR siRNA Lib-C1-1 | D8 | D | 8 | NM_0 01077 469 | NR1I 3 | nuclear receptor sub-family 1, group I, member 3 | 9970 | s1937 0 | 0.25 nmole | 5, 4, 5, 4, 4, 5, 4, 4, 4, 5, | http:// www. ambion. com/ catalog/ exon_ sirna. php?=id= 19370 | AAGUCA UCAAGU UUACUA Att | UUAGUA AACUUG AUGACU Ugc | 00CSI0 7W72 |
| 439791 4- AM003 02R-Hm NHR | CPF0 0WB K | AS00E 3AL | Hm NHR siRNA Lib-C1-1 | D9 | D | 9 | NM_0 05123 | NR1H 4 | nuclear receptor sub-family 1, group H, member 4 | 9971 | s1937 3 | 0.25 nmole | 4 | http:// www. ambion. com/ catalog/ exon_ sirna. php?=id= 19373 | GAACCA UACUCG CAAUAC Att | UGUAUU GCGAGU AUGGUU Cca | 00CSI0 7W74 |
| 439791 4- AM003 02R-Hm NHR | CPF0 0WB K | AS00E 3AM | Hm NHR siRNA Lib-C1-1 | D10 | D | 10 | NM_0 01130 839 | NR1D 2 | nuclear receptor sub-family 1, group D, member 2 | 9975 | s1938 2 | 0.25 nmole | Not De-termined | Not Avail-able | GCGUAU UCCUGG GUUCAG Att | UCUGAA CCCAGG AAUACG Ctt | 00CSI0 7QBW |
| 439791 4- AM003 02R-Hm NHR | CPF0 0WB K | AS00E 3AN | Hm NHR siRNA Lib-C1-1 | D11 | D | 11 | NM_0 14249 | NR2E 3 | nuclear receptor sub-family 2, group E, member 3 | 1000 2 | s1950 10 | 0.25 nmole | 4, 4 | http:// www. ambion. com/ catalog/ exon_ sirna. php?=id= 195010 | CCAGCC UUAUAA CAGCUG Att | UCAGCU GUUAUA AGGCUG Gct | 00CSI0 7W7D |

-continued

| | | | | | | | | | | | |
|---|---|---|---|---|---|---|---|---|---|---|---|
| 439791 4- AM003 02R-Hm NHR | CPF0 0WB K | AS00E 3AO | Hm NHR siRNA Lib- C1-1 | E1 | E | 1 | NM_0 05693 | NR1H3 | nuclear receptor sub- family 1, group H, member 3 | 1006 2 | s1957 0 | 0.25 nmole | Not De- termined | Not Avail- able | ACAGAG AUCCGU CCAAA Att | UUUGUG GACGGA UCUCUG Ugg | 00CSI0 7W79 |
| 439791 4- AM003 02R-Hm NHR | CPF0 0WB K | AS00E 3AP | Hm NHR siRNA Lib- C1-1 | E2 | E | 2 | NM_0 52951 | DNTTI P1 | deoxy- nucleo- trans- ferase, terminal, inter- acting protein 3 | 1160 92 | s4192 4 | 0.25 nmole | 2 | http:// www. ambion. com/ catalog/ exon_ sirna. php?-id= 41924 | CCUUGG AACAUA AUGAUA Att | UUAUCA UUAUGU UCCAAG Ggt | 00CSI0 7W7C |
| 439791 4- AM003 02R-Hm NHR | CPF0 0WB K | AS00E 3AQ | Hm NHR siRNA Lib- C1-1 | E3 | E | 3 | NM_0 6917 | RXRG | retinoid X receptor, gamma | 6258 | s2004 56 | 0.25 nmole | 5 | http:// www. ambion. com/ catalog/ exon_ sirna. php?-id= 200456 | AGAGGA UUCUAG AAGCUG Att | UCAGCU UCUAGA AUCCUC Ucc | 00CSI0 7W7G |
| 439791 4- AM003 02R-Hm NHR | CPF0 0WB K | Empty Wells | Hm NHR siRNA Lib- C1-1 | E5 | E | 5 | | | | | | | | | | | |
| 439791 4- AM003 02R-Hm NHR | CPF0 0WB K | Empty Wells | Hm NHR siRNA Lib- C1-1 | E6 | E | 6 | | | | | | | | | | | |
| 439791 4- AM003 02R-Hm NHR | CPF0 0WB K | Empty Wells | Hm NHR siRNA Lib- C1-1 | E7 | E | 7 | | | | | | | | | | | |
| 439791 4- AM003 02R-Hm NHR | CPF0 0WB K | Empty Wells | Hm NHR siRNA Lib- C1-1 | E8 | E | 8 | | | | | | | | | | | |

| 4397914-AMO03 02R-Hm NHR | CPF0 OWB K | Empty Wells | Hm NHR siRNA Lib-C1-1 | E9 | E | 9 |
| --- | --- | --- | --- | --- | --- | --- |
| 4397914-AMO03 02R-Hm NHR | CPF0 OWB K | Empty Wells | Hm NHR siRNA Lib-C1-1 | E10 | E | 10 |
| 4397914-AMO03 02R-Hm NHR | CPF0 OWB K | Empty Wells | Hm NHR siRNA Lib-C1-1 | E11 | E | 11 |
| 4397914-AMO03 02R-Hm NHR | CPF0 OWB K | Empty Wells | Hm NHR siRNA Lib-C1-1 | E12 | E | 12 |
| 4397914-AMO03 02R-Hm NHR | CPF0 OWB K | Empty Wells | Hm NHR siRNA Lib-C1-1 | F1 | F | 1 |
| 4397914-AMO03 02R-Hm NHR | CPF0 OWB K | Empty Wells | Hm NHR siRNA Lib-C1-1 | F2 | F | 2 |
| 4397914-AMO03 02R-Hm NHR | CPF0 OWB K | Empty Wells | Hm NHR siRNA Lib-C1-1 | F3 | F | 3 |
| 4397914-AMO03 02R-Hm NHR | CPF0 OWB K | Empty Wells | Hm NHR siRNA Lib-C1-1 | F4 | F | 4 |
| 4397914-AMO03 02R-Hm NHR | CPF0 OWB K | Empty Wells | Hm NHR siRNA Lib-C1-1 | F5 | F | 6 |

-continued

| | | | | | |
|---|---|---|---|---|---|
| 439791-4-AMO03 02R-Hm NHR | CPF0 0WB K | Empty Wells | Hm NHR siRNA Lib-C1-1 | F6 | F 6 |
| 439791-4-AMO03 02R-Hm NHR | CPF0 0WB K | Empty Wells | Hm NHR siRNA Lib-C1-1 | F7 | F 7 |
| 439791-4-AMO03 02R-Hm NHR | CPF0 0WB K | Empty Wells | Hm NHR siRNA Lib-C1-1 | F8 | F 8 |
| 439791-4-AMO03 02R-Hm NHR | CPF0 0WB K | Empty Wells | Hm NHR siRNA Lib-C1-1 | F9 | F 9 |
| 439791-4-AMO03 02R-Hm NHR | CPF0 0WB K | Empty Wells | Hm NHR siRNA Lib-C1-1 | F10 | F 10 |
| 439791-4-AMO03 02R-Hm NHR | CPF0 0WB K | Empty Wells | Hm NHR siRNA Lib-C1-1 | F11 | F 11 |
| 439791-4-AMO03 02R-Hm NHR | CPF0 0WB K | Empty Wells | Hm NHR siRNA Lib-C1-1 | F12 | F 12 |
| 439791-4-AMO03 02R-Hm NHR | CPF0 0WB K | Empty Wells | Hm NHR siRNA Lib-C1-1 | G1 | G 1 |
| 439791-4-AMO03 02R-Hm NHR | CPF0 0WB K | Empty Wells | Hm NHR siRNA Lib-C1-1 | G2 | G 2 |

-continued

| 4397914-AMO03 02R-Hm NHR | CPF00WB K | Empty Wells | Hm NHR siRNA Lib-C1-1 | G3 | G | 3 |
| --- | --- | --- | --- | --- | --- | --- |
| 4397914-AMO03 02R-Hm NHR | CPF00WB K | Empty Wells | Hm NHR siRNA Lib-C1-1 | G4 | G | 4 |
| 4397914-AMO03 02R-Hm NHR | CPF00WB K | Empty Wells | Hm NHR siRNA Lib-C1-1 | G5 | G | 5 |
| 4397914-AMO03 02R-Hm NHR | CPF00WB K | Empty Wells | Hm NHR siRNA Lib-C1-1 | G6 | G | 6 |
| 4397914-AMO03 02R-Hm NHR | CPF00WB K | Empty Wells | Hm NHR siRNA Lib-C1-1 | G7 | G | 7 |
| 4397914-AMO03 02R-Hm NHR | CPF00WB K | Empty Wells | Hm NHR siRNA Lib-C1-1 | G8 | G | 8 |
| 4397914-AMO03 02R-Hm NHR | CPF00WB K | Empty Wells | Hm NHR siRNA Lib-C1-1 | G9 | G | 9 |
| 4397914-AMO03 02R-Hm NHR | CPF00WB K | Empty Wells | Hm NHR siRNA Lib-C1-1 | G10 | G | 10 |
| 4397914-AMO03 02R-Hm NHR | CPF00WB K | Empty Wells | Hm NHR siRNA Lib-C1-1 | G11 | G | 11 |

-continued

| | | | | | |
|---|---|---|---|---|---|
| 439791 4- AM003 02R-Hm NHR | CPF0 0WB K | Empty Wells | Hm NHR siRNA Lib- C1-1 | G12 | G | 12 |
| 439791 4- AM003 02R-Hm NHR | CPF0 0WB K | Empty Wells | Hm NHR siRNA Lib- C1-1 | H1 | H | 1 |
| 439791 4- AM003 02R-Hm NHR | CPF0 0WB K | Empty Wells | Hm NHR siRNA Lib- C1-1 | H2 | H | 2 |
| 439791 4- AM003 02R-Hm NHR | CPF0 0WB K | Empty Wells | Hm NHR siRNA Lib- C1-1 | H3 | H | 3 |
| 439791 4- AM003 02R-Hm NHR | CPF0 0WB K | Empty Wells | Hm NHR siRNA Lib- C1-1 | H4 | H | 4 |
| 439791 4- AM003 02R-Hm NHR | CPF0 0WB K | Empty Wells | Hm NHR siRNA Lib- C1-1 | H5 | H | 5 |
| 439791 4- AM003 02R-Hm NHR | CPF0 0WB K | Empty Wells | Hm NHR siRNA Lib- C1-1 | H6 | H | 6 |
| 439791 4- AM003 02R-Hm NHR | CPF0 0WB K | Empty Wells | Hm NHR siRNA Lib- C1-1 | H7 | H | 7 |
| 439791 4- AM003 02R-Hm NHR | CPF0 0WB K | Empty Wells | Hm NHR siRNA Lib- C1-1 | H8 | H | 8 |

-continued

| | | | | | |
|---|---|---|---|---|---|
| 4397914-AM0302R-Hm-NHR | CPF00WBK | Empty Wells | Hm NHR siRNA Lib-C1-1 | H9 | H 9 |
| 4397914-AM0302R-Hm-NHR | CPF00WBK | Empty Wells | Hm NHR siRNA Lib-C1-1 | H10 | H 10 |
| 4397914-AM0302R-Hm-NHR | CPF00WBK | Empty Wells | Hm NHR siRNA Lib-C1-1 | H11 | H 11 |
| 4397914-AM0302R-Hm-NHR | CPF00WBK | Empty Wells | Hm NHR siRNA Lib-C1-1 | H12 | H 12 |

Ambion Silencer ® Select siRNA Library Summary Information
Ambion Order Number: AM00302R
Catalog Number: 4397914
Quantity (nole): 0.25 nmole
Total Plate Count: 3
Total Sample Count: 141
siRNA Count: 141
Control Count: 0
Empty Well Count: 147

The invention claimed is:

1. A method for increasing cancer cell susceptibility to NK cell cytotoxicity in a subject having a cancer or a precancerous condition, said method comprising administering to said subject a therapeutically effective amount of an RXR-gamma agonist of formula (I)

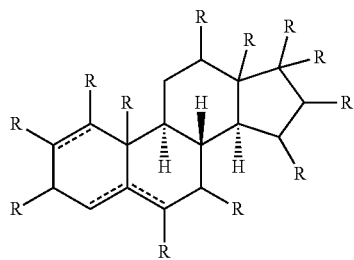

wherein,
each of R is independently hydrogen, halogen, R*, —OH, =O, —NO$_2$, —CN, OR$^{\#}$, —SR$^{\#}$, —N(R$^{\#}$)$_2$, —C(O)R$^{\#}$, —CO$_2$R$^{\#}$, —C(O)C(O)R$^{\#}$, —C(O)CH$_2$C(O)R$^{\#}$, —S(O)R$^{\#}$, —S(O)$_2$R$^{\#}$, —C(O)N(R$^{\#}$)$_2$, —SO$_2$N(R$^{\#}$)$_2$, —N(R$^{\#}$)C(O)R$^{\#}$, —N(R$^{\#}$)N(R$^{\#}$)$_2$, —N(R$^{\#}$)C(=NR$^{\#}$)N(R$^{\#}$)$_2$, —C(=NR$^{\#}$)N(R$^{\#}$)$_2$, —C=NOR$^{\#}$, —N(R$^{\#}$)C(O)N(R$^{\#}$)$_2$, —N(R$^{\#}$)SO$_2$N(R$^{\#}$)$_2$, —N(R$^{\#}$)SO$_2$R$^{\#}$, —OC(O)N(R$^{\#}$)$_2$, or an optionally substituted C$_{1-12}$ aliphatic group, or two R groups are taken together with their intervening atoms to form an optionally substituted 3- to 7-membered ring having 0-4 heteroatoms selected from nitrogen, oxygen, or sulfur;
each R$^4$ is independently hydrogen or R*;
each R* is independently an optionally substituted group selected from C$_{1-10}$ aliphatic, aryl, a 3-7 membered saturated or partially unsaturated carbocyclic ring, a 3-7 membered saturated or partially unsaturated monocyclic heterocyclic ring having 0-2 heteroatoms independently selected from nitrogen, oxygen, or sulfur, or a heteroaryl ring having 0-3 heteroatoms independently selected from nitrogen, oxygen, or sulfur; or: two R* groups on the same nitrogen are taken together with their intervening atoms to form an optionally substituted 3-7 membered saturated, partially unsaturated, or heteroaryl ring having 0-4 heteroatoms independently selected from nitrogen, oxygen, or sulfur, or an enantiomer, diastereomer, tautomer, solvate, prodrug or pharmaceutical acceptable salt thereof, wherein said cancer is selected from colorectal adenoma, colorectal cancer, head and neck cancer, prostate cancer, rhabdomyosarcoma, hepatocellular carcinoma, hepatocellular adenoma, osteosarcoma, and renal cancer.

2. The method of claim 1, wherein the compound of formula (I) is

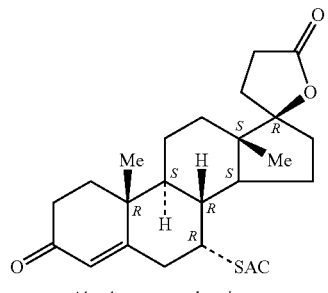

Absolute stereochemistry.
CAS (52-01-7) Spironolactone (1)

or an enantiomer, diastereomer, tautomer, solvate, prodrug or pharmaceutical acceptable salt thereof.

3. The method of claim 1, wherein the subject is human.

* * * * *

SEQUENCE LISTING

<160> NUMBER OF SEQ ID NOS: 31

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gggagaaggu cuaugcguc                                                    19

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
aaaugacccu guuaccaact t                                                 21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
guugguaaca gggucauuug t                                                 21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
ggaucucugg uuaaacacat t                                                 21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
uguguuuaac cagagauccg g                                                 21

```
<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 6
agaggauucu agaagcugat t                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
ucagcuucua gaauccucuc c                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8
gcauuaugcg ugauuacugt t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 9
caguaaucac gcauaaugct g                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 10
acugacgagu aaacauguat t                                              21
```

```
<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11
uacauguuua cucgucagut c                                              21

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
guaaagauaa acugacgau                                                 19

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
ccgacaugcu cuccaauuu                                                 19

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccttggccat gaacgtcagg                                                20

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cctctgaggc ctcgctgcg                                                 19

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
accttggcta tgaacgtcac a                                              21
```

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ccctctgaga cctcgctgca                                                   20

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
atcagcgcct cctgtccac                                                    19

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aaagacagtg tgtgtcgacc cat                                               23

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aaatgtcaca acggcctg                                                     18

<210> SEQ ID NO 21
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgaggggttc cttggg                                                       16

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cgattcttcc gtacctgcta ttcg                                              24

```
<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aattcttctg atccacctgg ctct                                             24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tcggtctgaa aggtgtggcc ttta                                             24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aggtatttga gcggcttcct ctgt                                             24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tcctgctact acctgccttg cttt                                             24

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
agccagggta accgaaattg gaga                                             24

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
atggggaagg tgaaggtcg                                                   19
```

```
<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggggtcattg atggcaacaa ta                                             22

<210> SEQ ID NO 30
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
ccaugaacgu caggaauuu                                                 19

<210> SEQ ID NO 31
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
aggcuuagcu caacccaaa                                                 19
```